(12) United States Patent
Laga

(10) Patent No.: US 10,480,004 B2
(45) Date of Patent: Nov. 19, 2019

(54) *BRASSICA* PLANT COMPRISING A MUTANT ALCATRAZ ALLELE

(75) Inventor: Benjamin Laga, Wingene (BE)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 1504 days.

(21) Appl. No.: 13/994,173

(22) PCT Filed: Dec. 16, 2011

(86) PCT No.: PCT/EP2011/073135
§ 371 (c)(1),
(2), (4) Date: Jul. 8, 2013

(87) PCT Pub. No.: WO2012/084742
PCT Pub. Date: Jun. 28, 2012

(65) Prior Publication Data
US 2013/0291235 A1 Oct. 31, 2013

Related U.S. Application Data

(60) Provisional application No. 61/429,594, filed on Jan. 4, 2011.

(30) Foreign Application Priority Data

Dec. 24, 2010 (EP) .................................... 10075765

(51) Int. Cl.
*C12N 15/82* (2006.01)
*C12N 15/113* (2010.01)

(52) U.S. Cl.
CPC ..... *C12N 15/8271* (2013.01); *C12N 15/8218* (2013.01); *C12N 15/8266* (2013.01)

(58) Field of Classification Search
None
See application file for complete search history.

(56) References Cited

U.S. PATENT DOCUMENTS

| | | | | |
|---|---|---|---|---|
| 5,773,689 A * | 6/1998 | Thompson | ............ | C07K 14/395 435/320.1 |
| 5,985,557 A | 11/1999 | Prudent et al. | | |
| 6,001,567 A | 12/1999 | Brow et al. | | |
| 7,786,349 B2 * | 8/2010 | De Block | ........... | C12N 15/8271 800/285 |

FOREIGN PATENT DOCUMENTS

| | | |
|---|---|---|
| EP | 0534858 | 3/1993 |
| WO | WO97/13865 | 4/1997 |
| WO | WO99/00503 | 1/1999 |
| WO | WO99/53050 | 10/1999 |
| WO | WO00/01133 | 1/2000 |
| WO | WO01/59121 | 8/2001 |
| WO | WO01/59122 | 8/2001 |
| WO | WO01/79517 | 10/2001 |
| WO | WO02/059294 | 8/2002 |
| WO | WO03/076619 | 9/2003 |
| WO | WO04/113542 | 12/2004 |
| WO | WO06/105946 | 10/2006 |
| WO | WO09/002150 | 12/2008 |
| WO | WO10/006732 | 1/2010 |

OTHER PUBLICATIONS

Osoegawa et al Genomics, 2007, 89(2): 291-299.*
Whisstock et al (Quarterly Reviews of Biophysics, 2003, 36(3): 307-340).*
Ossowski et al (The Plant Journal, 2008, 53:674-690).*
Hua et al (Planta, 2009, 230:493-505); cited on IDS.*
Vos et al. 1995, AFLP: a new technique for DNA fingerprinting, NAR vol. 23:No. 21, 4407-4414.
International Search Report for PCT Application No. PCT/EP2011/073135 dated Dec. 16, 2011.
Ausubel et al. 1994 vol. 1 and 2, Current Protocols in Molecular Biology, Current Protocols, USA.
Azpiroz-Leehan et al. 1997 T-DNA Insertion Mutagenesis in *Arabidopsis* going back and forth, Trends Genet 13:152-156.
Bagheri H. 2009, Genetic analysis of breeding traits in *Brassica rapa*, Wageningen University, p. 72-83, fig 2g.
Brown, 1998 vol. I & II of Molecular Biology LabFax, 2nd Edition, Academic Press (UK).
Bruce et al. 2001, Threshability of Shatter-resistant Seed Pods in Oilseed Rape, J. Agric. Engng Res. 80, 343-350.
Bruce et al. 2002, Determining the Oilseed Rape Pod Strength Needed to Reduce Seed Loss due to Pod Shatter, Biosystems Eng 81(2): 179-184.
Child et al. 1998, Anatomical Variation in the Dehiscence Zone of Oilseed Rape Pods and its relevance to Pod Shatter, J Exp Bot 49: 829-838.
Child and Huttly, 1999, Ethylene Biosynthesis in Oilseed Rape Pods in Relation to pod shatter, Proc 10th Int. Rapeseed Congress.
Child et al. 2003, Increased resistance to pod shatter is associated with changes in the vascular structure in pods of a resynthesized *Brassica napus* line, J Exp Botany 54 (389): 1919-1930.
Croy R.D.D.1993 Plant Molecular Biology Labfax BIOS Scientific Publications Ltd (UK) and Blackwell Scientific Publications, UK.
Davies and Bruce, 1997, Fracture mechanics of oilseed rape pods, J Mat Sci 32: 5895-5899.
Dieffenbach and Dveksler 1995 PCR Primer: A Laboratory Manual, Cold Spring Harbor Laboratory Press.
Dinneny et al. 2004, The role of JAGGED in shaping lateral organs, Development 131, 1101-1110.
Dinneny et al. 2005, A genetic framework for fruit patterning in *Arabidopsis thaliana*, Development 132, 4687-4696.
Doyle and Doyle, 1987, DNA isolation from small amounts of plant tissue, Phytochemistry Bulletin 19:11-15.

(Continued)

*Primary Examiner* — Stephen Uyeno
(74) *Attorney, Agent, or Firm* — Arent Fox LLP

(57) ABSTRACT

The present invention relates to *Brassica* plants comprising mutant ALC genes, ALC nucleic acid sequences and proteins, as well as methods for generating and identifying said plants and alleles, which can be used to plants with increased podshatter resistance.

9 Claims, 13 Drawing Sheets

Specification includes a Sequence Listing.

(56) References Cited

OTHER PUBLICATIONS

Ferrandiz et al. 2000, Negative Regulation of the SHATTER-PROOF Genes by Fruitfull During *Arabidopsis* Fruit Development, Science, 289, 436-438.
Heim et al., 2003, The Basic Helix-Loop-Helix Transcription Factor Family in Plants: A Genome-Wide Study of Protein Structure and Functional Diversity, Mol Biol Evol 20, 735-747.
Henikoff et al., TILLING Traditional Mutagenesis Meets Functional Genomics 2004, Plant Physiology 135(2):630-6.
Hua et al. 2009, Sequence, expression divergence, and complementation of homologous ALCATRAZ loci in *Brassica napus*, Planta 230: 493-503.
Kadkol et al. 1986, Anatomical Basis of Shatter-resistance in the Oilseed *Brassicas*, Aust. J. Botany 34 595-601.
Kadkol G. "*Brassica* shatter resistance research update" 16th Australian Research Assembly on *Brassicas* Jan. 12, 2009—http://www;australianoilseeds.com.
Li et al. 2001, A fast neutron deletion mutagenesis-based reverse genetics system for plants, Plant J 27: 235-242.
Li and Zhang, 2002, Reverse genetics by fast neutron mutagenesis in higher plants, Funct Integr Genomics 2:254-258.
Liljegren et al. 2000, SHATTERPROOFMADS-box genes control seed dispersal in *Arabidopsis*, Nature 404, 766-770.
Liljegren et al. 2004, Control of Fruit Patterning in *Arabidopsis* by INDEHISCENT, Cell 116: 843-85.
MacLeod, 1981, Harvesting in Oilseed Rape, pp. 107-120 Cambridge Agricultural Publishing, Cambridge.
McCallum et al. 2000, Targeted screening for induced mutations, Nat Biotechnol 18:455-457.
McCallum et al. 2000, Targeting Induced Local Lesions IN Genomes (TILLING) for Plant Functional Genomics, Plant Physiol. 123, 439-442.
McKenzie et al. 2002, Tissue-culture enhanced transposition of the maize transposable element Dissociation in *Brassica oleracea* var. '*Italica*', Theor Appl Genet 105:23-33.
McPherson et al. 2000 PCR—School of Biochemistry and Molecular Biology, University of Leeds, Laboratory of Plant Molecular Biology, Rockefeller University, Basics: From Background to Bench, First Edition, Springer Verlag, Germany.
Meakin and Roberts, 1990, Dehiscence of Fruit in Oilseed Rape (*Brassica napus* L.), J Exp Bot 41, 995-1011.
Morgan et al. 1998 Genetic variation for pod shatter resistance among lines of oilseed rape developed from synthetic *B. napus*, Fields Crop Research 58, 153-165.
Mott, 1997, Est Genome: a program to align spliced DNA sequences to unspliced genomic DNAComput. Applic. 13:477-478.
Murre et al. 1989, A New DNA Binding and Dimerization Motif in Immunoglobulin Enhancer Binding, daughterless, MyoD, and myc Proteins, Cell 56, 777-783.
Needleman and Wunsch, 1970, A General Method Applicable to the Search for Similarities in the Amino Acid Sequence of Two Proteins, J Mol Biol 48(3): 443-53.
Ohno et al. 2004, The *Arabidopsis* JAGGED gene encodes a zinc finger protein that promotes leaf tissue development, Development 131, 1111-1122.
Petersen et al. 1996, Isolation and characterisation of a pod dehiscence zone-specific polygalacturonase from *Brassica napus*, Plant. Mol. Biol., 31:517-527.
Prakash and Chopra, 1988, Introgression of resistance to shaterring in *Brassicia napus* from . . . , Plant breeding 101: 167-168.
Prakash and Chopra, 1990, Introgression of resistance to shaterring in *Brassicia napus* from . . . ,Genetical Research 56: 1-2.
Ptashne, 1988, How eukaryotic transcriptional activators work, Nature 335, 683-689.
Quong et al. 1993, A New Transcriptional-Activation Motif Restricted to a Class of Helix-Loop-Helix Proteins Is Functionally Conserved in Both Yeast and Mammalian Cells, Mol Cell Biol 13, 792-800.
Rajani et al. 2001, The *Arabidopsis* myc/bHLH gene ALCATRAZ enables cell separation in fruit dehiscence, Current Biology 11, 1914-1922.
Rice et al. 2000, Emboss: The European Molecular Biology Open Software SuiteTrends in Genetics 16(6): 276-277.
Sambrook et al. 1989 Molecular Cloning: A Laboratory Manual, 2nd Edition, Cold Spring Harbour Laboratory Press, NY.
Sambrook and Russell 2001 Molecular Cloning: A Laboratory Manual, 3rd Edition, Cold Spring Harbour Laboratory Press, NY.
Sawa et al., 1999, Filamentous Flower, a meristem and organ identity gene of *Arabidopsis*, encodes a protein with a zinc finger and HMG-related domains, Genes Dev. 13, 1079-1088.
Siegfried et al. 1999, Members of the YABBY gene family specify abaxial cell fate in *Arabidopsis*, Development 126, 4117-4128.
Snowdon 2007, Cytogenetics and genome analysis in *Brassica* crops, Chromosome research 15: 85-95.
Spence et al. 1996, Pod shatter in *Arabidopsis thaliana*, *Brassica napus* and *B. Junces*, PJ of Microscopy 181: 195-203.
Toledo-Ortiz et al. 2003, The *Arabidopsis* Basic/Helix-Loop-Helix Transcription Factor Family, Plant Cell 15, 1749-1770.

\* cited by examiner

```
                      1                                                    50
PPS_ALC_CDS_GR3       ..........  ..........  ..........  ..........  ..........
 PPS_ALC_A1_GR3       ......GATT  ATGGCTAGAG  TGATTTGCCA  CGCGCCTGCC  TATTTATTAT
PPS_ALC_CDS_GR4       ..........  ..........  ..........  ..........  ..........
 PPS_ALC_C1_GR4       ...CCAGATT  ATGTCTAGAG  TGATTTGCCA  CGCGCCTGCC  TATTTATTAT
    PPS_ALC_GR1       ACGAAAACCA  CCATCGTCCG  ATTCATCATC  CGTCAACTTT  GGCCCACTGG
    PPS_ALC_GR6       ..........  ..........  ..........  .CCCCAAGCC  TCCTCATGCC
    PPS_ALC_GR5       ...GCTCATA  AATCACGCGC  GTACTTCCCC  ACCTATTTAT  TATGAAAAGC
    PPS_ALC_GR2       ..........  ..........  ..........  ..........  ..........

51                                                   100
PPS_ALC_CDS_GR3       ..........  ..........  ..........  ..........  ..........
 PPS_ALC_A1_GR3       GAAAAGCCTC  AGTAACTCTG  TGACGAGAAG  AATTCACAGA  GAGAGAGAGG
PPS_ALC_CDS_GR4       ..........  ..........  ..........  ..........  ..........
 PPS_ALC_C1_GR4       GAAAAGCCTC  .AGTAACTTG  TGATGAGAAG  AATTCAC..A  GAGAGAGAGG
    PPS_ALC_GR1       GTTTGGACAC  AAGTGCGTCG  TACTGCGGCT  GTTCCAGTTT  AATGTCGAAG
    PPS_ALC_GR6       GTCTGGACAC  AAGTGCGTCG  TACTGTGGCT  GTTCCAGTTT  AATGTCGAAG
    PPS_ALC_GR5       CTCAGTAAAC  TAGTAAAGTG  AATTGTGAAG  GATTACAGAG  AGAC....AG
    PPS_ALC_GR2       ..........  .GGTTGAGCT  CAGTCCACTA  GCTTATCGAG  CTGATCTAGT 101                                                  150
PPS_ALC_CDS_GR3       ......ATGG  GTAATTCCGA  CGAAGGTGGT  CGTCTTCCTG  CTCCATCTTC
 PPS_ALC_A1_GR3       AGAGAGATGG  GTAATTCCGA  CGAAGGTGGT  CGTCTTCCTG  CTCCATCTTC
PPS_ALC_CDS_GR4       ......ATGG  GTAATTCCGA  TGAAGGTGAT  CGTCTTCCTG  CTCCATCTTC
 PPS_ALC_C1_GR4       AGAGAGATGG  GTAATTCCGA  TGAAGGTGAT  CGTCTTCCTG  CTCCATCTTC
    PPS_ALC_GR1       TCGAAGATGG  GTAGTTCCCA  CCACAGTTTC  TG........  ...CCATCTTC
    PPS_ALC_GR6       TCGAAGATGG  GTAGTTCCGA  CGACAGTTTC  TG........  ...CCATCTTC
    PPS_ALC_GR5       AGAGAGATGG  GTAATTCCGA  CGCCAGAGAT  CGTCTTCCTG  CTCCATCTTC
    PPS_ALC_GR2       TTCAATGAGC  TTGTCCAACA  TACTGCTCGA  CCAGTTCCCC  AGCTCGCCTA 151                                                  200
PPS_ALC_CDS_GR3       TTCAGACGAA  CTCTCGAGCA  TTCTGCGG..  .......CAG  GTACTGTCCC
 PPS_ALC_A1_GR3       TTCAGACGAA  CTCTCGAGCA  TTCTGCGG..  .......CAG  GTACTGTCCC
PPS_ALC_CDS_GR4       TTCGGACGAA  CTCTCGAGCA  TTCTCCGG..  .......CAG  GTACTGTCCC
 PPS_ALC_C1_GR4       TTCGGACGAA  CTCTCGAGCA  TTCTCCGG..  .......CAG  GTACTGTCCC
    PPS_ALC_GR1       ATCCGACAAA  CTCTTTAGCA  TTCTCCGG..  .......CAA  ATTCTGTCAC
    PPS_ALC_GR6       ATCCGACAAA  CTCTCTAGCA  TTCTCCGG..  .......CAG  ATTCTGTCAC
    PPS_ALC_GR5       TTCAGACGAA  CTCTCGAGCA  TTCTCCGG..  .......CAG  GTACTTTCCC
    PPS_ALC_GR2       GCTCGTCCAG  CTCTTTACAC  TCTTCCTTAG  CTCGGTCCAG  CTTCTTTTCT 201                                                  250
PPS_ALC_CDS_GR3       GTACTCCC..  .ACAGCTCAA  CCTTCTTTCT  CACCGAAGAA  AA...TCGTT
 PPS_ALC_A1_GR3       GTACTCCC..  .ACAGCTCAA  CCTTCTTTCT  CACCGAAGAA  AA...TCGTT
PPS_ALC_CDS_GR4       GTACTCCC..  .ACAGCTCAA  CCTTCTTTCT  CACCGAAGAA  AA...TCGTT
 PPS_ALC_C1_GR4       GTACTCCC..  .ACAGCTCAA  CCTTCTTTCT  CACCGAAGAA  AA...TCGTT
    PPS_ALC_GR1       GTACTCCG..  .ACAACCCAA  CCTTCCCCAC  CCAAGAGAAA  CA......TT
    PPS_ALC_GR6       GTACTCCG..  .ACAACCCAA  CCTTCCCCAC  CCAAGAGAAA  CA......TT
    PPS_ALC_GR5       GTACTCCTCC  GACTGCTCAA  CCTTCTTTCT  CACGGAAGAA  AA...TCGTT
    PPS_ALC_GR2       TCGTTTTT..  .CTCCTTTTT  CTTGGCTAAA  TCCGGATCAT  TCCTAAGACT
```

Figure 1

```
                  251                                                    300
PPS_ALC_CDS_GR3   TCCTCCGCTG AGATGTTCAA CCGAACATTC CCCCTCG..T TCCCGGCGGA
 PPS_ALC_A1_GR3   TCCTCCGCTG AGATGTTCAA CCGAACATTC CCCCTCG..T TCCCGGCGGA
PPS_ALC_CDS_GR4   TCCTCCGCTG AGATGTTCAA CCGAACCTTC CCCCTCG..T TCCCGGCGGA
 PPS_ALC_C1_GR4   TCCTCCGCTG AGATGTTCAA CCGAACCTTC CCCCTCG..T TCCCGGCGGA
    PPS_ALC_GR1   TCATCCGCTG AGATGTTCGA CTGGAACTTT CCTTTCG..T TTTCGGCGGA
    PPS_ALC_GR6   TCCTCCGCTG AGATGTTTGA CTGAAACTTT CCTTTCGA.. TTTCAGTGGA
    PPS_ALC_GR5   TCCTCCGGTG AGATGTTCAA CCGAACGTTC CCTCTCG..T TCACGGCGGA
    PPS_ALC_GR2   TAACCTTTTG TTCAGACCAT GGAACGCTTG TCTTAAAGTT TTTCGACTGG 301                                                    350
PPS_ALC_CDS_GR3   GCGGTTTCTT ACGCCGCTTG TGCAGCCGCT GAAACTGGGG AAAGCAAATG
 PPS_ALC_A1_GR3   GCGGTTTCTT ACGCCGCTTG TGCAGCCGCT GAAACTGGGG AAAGCAAATG
PPS_ALC_CDS_GR4   GCGGTTTCTT ACGCCGCTTG TGCAGTCGCT GAAACTGGGG AAGGCAAATG
 PPS_ALC_C1_GR4   GCGGTTTCTT ACGCCGCTTG TGCAGTCGCT GAAACTGGGG AAGGCAAATG
    PPS_ALC_GR1   GCAGTTTCTA GCGCAGGCTA TGCGGTCATT GAAACTGGGG GAGACAAATG
    PPS_ALC_GR6   GCAGTTTCTA GCGCAGGCTA TGAGGTCATT GAAATTGGAG GAGACAAATG
    PPS_ALC_GR5   GCGGTTTCTT ACGCCGCTTG TGCAGTCTCT GAAACTGAGG AAGGAAAATG
    PPS_ALC_GR2   CTTGCACGTT CCCTCGTCCC ATGGCCCGTT CCAACGATCC TTAGCAAAGA 351                                                    400
PPS_ALC_CDS_GR3   TGGTTTCGAA AACAAG.... .......... .......... ..........
 PPS_ALC_A1_GR3   TGGTTTCGAA AACAAGGTAA ACTT...... .......... ..........
PPS_ALC_CDS_GR4   TGGTTTCGAA AACAAG.... .......... .......... ..........
 PPS_ALC_C1_GR4   TGGTTTCGAA AACAAGGTAA ACTT...... .......... ..........
    PPS_ALC_GR1   TGCTTTTGAG AACAAGGTAA AACTTAACAA CTTTATTGCT GTCGTCAAAT
    PPS_ALC_GR6   TGCTTTTGAG AACAAGGTAA AACGTGTTAA AA..AAAAGA ACAAGGTAAA
    PPS_ALC_GR5   TGCTTTCGAG AACCAGGTAA ACTT...... .......... ..........
    PPS_ALC_GR2   TCGGGGATGC TACAATTACA AATAGAATAG AAAGGGAG.. ..........

401                                                    450
PPS_ALC_CDS_GR3   .......... .......... .......... .......... ..........
 PPS_ALC_A1_GR3   .......... .......... .......... .......... ..........
PPS_ALC_CDS_GR4   .......... .......... .......... .......... ..........
 PPS_ALC_C1_GR4   .......... .......... .......... .......... ..........
    PPS_ALC_GR1   TATAATCGCT TTGTTTAAAG AAATACTAAA GAGAGCATCT CTCTCGTCTC
    PPS_ALC_GR6   ACTTAACAAC TTTAGTTGCT GTCGTCCAAT TTTTTTTTTT TGAATTAGCT
    PPS_ALC_GR5   .......... .......... .......... .......... ..........
    PPS_ALC_GR2   .......... .......... .......... .......... ..........

451                                                    500
PPS_ALC_CDS_GR3   .......... .......... .......... .......... ..........
 PPS_ALC_A1_GR3   .......... .......... .......... .......... ..........
PPS_ALC_CDS_GR4   .......... .......... .......... .......... ..........
 PPS_ALC_C1_GR4   .......... .......... .......... .......... ..........
    PPS_ALC_GR1   TCTCATCTTT TCTTGAAGTT TCCAGCTTTT GGATTTGCAG TCTCTGGCCA
    PPS_ALC_GR6   AGAGGTATCC TGACCCCACA GAAGTGATCC AGACTAGTCA TGTGTTGCCA
    PPS_ALC_GR5   .......... .......... .......... .......... ..........
    PPS_ALC_GR2   .......... .......... .......... .......... ..........
```

Figure 1, continued.

```
                    501                                                       550
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     ACGTCCGGTT  CGCCGGCGTT  GTGTCTTGTA  AATTTGTAAT  TAGTTTTTTT
    PPS_ALC_GR6     CATGTCGGTC  CTCTATCCCT  GGCAATGCTG  AAATGTTAAT  TCTCCAGTGG
    PPS_ALC_GR5     ..........  ..........  ..........  ..........  ..........
    PPS_ALC_GR2     ..........  ..........  ..........  ..........  ..........

551                                                       600
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     TTTGTTTTGT  CACCGACTTG  TTTGGGGTTT  GTCTCCGGTT  TTAATCCGGT
    PPS_ALC_GR6     CTGGGATTCG  AACCCAGCTG  TC........  ..........  ..........
    PPS_ALC_GR5     ..........  ..........  ..........  ..........  ..........
    PPS_ALC_GR2     ..........  ..........  ..........  ..........  ..........

601                                                       650
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     TTTGTTCTTC  CGTCTTGTAC  GGATCTTAAC  TCCGATTGGG  TTCGGTTTAT
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........

651                                                       700
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     CTTTTGTTTA  ATCGGCTTAA  AATCTCTAGC  CTTTGTGTGT  TCTAATCTCT
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........

701                                                       750
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     TTCTGGTTTT  CTCCAATCGA  TTGAACAGAT  TTGGGTTTTC  ACTAATGCTT
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........
```

Figure 1, continued.

```
                    751                                                  800
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     GACTCTTTGC  TCATGAGAAA  ATAAACCCTC  ACTTCTTGGC  TATGGCGATT
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........

801                                                  850
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     TAAAGTGCAG  GTCATCCATG  TGTGAAGATT  CAAGGTGTTG  CGATTATCCG
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........

851                                                  900
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     GAGAAGAGTG  AAGATTTAAA  ACTCTGGTCG  TGTTCAGACG  GTGTTTTAAA
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........

901                                                  950
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     GAATGCTCCA  ATCCGATTAA  CTGGGTTCTT  AACTCTTGGT  GTTTAAGTCT
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........

951                                                 1000
PPS_ALC_CDS_GR3     ..........  ..........  ..........  ..........  ..........
 PPS_ALC_A1_GR3     ..........  ..........  ..........  ..........  ..........
PPS_ALC_CDS_GR4     ..........  ..........  ..........  ..........  ..........
 PPS_ALC_C1_GR4     ..........  ..........  ..........  ..........  ..........
    PPS_ALC_GR1     AAATCTCAAC  AATCTTTTGG  GATAATCAAA  GCAAAGGCTT  CAAACGATGC
    PPS_ALC_GR6     ..........  ..........  ..........  ..........  ..........
    PPS_ALC_GR5     ..........  ..........  ..........  ..........  ..........
    PPS_ALC_GR2     ..........  ..........  ..........  ..........  ..........
```

Figure 1, continued.

```
                         1001                                                          1050
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
     PPS_ALC_GR1         AAATAAAAAA  ACTAAGCTTG  CTCACAACAA  AACGTTTGAT  CAAAAGAGAA
     PPS_ALC_GR6         ..........  ..........  ..........  ..........  ..........
     PPS_ALC_GR5         ..........  ..........  ..........  ..........  ..........
     PPS_ALC_GR2         ..........  ..........  ..........  ..........  ..........

1051                                                          1100
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
     PPS_ALC_GR1         AGCACTGTGG  TGGCTCAAGT  CTTCGGTGGA  GGTAGAAACC  TCTTCTGGTT
     PPS_ALC_GR6         ..........  ..........  ..........  ..........  ..........
     PPS_ALC_GR5         ..........  ..........  ..........  ..........  ..........
     PPS_ALC_GR2         ..........  ..........  ..........  ..........  ..........

1101                                                          1150
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
     PPS_ALC_GR1         CTCAGAGAAG  GTGCGTGTTT  GGCTTGGAAG  GAGATAGATG  TATATCGGAG
     PPS_ALC_GR6         ..........  ..........  ..........  ..........  ..........
     PPS_ALC_GR5         ..........  ..........  ..........  ..........  ..........
     PPS_ALC_GR2         ..........  ..........  ..........  ..........  ..........

1151                                                          1200
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
     PPS_ALC_GR1         CGATTGCTTC  ATTGTCGGTC  GATTGTCGCC  GTCTTGATCG  TGATTGTCAT
     PPS_ALC_GR6         ..........  ..........  ..........  ..........  ..........
     PPS_ALC_GR5         ..........  ..........  ..........  ..........  ..........
     PPS_ALC_GR2         ..........  ..........  ..........  ..........  ..........

1201                                                          1250
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
     PPS_ALC_GR1         GGATTTGGAG  TGGTTATTAT  CCAGCTACCG  GCTGTGTGAA  TAAGACGTTT
     PPS_ALC_GR6         ..........  ..........  ..........  ..........  ..........
     PPS_ALC_GR5         ..........  ..........  ..........  ..........  ..........
     PPS_ALC_GR2         ..........  ..........  ..........  ..........  ..........
```

Figure 1, continued.

```
                         1251                                                     1300
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
    PPS_ALC_GR1          CCGGGAAACC  TTTATAGGCT  TCGCCGTGGG  GTGATGGTGC  GTATGAGGCG
    PPS_ALC_GR6          ..........  ..........  ..........  ..........  ..........
    PPS_ALC_GR5          ..........  ..........  ..........  ..........  ..........
    PPS_ALC_GR2          ..........  ..........  ..........  ..........  ..........

1301                                                     1350
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
    PPS_ALC_GR1          CGGGGAGAGC  ACACTCAAGG  TCCAATGGAG  AGACTTAGTT  GGGATTGAAG
    PPS_ALC_GR6          ..........  ..........  ..........  ..........  ..........
    PPS_ALC_GR5          ..........  ..........  ..........  ..........  ..........
    PPS_ALC_GR2          ..........  ..........  ..........  ..........  ..........

1351                                                     1400
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
    PPS_ALC_GR1          GGTGTTTACA  GCGACGGTTA  AGGATTCTAA  CCTCTCTCGA  TTCAGTTTAT
    PPS_ALC_GR6          ..........  ..........  ..........  ..........  ..........
    PPS_ALC_GR5          ..........  ..........  ..........  ..........  ..........
    PPS_ALC_GR2          ..........  ..........  ..........  ..........  ..........

1401                                                     1450
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
    PPS_ALC_GR1          ATGTTTGGTG  ATGTTCGTGT  GCGTCTAGTC  TATCTCGATG  CTCCTCTCAT
    PPS_ALC_GR6          ..........  ..........  ..........  ..........  ..........
    PPS_ALC_GR5          ..........  ..........  ..........  ..........  ..........
    PPS_ALC_GR2          ..........  ..........  ..........  ..........  ..........

1451                                                     1500
PPS_ALC_CDS_GR3          ..........  ..........  ..........  ..........  ..........
 PPS_ALC_A1_GR3          ..........  ..........  ..........  ..........  ..........
PPS_ALC_CDS_GR4          ..........  ..........  ..........  ..........  ..........
 PPS_ALC_C1_GR4          ..........  ..........  ..........  ..........  ..........
    PPS_ALC_GR1          TTTGTGTTAA  TTGTTGATGA  GTTCTATTTC  GGTAAGCTCG  TCTTTGAGCG
    PPS_ALC_GR6          ..........  ..........  ..........  ..........  ..........
    PPS_ALC_GR5          ..........  ..........  ..........  ..........  ..........
    PPS_ALC_GR2          ..........  ..........  ..........  ..........  ..........
```

Figure 1, continued.

```
                 1501                                                    1550
PPS_ALC_CDS_GR3  ..........  ..........  ..........  ..........  ..........
PPS_ALC_A1_GR3   ..........  ..........  ..........  ..........  ..........
PPS_ALC_CDS_GR4  ..........  ..........  ..........  ..........  ..........
PPS_ALC_C1_GR4   ..........  ..........  ..........  ..........  ..........
   PPS_ALC_GR1   CAAGGTGGAG  CACTCCTCTA  CTGAAGTTCT  GTTTTACTCT  CATGCTTCTC
   PPS_ALC_GR6   ..........  ..........  ..........  ..........  ..........
   PPS_ALC_GR5   ..........  ..........  ..........  ..........  ..........
   PPS_ALC_GR2   .....ATATT  TATTGATTTT  CGAAGAAACA  CATATAAACA  TATAGAATTA 1551                                                    1600
PPS_ALC_CDS_GR3  ..........  ..........  ..........  ..........  ..........
PPS_ALC_A1_GR3   ..........  ..........  ..........  ..........  ..........
PPS_ALC_CDS_GR4  ..........  ..........  ..........  ..........  ..........
PPS_ALC_C1_GR4   ..........  ..........  ..........  ..........  ..........
   PPS_ALC_GR1   GACATCTTTT  TTCTTCGTGT  CTTTGTTAGT  TTTTTAAGGG  TTTGTGTTGT
   PPS_ALC_GR6   ..........  ..........  ..........  ..........  ..........
   PPS_ALC_GR5   ..........  ..........  ..........  ..........  ..........
   PPS_ALC_GR2   TTCTATTTGT  TATTATTGTA  TTTTTACATA  AGCAATAAAA  ATTTGATTGA 1601                                                    1650
PPS_ALC_CDS_GR3  ..........  ..........  ..........  ..........  ..........
PPS_ALC_A1_GR3   ..........  ..........  ..........  ..........  ..........
PPS_ALC_CDS_GR4  ..........  ..........  ..........  ..........  ..........
PPS_ALC_C1_GR4   ..........  ..........  ..........  ..........  ..........
   PPS_ALC_GR1   ATCCATCTTT  TGGCTCCGGG  TGGTAAATGT  TACCGCGCCG  GCTTATGGTT
   PPS_ALC_GR6   ..........  ..........  ..........  ..........  ..........
   PPS_ALC_GR5   ..........  ..........  ..........  ..........  ..........
   PPS_ALC_GR2   AAAACTAATA  GAGGCTAAGA  ATATTTATAT  CTCCATACCA  CCTCGAAGTC 1651                                                    1700
PPS_ALC_CDS_GR3  ..........  ..........  ..........  ..........  ..........
PPS_ALC_A1_GR3   ..........  ..........  ..........  ..........  ..........
PPS_ALC_CDS_GR4  ..........  ..........  ..........  ..........  ..........
PPS_ALC_C1_GR4   ..........  ..........  ..........  ..........  ..........
   PPS_ALC_GR1   TTGGAAGGAA  TGTATTCCTT  GCCGGCTCTG  GTTTGTAAGA  AATGTTGTTT
   PPS_ALC_GR6   ..........  ..........  ..........  ..........  ..........
   PPS_ALC_GR5   ..........  ..........  ..........  ..........  ..........
   PPS_ALC_GR2   CAAAATACTA  TTCAAAAGAT  CCAATAAATT  GCCGACAAAA  AAAAAGATCC 1701                                                    1750
PPS_ALC_CDS_GR3  ..........  ..........  ..........  ..........  ..........
PPS_ALC_A1_GR3   ..........  ....AACGAT  GTTAGTTGCC  GTGAAAGTAC  CCTCGCTT..
PPS_ALC_CDS_GR4  ..........  ..........  ..........  ..........  ..........
PPS_ALC_C1_GR4   ..........  ....AACGAT  GTTAGTTGCC  GTGAAACTAT  TACCCTCGCT
   PPS_ALC_GR1   TTGTGTTTAA  TATAATCTAC  AGATGACAAA  AAAAAAAAAA  AAATAACTAA
   PPS_ALC_GR6   ..........  ....GTCAAA  TTATAATCGG  TTGGTTTAAA  GAAATACTAA
   PPS_ALC_GR5   ..........  ....AACAAT  GTTAGTTGCC  GTGAAACTAC  ACTCGCTTTG
   PPS_ALC_GR2   AATAAATCAA  TGGTAACAAC  TTTTGTTGCC  GTTAAACTAC  ACTCGCTTTG
```

Figure 1, continued.

```
                      1751                                                1800
PPS_ALC_CDS_GR3       .......... .......... .......... .......... ..........
 PPS_ALC_A1_GR3       ..TTGATTAA A.GAAAAAAT AACTTAGTTG TTGTTTTTGC TTGGTAATGG
PPS_ALC_CDS_GR4       .......... .......... .......... .......... ..........
 PPS_ALC_C1_GR4       TGTTGATTAA AGAAAAAAAT AACTTTATTG TGTTTTTGGT TGGTAATGGT
    PPS_ALC_GR1       A.GAGAGAGA A.ATGGAGTC ACTAAAGAAC ACCATTTTTC TTTGTAATGG
    PPS_ALC_GR6       A.GAGAGAGA A.ATGGAGTC ACTAAAGAAC ACCATTTTTC TTTGAAATGG
    PPS_ALC_GR5       G.TTAAAGAA C.AAAAAAAA AACTTGTTGT TGTTTTTGCT TTGTAATGGT
    PPS_ALC_GR2       T.TTAAAGAA C.AAAAACAA AACTAACTTT TGTTTTTCTT TTGCAATGGT 1801                                                1850
PPS_ALC_CDS_GR3       .......... .......AGA AATGGAGCTA GACAGCGAAA TTCATTGAAG
 PPS_ALC_A1_GR3       TTAACACAAC ACTAAAGAGA AATGGAGCTA GACAGCGAAA TTCATTGAAG
PPS_ALC_CDS_GR4       .......... .......AGA AATGGAGCTA GACAGCGAAA TTCATTGAAG
 PPS_ALC_C1_GR4       TA..AAAAAC ACTAAAGAGA AATGGAGCTA GACAGCGAAA TTCATTGAAG
    PPS_ALC_GR1       TAACAATAAC ACTCAATAGA AATGGAGTCA GACAGCGAAA CTCGTTGAAG
    PPS_ALC_GR6       TAACAATAAA ACTCAATAGA AATGGAGTCA GACAGTAAAA CTTGTTGAAG
    PPS_ALC_GR5       AA..AACAAC ACTAAATAGA AATGGAGCTA GACAGCGAAA ..........
    PPS_ALC_GR2       AAC.AATAAC ACTAAAGAGA AACGGAGCCA GGTAGCGAAA CTCGTTGAAG 1851                                                1900
PPS_ALC_CDS_GR3       AGAAACATTG ATGCACAGTT CCACAACTTG TCTGAAAAG. ..........
 PPS_ALC_A1_GR3       AGAAACATTG ATGCACAGTT CCACAACTTG TCTGAAAAGG .TTTCGTCTT
PPS_ALC_CDS_GR4       AGAAACATTG ATGCACAGTT CCACACCTTG TCTGAAAAG. ..........
 PPS_ALC_C1_GR4       AGAAACATTG ATGCACAGTT CCACACCTTG TCTGAAAAGG .TTT.TGTCT
    PPS_ALC_GR1       AGAAACATTG ATACACAGTT CCACAACTTG TCTGAAAAGG .TTTCTGTCT
    PPS_ALC_GR6       AGAAACATTG ATACACAGTT CCACAACTTG TCTGAAAAGG .TTTCTGTCT
    PPS_ALC_GR5       .......TTG ATGCACAGTT CCACAACTTG TTTGAAAAGG .TTTCTGTCT
    PPS_ALC_GR2       AGAAACATTG ATGCACAGTT CCACAACTTG TCTGAAAAGG CTTCCGTCTT 1901                                                1950
PPS_ALC_CDS_GR3       .......... .......... .......... .......... ..........
 PPS_ALC_A1_GR3       TATCCTTTTA AGATTC.... ........TT GATTTGGTTT AAAA..AAAA
PPS_ALC_CDS_GR4       .......... .......... .......... .......... ..........
 PPS_ALC_C1_GR4       TTATCCTTTT AAGATTC... ........TT GATTTGGTTT AAAAAAAAAA
    PPS_ALC_GR1       TTTTCCTTTT AAATAT.... ........TC TTGATCTGTA AAAATTAAAA
    PPS_ALC_GR6       TTTTCCTTTT AAATAT.... ........TC ATGATCTGTA AAAATTAAAA
    PPS_ALC_GR5       TTATCCTTTT AACATTCTTT GAATTGATTT TTTTTTTAAA GAACTGGACA
    PPS_ALC_GR2       TCAGCTTTTT TAAATA.... ........TT CTTGATCTGA AAAATATATA 1951                                                2000
PPS_ALC_CDS_GR3       .......... .......... .......... ......AGGAG GAGGAGCAAG
 PPS_ALC_A1_GR3       CTAGAGATAA T.AATAGAAA CTGGATATAT TGCAGAGGAG GAGGAGCAAG
PPS_ALC_CDS_GR4       .......... .......... .......... ......AGGAG GAGGAGCAAG
 PPS_ALC_C1_GR4       CTAGAGATAA T.AATAGAAA CTGGATATAT TGCAGAGGAG GAGGAGCAAG
    PPS_ALC_GR1       ...AAATAAT A.AATAGAAT CCGAAAATAT TGCAGAGGAG AAGGAGCAAG
    PPS_ALC_GR6       ...AATTAAT A.AATAGATT CCGAAAATAT TTCAGAGGAG AAGGAGCAAG
    PPS_ALC_GR5       .TAATAATAG TTAATAGAAA CTGAAAGTAT TGCAGA.TAG GAGGAGCAAG
    PPS_ALC_GR2       .AAAAAACAA T.AATAGAAT CAGAAAATAT TGCAGAGAAG GAGGAGCAAG
```

Figure 1, continued.

```
                 2001                                                 2050
PPS_ALC_CDS_GR3  ATCAATGAGA AAATGAAAGC ATTGCAGAAA CTGATACC.. ..........
 PPS_ALC_A1_GR3  ATCAATGAGA AAATGAAAGC ATTGCAGAAA CTGATACC.. ..........
PPS_ALC_CDS_GR4  ATCAACGAGA AAATGAAAGC TTTGCAGAAA CTGATACC.. ..........
 PPS_ALC_C1_GR4  ATCAACGAGA AAATGAAAGC TTTGCAGAAA CTGATACC.. ..........
    PPS_ALC_GR1  ATCAACGAGA AAATGAAAGC TTTGCAGAAA ATGAAAGCTT TGCAGAAGCG
    PPS_ALC_GR6  ATCAACGAGA AAATGAAAGC TTTACAGAAG CTGATACT.. ..........
    PPS_ALC_GR5  ATCAACGAGA AAATTAAAGC TTTACAGAAA CTGATACC.. ..........
    PPS_ALC_GR2  ATCAACGAGA AAATGAAATC TTTGCAGAAG CTGATACC.. ..........

2051                                                 2100
PPS_ALC_CDS_GR3  ......CAAT TCCAACA... .......... .......... ..........
 PPS_ALC_A1_GR3  ......CAAT TCCAACAAGG T...AAATAT AAAGTTCGAC ATTTTATCC.
PPS_ALC_CDS_GR4  ......CAAT TCCAACA... .......... .......... ..........
 PPS_ALC_C1_GR4  ......CAAT TCCAACAAGG TGGTAAATAC CAAGTTCGAC TTTTTATCT.
    PPS_ALC_GR1  GATACTCAAT TCCAACAAGT T...AAATTG AATGTTCCAA TCTTTATAC.
    PPS_ALC_GR6  ......CAAT TCCAACAAGT T...AAATTG AATGTTCCAA TCTTTATAC.
    PPS_ALC_GR5  ......CAAT TCCAACAAGG T...ATATAG CAAGTTCGAC TTTTTATCCC
    PPS_ALC_GR2  ......CAAT TCCAACAAGG T...AAATTG AAAGTTTGAA TTTTCATCC.

2101                                                 2150
PPS_ALC_CDS_GR3  .......... .......... .......... .......... ..........
 PPS_ALC_A1_GR3  TTCAGAACTG AGTGTCGTGA AAAGC..... ..ATTTATTT TGTT..TTTT
PPS_ALC_CDS_GR4  .......... .......... .......... .......... ..........
 PPS_ALC_C1_GR4  TTCAGAACTC AGTTGTGAGA TACAT..... ..TTGTTTTG TTTT..TTTT
    PPS_ALC_GR1  TTCAGATCTC TATCTTGAGA ATGAG..... ..AAACATTG TTTT..TTTT
    PPS_ALC_GR6  TTCAGATCTC TATCTTGAGA ATGAG..... ..AAACATTG TTTTGTTTTT
    PPS_ALC_GR5  .TCAGAACTC AGTTGTGAGA AGCAT..... ..TTGTTTTG TTTT..TTAT
    PPS_ALC_GR2  TTCAGAACTT AGACATGATA AACATTCTTT TTATATATAT ATATATATAT 2151                                                 2200
PPS_ALC_CDS_GR3  .......... AGACAGATAA GGCCTCAATG CTT.GATGAA GCTATAGAAT
 PPS_ALC_A1_GR3  TATGTTTGGT AGACAGATAA GGCCTCAATG CTT.GATGAA GCTATAGAAT
PPS_ALC_CDS_GR4  .......... AGACAGAAAA GGCCTCAATG CTT.GATGAA GCTATAGAAT
 PPS_ALC_C1_GR4  TATGTTTTGT AGACAGAAAA GGCCTCAATG CTT.GATGAA GCTATAGAAT
    PPS_ALC_GR1  TTATAGTTGT AGACAGATAA AGTCTCCATG CTTTGATGAA GCAATAGAAT
    PPS_ALC_GR6  TAATAGTTGT AGACATATAA AGTCTCATTG CTTTGATGAA GCGATAAAAT
    PPS_ALC_GR5  ...GGTATGT AGACAGATAA GGCCTCAATG TTT.GATGAA ACTATAGAAT
    PPS_ALC_GR2  ATATATTTGT AGACAGATAA AGCCTCAATG CTT.GATGAA GCTATAGAAT 2201                                                 2250
PPS_ALC_CDS_GR3  ATCTGAAACA GCTTCAACTT CAGTTTCAG. .......... ..........
 PPS_ALC_A1_GR3  ATCTGAAACA GCTTCAACTT CAGTTTCAGG TTCTTTTTCT ATATGTTCCT
PPS_ALC_CDS_GR4  ATCTGAAACA GCTTCAACTT CAGTTTCAG. .......... ..........
 PPS_ALC_C1_GR4  ATCTGAAACA GCTTCAACTT CAGTTTCAGG TTCTTTTTCT ATATGTTCCT
    PPS_ALC_GR1  ATCTGAAGCT GCTTCAACTT CAAGTGCAGG TTTCTTACTA AAGATCATAT
    PPS_ALC_GR6  ATCTGACGCT GCTTCAACTT CAAGTGCAGG TTTCTTACTA AAGATCATAT
    PPS_ALC_GR5  ATTTGAAACA GCTTCAACTT CA.GTTTTCA ACTTTGGGTT TCGGGCAAGC
    PPS_ALC_GR2  ATCTGAAGCA GCTTCAACTT CAAGTGCAGG TTTTTATTT TATTTTATTT
```

Figure 1, continued.

```
                         2251                                                        2300
PPS_ALC_CDS_GR3          ..........  ..........  ..........  ..........  ..........
 PPS_ALC_A1_GR3          TACGCTATGA  TCATAAACAA  CTAAATTTGT  AAAACCAAAC  ATCTGATTAA
PPS_ALC_CDS_GR4          ..........  ..........  ..........  ..........  ..........
 PPS_ALC_C1_GR4          TACGCTATGA  TCATAAACAA  CTAAATTTGT  AAACCCAAAC  ATCTGATTAA
    PPS_ALC_GR1          ATAATCAAAG  TCTAATCTGT  AAAACATATC  ATCTGATTAA  CTTATTTACT
    PPS_ALC_GR6          ATAATCAAAG  TCTAATCTGT  AAAACATATC  ATCTGATTAA  CTTATTTACT
    PPS_ALC_GR5          GCACTAAGGG  GTTGATTGGT  AAGTGCTATC  ATTTCATTTT  TTGACTGT..
    PPS_ALC_GR2          TACTTACTAA  GATCCTTTAT  ATGCAATCAA  AGTTTAAATT  TGTAAACCCC 2301                                                        2350
PPS_ALC_CDS_GR3          ..........  ..........  ..........  ....ACGTTA  GCCGCTATGA
 PPS_ALC_A1_GR3          CTTTTAAT..  ..........  ......GACT  GCAGACGTTA  GCCGCTATGA
PPS_ALC_CDS_GR4          ..........  ..........  ..........  ....ACGTTA  GCCGCTATGA
 PPS_ALC_C1_GR4          CTTGAT....  ..........  ......GAAT  GCAGACGTTA  GCCGCTATGA
    PPS_ALC_GR1          CCA.......  ..........  ......TAAA  GCAGACTTTA  GCCGTTATGA
    PPS_ALC_GR6          CC..A.....  ..........  ......TAAT  GCAGACTTTA  GCCGTTATGA
    PPS_ALC_GR5          ..........  ..........  ........AG  AAATATTGCT  GTGGTTTTTA
    PPS_ALC_GR2          ATTGTCTGAT  TAACATAATC  ACTGCATAAT  ACAGACTTTA  GCTGTTATGA 2351                                                        2400
PPS_ALC_CDS_GR3          ATGGTTTAGG  CCTAAATCCT  CTGCGATTAC  CACCAATTCT  ACCGCCTACG
 PPS_ALC_A1_GR3          ATGGTTTAGG  CCTAAATCCT  CTGCGATTAC  CACCAATTCT  ACCGCCTACG
PPS_ALC_CDS_GR4          ATGGTTTAGG  CCTAAATCCT  CTGCGATTAC  CACCAATTCT  ACCGCCTACG
 PPS_ALC_C1_GR4          ATGGTTTAGG  CCTAAATCCT  CTGCGATTAC  CACCAATTCT  ACCGCCTACG
    PPS_ALC_GR1          ATGGTCTAGG  CCTAAACCCT  CAGCGACTAC  CACCAGTTCT  ACCGCCTACG
    PPS_ALC_GR6          ATGGTCTAGG  CCTAAACCCT  CAGCGACTAC  CACCAGTTCT  ACCGCCTACG
    PPS_ALC_GR5          TTGCTTTGGC  TTTAGATTTT  TAATTTTTAA  AAGTCTTTAA  ATATGGGCTG
    PPS_ALC_GR2          ATGGTTTAGG  CCTAAACTCT  ATGCGACTAC  CACCAGTTCT  ACCGTCTACG 2401                                                        2450
PPS_ALC_CDS_GR3          CAGACAAGGA  TCAC.TGGAA  CCTCTGAACA  AGGGCTGAAC  CTTGAGACTC
 PPS_ALC_A1_GR3          CAGACAAGGA  TCAC.TGGAA  CCTCTGAACA  AGGGCTGAAC  CTTGAGACTC
PPS_ALC_CDS_GR4          CAGACAGGGA  TCAC.TGGAA  CCTCAGAACA  AGGGCTGAAC  CTTGAGACTC
 PPS_ALC_C1_GR4          CAGACAGGGA  TCAC.TGGAA  CCTCAGAACA  AGGGCTGAAC  CTTGAGACTC
    PPS_ALC_GR1          CAGACAAGGA  TCAA.TGGAA  CCTTAGAACA  AGACCTCAAC  TTTGGGACTC
    PPS_ALC_GR6          CAGACAAGGA  TCAA.TGGAA  CCTTAGAACA  AGACCTCAAC  TTTGGGACTC
    PPS_ALC_GR5          TAGGTTTTTG  TCTCTGCAGA  GAAATTGTAA  AGACATAATT  TCAAAGAAGT
    PPS_ALC_GR2          CAGACAAGGT  TCAAATGGAA  CCTTACAACA  AGAGCAGCAC  TTTGGGACTC 2451                                                        2500
PPS_ALC_CDS_GR3          TGCTTGGTGG  TTCTCACTCG  ATGGCTAACC  A.TGAACCAC  CCG..AACCA
 PPS_ALC_A1_GR3          TGCTTGGTGG  TTCTCACTCG  ATGGCTAACC  A.TGAACCAC  CCG..AACCA
PPS_ALC_CDS_GR4          TGCTTGGTGG  TTCTCACTCG  ATGGCTAACC  T.TGAACCAC  CCG..AACCA
 PPS_ALC_C1_GR4          TGCTTGGTGG  TTCTCACTCG  ATGGCTAACC  T.TGAACCAC  CCG..AACCA
    PPS_ALC_GR1          TGCTTGGTGC  TTCTCACTCG  CTGGTTAACC  G.TGAACCAC  CCG..AATCA
    PPS_ALC_GR6          TGCTTGGTGC  TTCTCACTCG  CTGGTTAACC  GGTGAACCAC  CTG..AATCA
    PPS_ALC_GR5          GCTGTGGATT  TTATAAAAAG  ACTGTGAACT  T.AAAAAAAA  ATAGAAATCA
    PPS_ALC_GR2          GGCTTGGTGC  TCCTCACTCG  ATGGTTAACC  G.TGAACCAC  CCC..AAGCA
```

Figure 1, continued.

```
                    2501                                                    2550
PPS_ALC_CDS_GR3     ACTCAGG... AAATGTGCTT TTCCACAACC ACTCTGCTTT GA........
 PPS_ALC_A1_GR3     ACTCAGG... AAATGTGCTT TTCCACAACC ACTCTGCTTT GAAGACAACG
PPS_ALC_CDS_GR4     ACTCAGG... AAATGTGCTT TCCCACAACC ACTCTGCTTT GA........
 PPS_ALC_C1_GR4     ACTCAGG... AAATGTGCTT TCCCACAACC ACTCTGCTTT GAAGACAACG
    PPS_ALC_GR1     ACTCAGG... AAATGTGCTT TTCCACAGAC ACTCTGCTTT GAAGACAACA
    PPS_ALC_GR6     ACTCAGG... AAATGTGCTT TTCCACAGAC ACTCTGCTTT GAAGACAACA
    PPS_ALC_GR5     AGATTGGTGT AGATTTAGTG TTCTAGAAAG AAATGAGGCT GTAGAGAGCA
    PPS_ALC_GR2     ACTCAGG... AAATGTGCTT TTCCACAGGC ACGCTGCTTT GAAGACAAAG 2551                                                    2600
PPS_ALC_CDS_GR3     .......... .......... .......... .......... ..........
 PPS_ALC_A1_GR3     TTCAAAGAGT GAAGAGGATT CGAAGTCAGA TTTCCTCTCT CCACAGAAAC
PPS_ALC_CDS_GR4     .......... .......... .......... .......... ..........
 PPS_ALC_C1_GR4     TTCAGACAGT GAAGAGGATT CGAAGTCAGA TTTCCTCTCC ACAGAAACAT
    PPS_ALC_GR1     TTCAGACGTG AAGATGATTC GAAGTCAAGA TCTCCTCTGA GTACCGTATA
    PPS_ALC_GR6     TTCGGACGTG AAGATGATTC GAAGTCAAGA TCTCCTCTTA GTACCGTATA
    PPS_ALC_GR5     CTCATCACTA CCAATCACAC CCTAAAAAGA GTTATGTTCC CTAATAAGAA
    PPS_ALC_GR2     ATGATTCGAA GTCAACATCT CCGGCTTAGT ACACTACCAA ACAGTAGTCA 2601                                          2642
PPS_ALC_CDS_GR3     .......... .......... .......... .......... ..
 PPS_ALC_A1_GR3     ATGAGCCGAA AATGATTTGT AGAGTCTAGT ATTTGGTTAT AT
PPS_ALC_CDS_GR4     .......... .......... .......... .......... ..
 PPS_ALC_C1_GR4     GAGCCGAAAA TGATTTGGTT ATATTTCAAA GTGTTATGCT AA
    PPS_ALC_GR1     CCACAAATGG CTGGGCACAA GGCGAGTACT CGTTATTTT. ..
    PPS_ALC_GR6     CCACAAAGAG CTTGTGAGCT TTGGTCTTCA TCAGTTGGGC TG
    PPS_ALC_GR5     AAAAGGAAAG CGGTTACGCG TAAAAT.... .......... ..
    PPS_ALC_GR2     AAACTGTTTT TAGTCTAGTA TTTGCATACT CCAAAGTTCA GT
```

Figure 1, continued.

SEQUENCE LISTING

<160> NUMBER OF SEQ ID NOS: 61

<210> SEQ ID NO 1
<211> LENGTH: 2547
<212> TYPE: DNA
<213> ORGANISM: Brassica napus

<400> SEQUENCE: 1

```
acgaaaacca ccatcgtccg attcatcatc cgtcaacttt ggcccactgg gtttggacac        60
aagtgcgtcg tactgcggct gttccagttt aatgtcgaag tcgaagatgg gtagttccca       120
ccacagtttc tgccatcttc atccgacaaa ctctttagca ttctccggca aattctgtca       180
cgtactccga caacccaacc ttccccaccc aagagaaaca tttcatccgc tgagatgttc       240
gactggaact ttcctttcgt tttcggcgga gcagtttcta gcgcaggcta tgcggtcatt       300
gaaactgggg gagacaaatg tgcttttgag aacaaggtaa aacttaacaa ctttattgct       360
gtcgtcaaat tataatcgct ttgtttaaag aaatactaaa gagagcatct ctctcgtctc       420
tctcatcttt tcttgaagtt tccagctttt ggatttgcag tctctggcca acgtccggtt       480
cgccggcgtt gtgtcttgta aatttgtaat tagtttttttt tttgttttgt caccgacttg       540 tttgggqttt gtctccggtt ttaatccggt tttgttcttc cgtcttgtac ggatcttaac       600
tccgattggg ttcggtttat cttttgttta atcggcttaa aatctctagc ctttgtgtgt       660
tctaatctct ttctggtttt ctccaatcga ttgaacagat ttgggttttc actaatgctt       720
gactctttgc tcatgagaaa ataaaccctc acttcttggc tatggcgatt taaagtgcag       780
gtcatccatg tgtgaagatt caaggtgttg cgattatccg gagaagagtg aagatttaaa       840
actctggtcg tgttcagacg gtgttttaaa gaatgctcca atccgattaa ctgggttctt       900
aactcttggt gtttaagtct aaatctcaac aatcttttgg gataatcaaa gcaaaggctt       960
caaacgatgc aaataaaaaa actaagcttg ctcacaacaa aacgtttgat caaaagagaa      1020
agcactgtgg tggctcaagt cttcggtgga ggtagaaacc tcttctggtt ctcagagaag      1080
gtgcgtgttt ggcttggaag gagatagatg tatatcggag cgattgcttc attgtcggtc      1140
gattgtcgcc gtcttgatcg tgattgtcat ggatttggag tggttattat ccagctaccg      1200
gctgtgtgaa taagacgttt ccgggaaacc tttataggct tcgccgtggg gtgatggtgc      1260
gtatgaggcg cggggagagc acactcaagg tccaatggag agacttagtt gggattgaag      1320
```

```
ggtgtttaca gcgacggtta aggattctaa cctctctcga ttcagtttat atgtttggtg    1380
atgttcgtgt gcgtctagtc tatctcgatg ctcctctcat tttgtgttaa ttgttgatga    1440
gttctatttc ggtaagctcg tctttgagcg caaggtggag cactcctcta ctgaagttct    1500
gttttactct catgcttctc gacatctttt ttcttcgtgt ctttgttagt tttttaaggg    1560
tttgtgttgt atccatcttt tggctccggg tggtaaatgt taccgcgccg gcttatggtt    1620
ttggaaggaa tgtattcctt gccggctctg gtttgtaaga atgttgtttt ttgtgtttaa    1680
tataatctac agatgacaaa aaaaaaaaaa aaataactaa agagagagaa atggagtcac    1740
taaagaacac cattttttctt tgtaatggta acaataacac tcaatagaaa tggagtcaga    1800
cagcgaaact cgttgaagag aaacattgat acacagttcc acaacttgtc tgaaaaggtt    1860
tctgtctttt tccttttaaa tattcttgat ctgtaaaaat taaaaaaata ataaatagaa    1920
tccgaaaata ttgcagagga gaaggagcaa gatcaacgag aaaatgaaag ctttgcagaa    1980
aatgaaagct tgcagaagc ggatactcaa ttccaacaag ttaaattgaa tgttccaatc    2040
tttatacttc agatctctat cttgagaatg agaaacattg tttttttttt atagttgtag    2100
acagataaag tctccatgct tgatgaagc aatagaatat ctgaagctgc ttcaacttca    2160
agtgcaggtt tcttactaaa gatcatatat aatcaaagtc taatctgtaa aacatatcat    2220
ctgattaact tatttactcc ataaagcaga ctttagccgt tatgaatggt ctaggcctaa    2280
accctcagcg actaccacca gttctaccgc ctacgcagac aaggatcaat ggaaccttag    2340
aacaagacct caactttggg actctgcttg gtgcttctca ctcgctggtt aaccgtgaac    2400
cacccgaatc aactcaggaa atgtgctttt ccacagacac tctgctttga agacaacatt    2460
cagacgtgaa gatgattcga agtcaagatc tcctctgagt accgtatacc acaaatggct    2520
gggcacaagg cgagtactcg ttatttt                                        2547
```

<210> SEQ ID NO 2
<211> LENGTH: 1415
<212> TYPE: DNA
<213> ORGANISM: Brassica napus

<400> SEQUENCE: 2

```
ggttgagctc agtccactag cttatcgagc tgatctagtt tcaatgagct tgtccaacat      60
actgctcgac cagttcccca gctcgcctag ctcgtccagc tctttacact cttccttagc     120
tcggtccagc ttcttttctt cgttttctc cttttcttg gctaaatccg gatcattcct       180
aagacttaac cttttgttca gaccatggaa cgcttgtctt aaagttttc gactggcttg      240 cacgttccct cgtcccatgg cccgttccaa cgatccttag caaagatcgg ggatgctaca     300
attacaaata gaatagaaag ggagatattt attgattttc gaagaaacac atataaacat     360
atagaattat tctatttgtt attattgtat tttacataa gcaataaaaa tttgattgaa      420
aaactaatag aggctaagaa tatttatatc tccataccac ctcgaagtcc aaaatactat     480
tcaaaagatc caataaattg ccgacaaaaa aaaagatcca ataaatcaat ggtaacaact     540
tttgttgccg ttaaactaca ctcgctttgt ttaaagaaca aaaacaaaac taactttttgt    600 ttttcttttg caatggtaac aataacacta agagaaacg gagccaggta gcgaaactcg      660
ttgaagagaa acattgatgc acagttccac aacttgtctg aaaaggcttc cgtctttcag     720
cttttttaaa tattcttgat ctgaaaaata tataaaaaaa caataataga atcagaaaat     780
attgcagaga aggaggagca agatcaacga gaaaatgaaa tctttgcaga agctgatacc     840
```

| | |
|---|---|
| caattccaac aaggtaaatt gaaagtttga attttcatcc ttcagaactt agacatgata | 900 |
| aacattcttt ttatatatat atatatatat atatatttgt agacagataa agcctcaatg | 960 |
| cttgatgaag ctatagaata tctgaagcag cttcaacttc aagtgcaggt tttttatttt | 1020 |
| atttatttt acttactaag atcctttata tgcaatcaaa gtttaaattt gtaaacccca | 1080 |
| ttgtctgatt aacataatca ctgcataata cagactttag ctgttatgaa tggtttaggc | 1140 |
| ctaaactcta tgcgactacc accagttcta ccgtctacgc agacaaggtt caaatggaac | 1200 |
| cttacaacaa gagcagcact ttgggactcg gcttggtgct cctcactcga tggttaaccg | 1260 |
| tgaaccaccc caagcaactc aggaaatgtg cttttccaca ggcacgctgc tttgaagaca | 1320 |
| aagatgattc gaagtcaaca tctccggctt agtacactac caaacagtag tcaaaactgt | 1380 |
| ttttagtcta gtatttgcat actccaaagt tcagt | 1415 |

<210> SEQ ID NO 3
<211> LENGTH: 1201
<212> TYPE: DNA
<213> ORGANISM: Brassica napus
<220> FEATURE:
<221> NAME/KEY: variation
<222> LOCATION: (668)..(668)
<223> OTHER INFORMATION: G to A in ALC-GR3-EMS07

<400> SEQUENCE: 3

| | |
|---|---|
| gattatggct agagtgattt gccacgcgcc tgcctattta ttatgaaaag cctcagtaac | 60 |
| tctgtgacga gaagaattca cagagagaga gaggagagag atgggtaatt ccgacgaagg | 120 |
| tggtcgtctt cctgctccat cttcttcaga cgaactctcg agcattctgc ggcaggtact | 180 |
| gtcccgtact cccacagctc aaccttcttt ctcaccgaag aaaatcgttt cctccgctga | 240 |
| gatgttcaac cgaacattcc ccctcgttcc cggcggagcg gtttcttacg ccgcttgtgc | 300 |
| agccgctgaa actggggaaa gcaaatgtgg tttcgaaaac aaggtaaact aacgatgtt | 360 |
| agttgccgtg aaagtaccct cgcttttgat taaagaaaaa ataacttagt tgttgttttt | 420 |
| gcttggtaat ggttaacaca acactaaaga gaaatggagc tagacagcga aattcattga | 480 |
| agagaaacat tgatgcacag ttccacaact tgtctgaaaa ggtttcgtct ttatcctttt | 540 |
| aagattcttg atttggttta aaaaaaacta gagataataa tagaaactgg atatattgca | 600 |
| gaggaggagg agcaagatca atgagaaaat gaaagcattg cagaaactga tacccaattc | 660 |
| caacaaggta aatataaagt tcgacatttt atccttcaga actgagtgtc gtgaaaagca | 720 |
| tttattttgt ttttttatgt ttggtagaca gataaggcct caatgcttga tgaagctata | 780 |
| gaatatctga aacagcttca acttcagttt caggttcttt ttctatatgt tccttacgct | 840 |
| atgatcataa acaactaaat ttgtaaaacc aaacatctga ttaactttta atgactgcag | 900 |
| acgttagccg ctatgaatgg tttaggccta atcctctgc gattaccacc aattctaccg | 960 |
| cctacgcaga caaggatcac tggaacctct gaacaagggc tgaaccttga gactctgctt | 1020 |
| ggtggttctc actcgatggc taaccatgaa ccacccgaac caactcagga aatgtgcttt | 1080 |
| tccacaacca ctctgctttg aagacaacgt tcaaagagtg aagaggattc gaagtcagat | 1140 |
| ttcctctctc cacagaaaca tgagccgaaa atgatttgta gagtctagta tttggttata | 1200 |
| t | 1201 |

<210> SEQ ID NO 4
<211> LENGTH: 1207
<212> TYPE: DNA
<213> ORGANISM: Brassica napus

```
<220> FEATURE:
<221> NAME/KEY: variation
<222> LOCATION: (646)..(646)
<223> OTHER INFORMATION: C to T in ALC-GR4-EMS04

<400> SEQUENCE: 4
ccagattatg tctagagtga tttgccacgc gcctgcctat ttattatgaa aagcctcagt      60
aacttgtgat gagaagaatt cacagagaga gaggagagag atgggtaatt ccgatgaagg     120
tgatcgtctt cctgctccat cttcttcgga cgaactctcg agcattctcc ggcaggtact     180
gtcccgtact cccacagctc aaccttcttt ctcaccgaag aaaatcgttt cctccgctga     240
gatgttcaac cgaaccttcc ccctcgttcc cggcggagcg gtttcttacg ccgcttgtgc     300
agtcgctgaa actggggaag gcaaatgtgg tttcgaaaac aaggtaaact taacgatgtt     360
agttgccgtg aaactattac cctcgcttgt tgattaaaga aaaaaataac tttattgtgt     420
ttttggttgg taatggttaa aaaacactaa agagaaatgg agctagacag cgaaattcat     480
tgaagagaaa cattgatgca cagttccaca ccttgtctga aaaggttttg tctttatcct     540
tttaagattc ttgatttggt ttaaaaaaaa aactagagat aataatagaa actggatata     600
ttgcagagga ggaggagcaa gatcaacgag aaaatgaaag ctttgcagaa actgataccc     660
aattccaaca aggtggtaaa taccaagttc gacttttat cttcagaac tcagttgtga       720
gatacatttg ttttgttttt tttatgtttt tgtagacaga aaaggcctca atgcttgatg     780
aagctataga atatctgaaa cagcttcaac ttcagtttca ggttcttttt ctatatgttc     840
cttacgctat gatcataaac aactaaattt gtaaacccaa acatctgatt aacttgatga     900
atgcagacgt tagccgctat gaatggttta ggcctaaatc ctctgcgatt accaccaatt     960
ctaccgccta cgcagacagg gatcactgga acctcagaac aagggctgaa ccttgagact    1020
ctgcttggtg gttctcactc gatggctaac cttgaaccac ccgaaccaac tcaggaaatg    1080
tgctttccca caaccactct gctttgaaga caacgttcag acagtgaaga ggattcgaag    1140
tcagatttcc tctccacaga aacatgagcc gaaaatgatt tggttatatt tcaaagtgtt    1200
atgctaa                                                              1207

<210> SEQ ID NO 5
<211> LENGTH: 1174
<212> TYPE: DNA
<213> ORGANISM: Brassica napus

<400> SEQUENCE: 5
gctcataaat cacgcgcgta cttccccacc tatttattat gaaaagcctc agtaaactag      60
taaagtgaat tgtgaaggat tacagagaga cagagagaga tgggtaattc cgacgccaga     120
gatcgtcttc ctgctccatc ttcttcagac gaactctcga gcattctccg gcaggtactt     180
tcccgtactc ctccgactgc tcaaccttct ttctcacgga gaaaatcgtt tcctccggt      240
gagatgttca accgaacgtt ccctctcgtt cacggcggag cggtttctta cgccgcttgt     300
gcagtctctg aaactgagga aggaaaatgt gctttcgaga accaggtaaa cttaacaatg     360
ttagttgccg tgaaactaca ctcgcttttgg ttaaagaaca aaaaaaaaac ttgttgttgt     420
ttttgctttg taatggtaaa acaacactaa atagaaatgg agctagacag cgaaattgat     480
gcacagttcc acaacttgtt tgaaaaggtt tctgtcttta tccttttaac attctttgaa     540
ttgattttt ttttaaagaa ctggacataa taatagttaa tagaaactga agtattgca        600
gataggagga gcaagatcaa cgagaaaatt aaagctttac agaaactgat acccaattcc     660
```

| | | |
|---|---|---|
| aacaaggtat atagcaagtt cgactttta tccctcagaa ctcagttgtg agaagcattt | 720 | |
| gttttgtttt ttatggtatg tagacagata aggcctcaat gtttgatgaa actatagaat | 780 | |
| atttgaaaca gcttcaactt cagttttcaa ctttgggttt cgggcaagcg cactaagggg | 840 | |
| ttgattggta agtgctatca tttcattttt tgactgtaga aatattgctg tggttttat | 900 | |
| tgctttggct ttagattttt aattttaaa agtctttaaa tatgggctgt aggttttgt | 960 | |
| ctctgcagag aaattgtaaa gacataattt caaagaagtg ctgtggattt tataaaaga | 1020 | |
| ctgtgaactt aaaaaaaat agaaatcaag attggtgtag atttagtgtt ctagaaagaa | 1080 | |
| atgaggctgt agagagcact catcactacc aatcacaccc taaaaagagt tatgttccct | 1140 | |
| aataagaaaa aaggaaagcg gttacgcgta aaat | 1174 | |

<210> SEQ ID NO 6
<211> LENGTH: 1360
<212> TYPE: DNA
<213> ORGANISM: Brassica napus

<400> SEQUENCE: 6

| | | |
|---|---|---|
| ccccaagcct cctcatgccg tctggacaca agtgcgtcgt actgtggctg ttccagttta | 60 | |
| atgtcgaagt cgaagatggg tagttccgac gacagtttct gccatcttca tccgacaaac | 120 | |
| tctctagcat tctccggcag attctgtcac gtactccgac aacccaacct tccccaccca | 180 | |
| agagaaacat ttcctccgct gagatgtttg actgaaactt tcctttcgat tcagtggag | 240 | |
| cagtttctag cgcaggctat gaggtcattg aaattggagg agacaaatgt gcttttgaga | 300 | |
| acaaggtaaa acgtgttaaa aaaagaacaa aggtaaaact taacaacttt agttgctgtc | 360 | |
| gtccaatttt ttttttttga attagctaga ggtatcctga ccccacagaa gtgatccaga | 420 | |
| ctagtcatgt gttgccacat gtcggtcctc tatccctggc aatgctgaaa tgttaattct | 480 | |
| ccagtggctg ggattcgaac ccagctgtcg tcaaattata atcggttggt ttaaagaaat | 540 | |
| actaaagaga gagaaatgga gtcactaaag aacaccattt ttctttgaaa tggtaacaat | 600 | |
| aaaactcaat agaaatggag tcagacagta aacttgttg aagagaaaca ttgatacaca | 660 | |
| gttccacaac ttgtctgaaa aggtttctgt ctttttcctt ttaaatattc atgatctgta | 720 | |
| aaaattaaaa aattaataaa tagattccga aaatatttca gaggagaagg agcaagatca | 780 | |
| acgagaaaat gaaagcttta cagaagctga tactcaattc caacaagtta aattgaatgt | 840 | |
| tccaatcttt atacttcaga tctctatctt gagaatgaga acattgttt tgttttttaa | 900 | |
| tagttgtaga catataaagt ctcattgctt tgatgaagcg ataaaatatc tgacgctgct | 960 | |
| tcaacttcaa gtgcaggttt cttactaaag atcatatata atcaaagtct aatctgtaaa | 1020 | |
| acatatcatc tgattaactt atttactcca taatgcagac tttagccgtt atgaatggtc | 1080 | |
| taggcctaaa ccctcagcga ctaccaccag ttctaccgcc tacgcagaca aggatcaatg | 1140 | |
| gaaccttaga acaagacctc aactttggga ctctgcttgg tgcttctcac tcgctggtta | 1200 | |
| accggtgaac cacctgaatc aactcaggaa atgtgctttt ccacagacac tctgctttga | 1260 | |
| agacaacatt cggacgtgaa gatgattcga agtcaagatc tcctcttagt accgtatacc | 1320 | |
| acaaagagct tgtgagcttt ggtcttcatc agttgggctg | 1360 | |

<210> SEQ ID NO 7
<211> LENGTH: 648
<212> TYPE: DNA
<213> ORGANISM: Brassica napus

<400> SEQUENCE: 7

```
atgggtaatt ccgacgaagg tggtcgtctt cctgctccat cttcttcaga cgaactctcg      60
agcattctgc ggcaggtact gtcccgtact cccacagctc aaccttcttt ctcaccgaag     120
aaaatcgttt cctccgctga gatgttcaac cgaacattcc ccctcgttcc cggcggagcg     180
gtttcttacg ccgcttgtgc agccgctgaa actggggaaa gcaaatgtgg tttcgaaaac     240
aagagaaatg gagctagaca gcgaaattca ttgaagagaa acattgatgc acagttccac     300
aacttgtctg aaaagaggag gaggagcaag atcaatgaga aaatgaaagc attgcagaaa     360
ctgataccca attccaacaa gacagataag gcctcaatgc ttgatgaagc tatagaatat     420
ctgaaacagc ttcaacttca gtttcagacg ttagccgcta tgaatggttt aggcctaaat     480
cctctgcgat taccaccaat tctaccgcct acgcagacaa ggatcactgg aacctctgaa     540
caagggctga accttgagac tctgcttggt ggttctcact cgatggctaa ccatgaacca     600
cccgaaccaa ctcaggaaat gtgctttttcc acaaccactc tgctttga                648
```

<210> SEQ ID NO 8
<211> LENGTH: 648
<212> TYPE: DNA
<213> ORGANISM: Brassica napus

<400> SEQUENCE: 8

```
atgggtaatt ccgatgaagg tgatcgtctt cctgctccat cttcttcgga cgaactctcg      60
agcattctcc ggcaggtact gtcccgtact cccacagctc aaccttcttt ctcaccgaag     120
aaaatcgttt cctccgctga gatgttcaac cgaaccttcc ccctcgttcc cggcggagcg     180
gtttcttacg ccgcttgtgc agtcgctgaa actggggaag gcaaatgtgg tttcgaaaac     240
aagagaaatg gagctagaca gcgaaattca ttgaagagaa acattgatgc acagttccac     300
accttgtctg aaaagaggag gaggagcaag atcaacgaga aaatgaaagc tttgcagaaa     360
ctgataccca attccaacaa gacagaaaag gcctcaatgc ttgatgaagc tatagaatat     420
ctgaaacagc ttcaacttca gtttcagacg ttagccgcta tgaatggttt aggcctaaat     480
cctctgcgat taccaccaat tctaccgcct acgcagacag ggatcactgg aacctcagaa     540
caagggctga accttgagac tctgcttggt ggttctcact cgatggctaa ccttgaacca     600
cccgaaccaa ctcaggaaat gtgctttccc acaaccactc tgctttga                 648
```

<210> SEQ ID NO 9
<211> LENGTH: 215
<212> TYPE: PRT
<213> ORGANISM: Brassica napus
<220> FEATURE:
<221> NAME/KEY: bHLH domain
<222> LOCATION: (91)..(142)
<220> FEATURE:
<221> NAME/KEY: bHLH domain
<222> LOCATION: (92)..(142)

<400> SEQUENCE: 9

Met Gly Asn Ser Asp Glu Gly Gly Arg Leu Pro Ala Pro Ser Ser Ser
1               5                   10                  15

Asp Glu Leu Ser Ser Ile Leu Arg Gln Val Leu Ser Arg Thr Pro Thr
            20                  25                  30

Ala Gln Pro Ser Phe Ser Pro Lys Lys Ile Val Ser Ser Ala Glu Met
        35                  40                  45

Phe Asn Arg Thr Phe Pro Leu Val Pro Gly Gly Ala Val Ser Tyr Ala
    50                  55                  60

```
Ala Cys Ala Ala Ala Glu Thr Gly Glu Ser Lys Cys Gly Phe Glu Asn
 65                  70                  75                  80

Lys Arg Asn Gly Ala Arg Gln Arg Asn Ser Leu Lys Arg Asn Ile Asp
                 85                  90                  95

Ala Gln Phe His Asn Leu Ser Glu Lys Arg Arg Arg Ser Lys Ile Asn
                100                 105                 110

Glu Lys Met Lys Ala Leu Gln Lys Leu Ile Pro Asn Ser Asn Lys Thr
            115                 120                 125

Asp Lys Ala Ser Met Leu Asp Glu Ala Ile Glu Tyr Leu Lys Gln Leu
130                 135                 140

Gln Leu Gln Phe Gln Thr Leu Ala Ala Met Asn Gly Leu Gly Leu Asn
145                 150                 155                 160

Pro Leu Arg Leu Pro Pro Ile Leu Pro Pro Thr Gln Thr Arg Ile Thr
                165                 170                 175

Gly Thr Ser Glu Gln Gly Leu Asn Leu Glu Thr Leu Leu Gly Gly Ser
                180                 185                 190

His Ser Met Ala Asn His Glu Pro Pro Glu Pro Thr Gln Glu Met Cys
            195                 200                 205

Phe Ser Thr Thr Thr Leu Leu
            210             215

<210> SEQ ID NO 10
<211> LENGTH: 215
<212> TYPE: PRT
<213> ORGANISM: Brassica napus
<220> FEATURE:
<221> NAME/KEY: bHLH domain
<222> LOCATION: (92)..(142)

<400> SEQUENCE: 10

Met Gly Asn Ser Asp Glu Gly Asp Arg Leu Pro Ala Pro Ser Ser Ser
 1               5                  10                  15

Asp Glu Leu Ser Ser Ile Leu Arg Gln Val Leu Ser Arg Thr Pro Thr
                 20                  25                  30

Ala Gln Pro Ser Phe Ser Pro Lys Lys Ile Val Ser Ala Glu Met
                 35                  40                  45

Phe Asn Arg Thr Phe Pro Leu Val Pro Gly Gly Ala Val Ser Tyr Ala
 50                  55                  60

Ala Cys Ala Val Ala Glu Thr Gly Glu Gly Lys Cys Gly Phe Glu Asn
 65                  70                  75                  80

Lys Arg Asn Gly Ala Arg Gln Arg Asn Ser Leu Lys Arg Asn Ile Asp
                 85                  90                  95

Ala Gln Phe His Thr Leu Ser Glu Lys Arg Arg Arg Ser Lys Ile Asn
                100                 105                 110

Glu Lys Met Lys Ala Leu Gln Lys Leu Ile Pro Asn Ser Asn Lys Thr
            115                 120                 125

Glu Lys Ala Ser Met Leu Asp Glu Ala Ile Glu Tyr Leu Lys Gln Leu
130                 135                 140

Gln Leu Gln Phe Gln Thr Leu Ala Ala Met Asn Gly Leu Gly Leu Asn
145                 150                 155                 160

Pro Leu Arg Leu Pro Pro Ile Leu Pro Pro Thr Gln Thr Gly Ile Thr
                165                 170                 175

Gly Thr Ser Glu Gln Gly Leu Asn Leu Glu Thr Leu Leu Gly Gly Ser
                180                 185                 190

His Ser Met Ala Asn Leu Glu Pro Pro Glu Pro Thr Gln Glu Met Cys
            195                 200                 205
```

```
Phe Pro Thr Thr Thr Leu Leu
    210                 215
```

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
aggaggagga gcaagatcaa tg                                    22

<210> SEQ ID NO 12
<211> LENGTH: 26
<212> TYPE: DNA
<213> ORGANISM: Artificial
<220> FEATURE:
<223> OTHER INFORMATION: primer

<400> SEQUENCE: 12
aacaaaataa atgcttttca cgacac                                26

<210> SEQ ID NO 13
<211> LENGTH: 24
<212> TYPE: DNA
<213> ORGANISM: Artificial
<220> FEATURE:
<223> OTHER INFORMATION: probe

<400> SEQUENCE: 13
tcgaacttta tatttatctt gttg                                  24

<210> SEQ ID NO 14
<211> LENGTH: 23
<212> TYPE: DNA
<213> ORGANISM: Artificial
<220> FEATURE:
<223> OTHER INFORMATION: probe

<400> SEQUENCE: 14
cgaactttat atttatcttg ttg                                   23

<210> SEQ ID NO 15
<211> LENGTH: 23
<212> TYPE: DNA
<213> ORGANISM: Artificial
<220> FEATURE:
<223> OTHER INFORMATION: probe

<400> SEQUENCE: 15
tgtcgaactt tatatttacc ttg                                   23

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
agaggaggag gagcaagatc aac                                   23

<210> SEQ ID NO 17
<211> LENGTH: 30

```
<212> TYPE: DNA
<213> ORGANISM: Artificial
<220> FEATURE:
<223> OTHER INFORMATION: primer

<400> SEQUENCE: 17
aaagataaaa agtcgaactt ggtatttacc                              30

<210> SEQ ID NO 18
<211> LENGTH: 16
<212> TYPE: DNA
<213> ORGANISM: Artificial
<220> FEATURE:
<223> OTHER INFORMATION: probe

<400> SEQUENCE: 18
agctttgtag aaactg                                             16

<210> SEQ ID NO 19
<211> LENGTH: 16
<212> TYPE: DNA
<213> ORGANISM: Artificial
<220> FEATURE:
<223> OTHER INFORMATION: probe

<400> SEQUENCE: 19
aaagctttgc agaaac                                             16

<210> SEQ ID NO 20
<211> LENGTH: 508
<212> TYPE: DNA
<213> ORGANISM: Brassica napus

<400> SEQUENCE: 20
agatgggtaa ttccgatgaa ggtgatcgtc ttcctgctcc atcttcttcg gacgaactct    60
cgagcattct ccggcaggta ctgtcccgta ctcccacagc tcaaccttct ttctcaccga   120
agaaaatcgt ttcctccgct gagatgttca accgaacctt ccccctcgtt cccggcggag   180
cggtttctta cgccgcttgt gcagtcgctg aaactgggga aggcaaatgt ggtttcgaaa   240
acaaggtaaa cttaacgatg ttagttgccg tgaaactacc ctcgcttgtt gattaaagaa   300
aaaaataact ttattgtgtt tttggttggt aatggttaaa aaacactaaa gagaaatgga   360
gctagacagc gaaattcatt gaagagaaac attgatgcac agttccacac cttgtctgaa   420
aaggttttgt ctttatcctt ttaagattct tgatttggtt taaaaaaaaa actagagata   480
ataatagaaa ctggatatat tgcagagg                                     508

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
aaatcaagaa tcttaaaagg ataaagacg                               29

<210> SEQ ID NO 22
<211> LENGTH: 26
<212> TYPE: DNA
<213> ORGANISM: Artificial Sequence
<220> FEATURE:
<223> OTHER INFORMATION: Primer
```

```
<400> SEQUENCE: 22
aacaaaataa atgctttca cgacag                                    26

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
aagacgaaac cttttcagac aagttg                                   26

<210> SEQ ID NO 24
<211> LENGTH: 20
<212> TYPE: DNA
<213> ORGANISM: Artificial Sequence
<220> FEATURE:
<223> OTHER INFORMATION: VIC probe

<400> SEQUENCE: 24
aagagaaaca ttgatgcaca                                          20

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
aagataaaaa gtcgaacttg gtatttacc                                29

<210> SEQ ID NO 26
<211> LENGTH: 20
<212> TYPE: DNA
<213> ORGANISM: Artificial Sequence
<220> FEATURE:
<223> OTHER INFORMATION: FAM probe

<400> SEQUENCE: 26
aagctttcat tttcttgttg                                          20

<210> SEQ ID NO 27
<211> LENGTH: 17
<212> TYPE: DNA
<213> ORGANISM: Artificial Sequence
<220> FEATURE:
<223> OTHER INFORMATION: VIC probe

<400> SEQUENCE: 27
aatgcttgat gaagcta                                             17

<210> SEQ ID NO 28
<211> LENGTH: 16
<212> TYPE: DNA
<213> ORGANISM: Artificial Sequence
<220> FEATURE:
<223> OTHER INFORMATION: VIC probe

<400> SEQUENCE: 28
acaagttgtg gaactg                                              16

<210> SEQ ID NO 29
<211> LENGTH: 18
```

<212> TYPE: DNA
<213> ORGANISM: Artificial Sequence
<220> FEATURE:
<223> OTHER INFORMATION: VIC probe

<400> SEQUENCE: 29
agaaaatgaa agcattgc                                                    18

<210> SEQ ID NO 30
<211> LENGTH: 20
<212> TYPE: DNA
<213> ORGANISM: Artificial Sequence
<220> FEATURE:
<223> OTHER INFORMATION: FAM probe

<400> SEQUENCE: 30
agaaaatgaa agtattgcag                                                  20

<210> SEQ ID NO 31
<211> LENGTH: 20
<212> TYPE: DNA
<213> ORGANISM: Artificial Sequence
<220> FEATURE:
<223> OTHER INFORMATION: FAM probe

<400> SEQUENCE: 31
agaaaatgaa agttttgcag                                                  20

<210> SEQ ID NO 32
<211> LENGTH: 19
<212> TYPE: DNA
<213> ORGANISM: Artificial Sequence
<220> FEATURE:
<223> OTHER INFORMATION: FAM probe

<400> SEQUENCE: 32
agaaactgat actcaattc                                                   19

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
agataaaaag tcgaacttgg tatttaccac                                       30

<210> SEQ ID NO 34
<211> LENGTH: 17
<212> TYPE: DNA
<213> ORGANISM: Artificial Sequence
<220> FEATURE:
<223> OTHER INFORMATION: FAM probe

<400> SEQUENCE: 34
agcttcatca agtattg                                                     17

<210> SEQ ID NO 35
<211> LENGTH: 19
<212> TYPE: DNA
<213> ORGANISM: Artificial Sequence
<220> FEATURE:
<223> OTHER INFORMATION: FAM probe

<400> SEQUENCE: 35
aggccttttc tgtttacaa                                              19

<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36
attcatcaag ttaatcagat gtttggg                                     27

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
caaatcaaga atcttaaaag gataaagacg                                  30

<210> SEQ ID NO 38
<211> LENGTH: 17
<212> TYPE: DNA
<213> ORGANISM: Artificial Sequence
<220> FEATURE:
<223> OTHER INFORMATION: FAM probe

<400> SEQUENCE: 38
caagttgtag aactgtg                                                17

<210> SEQ ID NO 39
<211> LENGTH: 18
<212> TYPE: DNA
<213> ORGANISM: Artificial Sequence
<220> FEATURE:
<223> OTHER INFORMATION: FAM probe

<400> SEQUENCE: 39
caatgcttga taaagcta                                               18

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
cacaccttgt ctgaaaaggt tttg                                        24

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
cagtcattaa aagttaatca gatgtttggt                                  30

<210> SEQ ID NO 42
<211> LENGTH: 18
<212> TYPE: DNA
<213> ORGANISM: Artificial Sequence

```
<220> FEATURE:
<223> OTHER INFORMATION: VIC probe

<400> SEQUENCE: 42 cctttctgt ctacaaaa                                                  18

<210> SEQ ID NO 43
<211> LENGTH: 32
<212> TYPE: DNA
<213> ORGANISM: Artificial Sequence
<220> FEATURE:
<223> OTHER INFORMATION: Primer

<400> SEQUENCE: 43
ctgaaggata aaatgtcgaa ctttatattt ac                                 32

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
cttcagaact gagtgtcgtg aaaag                                         25

<210> SEQ ID NO 45
<211> LENGTH: 16
<212> TYPE: DNA
<213> ORGANISM: Artificial Sequence
<220> FEATURE:
<223> OTHER INFORMATION: FAM probe

<400> SEQUENCE: 45
cttcagtttc aagttc                                                   16

<210> SEQ ID NO 46
<211> LENGTH: 19
<212> TYPE: DNA
<213> ORGANISM: Artificial Sequence
<220> FEATURE:
<223> OTHER INFORMATION: VIC probe

<400> SEQUENCE: 46
tagcttcatc aagcattga                                                19

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
tcatcaagtt aatcagatgt ttggg                                         25

<210> SEQ ID NO 48
<211> LENGTH: 14
<212> TYPE: DNA
<213> ORGANISM: Artificial Sequence
<220> FEATURE:
<223> OTHER INFORMATION: VIC probe

<400> SEQUENCE: 48
tgatacccaa ttcc                                                     14
```

```
<210> SEQ ID NO 49
<211> LENGTH: 18
<212> TYPE: DNA
<213> ORGANISM: Artificial Sequence
<220> FEATURE:
<223> OTHER INFORMATION: FAM probe

<400> SEQUENCE: 49
tgatgcacag ttcaacaa                                           18

<210> SEQ ID NO 50
<211> LENGTH: 16
<212> TYPE: DNA
<213> ORGANISM: Artificial Sequence
<220> FEATURE:
<223> OTHER INFORMATION: VIC probe

<400> SEQUENCE: 50
tgcacagttc gacaac                                             16

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
tgcttggtaa tggttaacac aacac                                   25

<210> SEQ ID NO 52
<211> LENGTH: 15
<212> TYPE: DNA
<213> ORGANISM: Artificial Sequence
<220> FEATURE:
<223> OTHER INFORMATION: FAM probe

<400> SEQUENCE: 52
tggtagacaa ataag                                              15

<210> SEQ ID NO 53
<211> LENGTH: 18
<212> TYPE: DNA
<213> ORGANISM: Artificial Sequence
<220> FEATURE:
<223> OTHER INFORMATION: VIC probe

<400> SEQUENCE: 53
tgtttggtag acagataa                                           18

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
tgtttttgct tggtaatggt taacac                                  26

<210> SEQ ID NO 55
<211> LENGTH: 28
<212> TYPE: DNA
<213> ORGANISM: Artificial Sequence
<220> FEATURE:
<223> OTHER INFORMATION: Primer
```

```
<400> SEQUENCE: 55
ttcagaactc agttgtgaga tacatttg                                    28

<210> SEQ ID NO 56
<211> LENGTH: 17
<212> TYPE: DNA
<213> ORGANISM: Artificial Sequence
<220> FEATURE:
<223> OTHER INFORMATION: VIC probe

<400> SEQUENCE: 56
ttcagtttca ggttctt                                                17

<210> SEQ ID NO 57
<211> LENGTH: 17
<212> TYPE: DNA
<213> ORGANISM: Artificial Sequence
<220> FEATURE:
<223> OTHER INFORMATION: VIC probe

<400> SEQUENCE: 57
ttggtagaca gataagg                                                17

<210> SEQ ID NO 58
<211> LENGTH: 17
<212> TYPE: DNA
<213> ORGANISM: Artificial Sequence
<220> FEATURE:
<223> OTHER INFORMATION: FAM probe

<400> SEQUENCE: 58
tttggtagac aaataag                                                17

<210> SEQ ID NO 59
<211> LENGTH: 16
<212> TYPE: DNA
<213> ORGANISM: Artificial Sequence
<220> FEATURE:
<223> OTHER INFORMATION: VIC probe

<400> SEQUENCE: 59
aaaatgaaag ctttgc                                                 16

<210> SEQ ID NO 60
<211> LENGTH: 19
<212> TYPE: DNA
<213> ORGANISM: Artificial Sequence
<220> FEATURE:
<223> OTHER INFORMATION: FAM probe

<400> SEQUENCE: 60
aaacattgat gtacagttc                                              19

<210> SEQ ID NO 61
<211> LENGTH: 20
<212> TYPE: DNA
<213> ORGANISM: Artificial Sequence
<220> FEATURE:
<223> OTHER INFORMATION: VIC probe

<400> SEQUENCE: 61
aagctttcat tttctcgttg                                             20
```

BRASSICA PLANT COMPRISING A MUTANT ALCATRAZ ALLELE

CROSS-REFERENCE TO RELATED APPLICATIONS

This application is a § 371 U.S. National Stage of International Application No. PCT/EP2011/073135, filed Dec. 16, 2011, which claims the benefit of European Patent Application Serial No. 10075765.7, filed Dec. 24, 2010 and U.S. Patent Application Ser. No. 61/429,594 filed Jan. 4, 2011, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "bcs10-2017-wo1 seqlist.txt", created on May 23, 2013, and having a size of 21,000 bytes and is filed concurrently with the specification. The sequence listing contained in this ASCII formatted document is part of the specification and is herein incorporated by reference in its entirety.

FIELD OF THE INVENTION

This invention relates to the field of agricultural products, especially crop plants, particularly of the Brassicaceae family, in particular *Brassica* species, of which the fruit dehiscence properties are modulated. More specifically the invention relates to improved methods and means for reducing seed shattering, or delaying seed shattering until after harvest, in plants such as Brassicaceae plants, particularly Brassicaceae plants grown for seed production, while maintaining at the same time an agronomically relevant threshability of the pods. Provided are both wild type and mutant nucleic acid molecules encoding *Brassica* ALCATRAZ proteins (ALC) and the proteins as such. Also provided are *Brassica* plants comprising at least one ALC gene, and cells, parts, seeds and progeny thereof, characterized in that all ALC genes in their genome are full knock-out alc alleles, whereby the fruit dehiscence properties are significantly altered. In addition, methods for generating *Brassica* plants in which seed shattering is reduced, or in which seed shattering is delayed until after harvest, while an agronomically relevant threshability of the pods is preferably maintained, are provided herein, as are seed pods and seeds obtainable from such plants. Further provided are detection tools (kits) and methods for detecting the presence of one or more mutant alc and/or wild type ALC alleles in biological samples.

BACKGROUND OF THE INVENTION

Siliques or pods from *Brassica* plants release their seeds through a process called fruit dehiscence. A silique consists of two carpels joined margin to margin. The suture between the margins forms a thick rib, called replum. As pod maturity approaches, the two valves separate progressively from the replum, along designated lines of weakness in the pod, eventually resulting in the shattering of the seeds that were attached to the replum. The dehiscence zone defines the exact location of the valve dissociation.

Shedding of seed (also referred to as "seed shatter" or "pod shatter") by mature pods before or during crop harvest is a universal phenomenon with crops that develop dry dehiscent fruits. Premature seed shatter results in a reduced seed recovery, which represents a problem in crops that are grown primarily for the seeds, such as oil-producing *Brassica* plants, particularly oilseed rape. Another problem related to premature seed shattering is an increase in volunteer growth in the subsequent crop year. In oilseed rape, pod shatter-related yield losses are on average 20% (Child et al., 1998, J Exp Bot 49: 829-838), but can reach up to 50%, depending on the weather conditions (MacLeod, 1981, Harvesting in Oilseed Rape, pp. 107-120 Cambridge Agricultural Publishing, Cambridge).

Current commercial oilseed rape varieties are extremely susceptible to shattering. There is little variation for resistance to shattering within existing breeding programs of *B. napus* but resistant lines have been found within the diploid parents of *B. napus* (*B. oleracea* and *B. rapa*) as well as within other members of the *Brassica* genus, notably *B. juncea*, *B. carinata* and *B. nigra*. Kadkol et al. (1986, Aust. J. Botany 34 (5): 595-601) report increased resistance towards shattering in certain accessions of *B. campestris* that was associated with the absence of a separation layer in the region of attachment of the siliqua valves to the replum. Prakash and Chopra (1988, Plant breeding 101: 167-168) describe the introgression of resistance to shattering in *Brassica napus* from *Brassica juncea* through non-homologous recombination. Spence et al. (1996, J of Microscopy 181: 195-203) describe that some lines of *Brassica juncea* show a reduced tendency to shatter as compared to *Brassica napus* lines. Morgan et al., 1998 (Fields Crop Research 58, 153-165) describe genetic variation for pod shatter resistance among lines of oilseed rape developed from synthetic *B. napus* and conclude that lines which required much energy to open their pods appeared to have increased vascularisation in the dehiscence zone and to have reduced cell wall degradation within the dehiscence zone. They further found a significant negative correlation between the length of the pod beak and the force needed to cause pod shattering. Child and Huttly (1999, Proc 10th Int. Rapeseed Congress) describe variation in pod maturation in an irradiation-induced mutant *B. napus* and a population of its parent cultivar, Jet Neuf, wherein the most resistant wild-type and mutant plants showed much lignification of groups of cells throughout the dehiscence zone and wherein vascular traces situated close to the inner edge of the dehiscence zone in the mutant were described to help to secure the valves. Child et al. (2003, J Exp Botany 54 (389): 1919-1930) further describe the association between increased pod shatter resistance and changes in the vascular structure in pods of a resynthesized *Brassica napus* line. However, the traditional methods for breeding have been unsuccessful in introducing shatter resistance into rape cultivars, without interference with other desirable traits such as early flowering, maturity and blackleg resistance (Prakash and Chopra, 1990, Genetical Research 56: 1-2).

Several genes, which promote or inhibit pod dehiscence, have been identified in *Arabidopsis thaliana* through mutant analysis: Combined mutants in both SHATTERPROOF1 (SHP1; initially referred to as AGL1) and SHATTERPROOF2 (SHP2; initially referred to as AGL5) result in indehiscent siliques (i.e. siliques which remain closed upon maturity in *Arabidopsis thaliana*) (Liljegren et al., 2000, Nature 404, 766-770). Similarly, mutants in the INDEHISCENT gene (referred to as IND1) in *Arabidopsis thaliana* (Liljegren et al., 2004, Cell 116: 843-853; PCT publication WO 01/79517), as well as in ALCATRAZ (referred to as ALC; Rajani et al. 2001, Current Biology 11, 1914-1922)

interfered with pod dehiscence leading to pod shatter resistance. Constitutive expression of FRUITFUL (FUL), a repressor of SHP and IND, in *Arabidopsis thaliana* also resulted in indehiscent siliques (Ferrandiz et al., 2000, Science, 289, 436-438). FILAMENTOUS FLOWER (FIL) and YABBY3 (YAB3), two YABBY-family transcription factors (Sawa et al., 1999, Genes Dev 13, 1079-1088; Siegfried et al., 1999, Development 126, 4117-4128), and JAGGED (JAG), a C2H2 zinc-finger transcription factor (Dinneny et al., 2004, Development 131, 1101-1110; Ohno et al., 2004, Development 131, 1111-1122), were identified to redundantly contribute to proper valve and valve margin development by promoting the expression of FUL and SHP in a region-specific manner (Dinneny et al., 2005, Development 132, 4687-4696). Genes for a number of hydrolytic enzymes, such as endopolygalacturonases, which play a role, during pod dehiscence, in the programmed breakdown of the dehiscence zone in pods from *Brassica* plants have also been identified (see e.g. WO 97/13865; Petersen et al., Plant. Mol. Biol., 1996, 31:517-527).

WO99/00503, WO01/79517 and WO0159122 describe downregulation of the expression of the *Arabidopsis* ALC, IND, AGL1 and AGL5 genes and orthologs thereof using gene-silencing techniques (such as antisense suppression or cosuppression) and mutagenesis.

WO 2010/006732, describes that the fruit dehiscence properties in *Brassica* plants can be controlled by controlling the number of IND genes/alleles that are "functionally expressed" in seed pods, i.e. that result in functional (biologically active) IND protein. By combining a number of full knock-out mutant IND alleles, while maintaining a minimal number of wild type IND alleles, resulting in a minimal level of functional IND protein, the dehiscence properties of the seed pods can be modified, more specifically pod shatter resistance can be increased and seed shattering can be reduced, or seed shattering can be delayed until after harvest, while maintaining at the same time an agronomically relevant threshability of the pods, such that the pods may still be opened along the dehiscence zone by applying limited physical forces.

Rajani et al. (2001, Current Biology 11, 1914-1922) describe a recessive mutant in the *Arabidopsis* ALCATRAZ gene, that disrupts the process of silique dehiscence. ALC encodes a myc/bHLH protein. Both lignification and external appearance of the dehiscence zone remains unchanged in the alc mutant. ALC plays a role in cell separation during fruit dehiscence by promoting the differentiation of a cell layer that is the site of separation between the valves and the replum within the dehiscence zone.

WO2001/059121 and WO2001/059122 also describe an *Arabidopsis* mutant, SGT10166, having siliques with an indehiscent phenotype. The gene disrupted in this mutant encodes a bHLH protein, and is identical to the ALCATRAZ gene as described by Rajani et al. (2001, Current Biology 11, 1914-1922). Expression of a dominant negative version of the SGT10166 protein (which is identical to the ALCATRAZ protein) delays dehiscence.

Hua et al. (2009, Planta 230: 493-503) cloned and sequenced two ALCATRAZ genes from *Brassica napus*, BnaC.ALC.a and BnaA.ALC.a. Both genes complement the alc mutation of *Arabidopsis thaliana*. Southern blot hybridization of *Brassica napus* ALC genes gave rise to three hybridized bands, indicating multiple copies of the ALC homologs in the genome of *Brassica napus*. Only expression of BnaC.ALC.a, but not of BnaA.ALC.a was detectable in the silique tissue of *Brassica napus*. The result indicates that the 5' flanking sequence of BnaC.ALC.a, not of BnaA.ALC.a could be used to drive antisense or RNAi structures of the gene in the genetic engineering project for anti-pod-shattering agronomic trait. Based on these results, it would be likely that downregulation of BnaA.ALC.a would be sufficient to obtain a podshatter resistant phenotype in *Brassica napus*.

It is important to realize that while seed shattering constitutes an important problem in oilseed rape culture, which may be solved by developing pod shatter resistant lines, ultimately, separation of the seeds from the pods is still required. In normal agricultural practice this is achieved by threshing of the pods by a combine harvester. Threshing of the pods by a combine harvester must be complete and must cause minimum damage to the seeds thus released. However, as pod strength increases, the more severe action required to thresh them causes an unacceptable level of damage to the seed. The pods of pod shatter resistant Brassicaceae plants should thus not be so strong that they cannot be threshed in a combine harvester (Bruce et al. 2001, J. Agric. Engng Res. 80, 343-350).

The prior art shows that, in order to obtain podshatter resistance in *Brassica*, while maintaining agronomically relevant threshability, the extent to which the genes involved in podshatter resistance have to be modulated, may be subtle (WO 2004/113542, WO 2010/006732).

In order to use the ALCATRAZ gene for podshatter resistance while retaining agronomically relevant threshability, a need remains for knowing all ALCATRAZ genes sequences in the *Brassica* genome. The isolation of mutant alleles corresponding to alc in economically important Brassicaceae plants, such as oilseed rape, is a laborious and time consuming task. Moreover, such isolation may be complicated by the amphidiploidy in oilseed rape and the consequent functional redundancy of the corresponding genes. Although Hua et al. (2009, Planta 230: 493-503) did not detect expression BnaA.ALC.a in the silique tissue of *Brassica napus*, and thus it is likely that there would be no need to modify BnaA.ALC.a in order to obtain podshatter resistance, a need remains for knowing how, and how many of the *Brassica* ALCATRAZ genes have to be modified in order to obtain podshatter resistance with agronomically relevant threshability.

These and other objects are achieved by the present invention, as indicated by the various embodiments described in the summary of the invention, figures, detailed description, examples and claims.

SUMMARY OF THE INVENTION

The inventors have found that the fruit dehiscence properties in *Brassica* plants can be controlled by knocking-out all ALC genes encoding a functional ALC protein. More specifically, pod shatter resistance can be increased and seed shattering can be reduced, or seed shattering can be delayed until after harvest, while maintaining at the same time an agronomically relevant threshability of the pods, such that the pods may still be opened along the dehiscence zone by applying limited physical forces.

Thus, in a first aspect, the present invention provides a *Brassica* plant comprising at least one ALC gene (and parts thereof, such as seed pods and seeds), characterized in that all ALC genes are full knock-out ALC genes in its genome, and wherein the pod shatter resistance of the plant is significantly increased compared to the pod shatter resistance of a plant comprising functional ALC genes, but wherein the plant preferably maintains an agronomically relevant threshability of the pods. As used herein, "plant part" includes any part derived from a plant of the invention, including plant parts such as cells, tissues, organs, seeds, seed pods, seed meal, seed cake, seed fats or oils. In a further aspect, the invention relates to *Brassica* plants comprising at least one non-naturally occurring full knock-out ALC gene, and wherein the pod shatter resistance of the plant is significantly increased compared to the pod shatter resistance of a plant comprising functional ALC genes.

In another aspect, the invention relates to *Brassica* plants with significantly reduced seed shattering which is obtained by a method comprising downregulation of ALC gene expression.

In another aspect, the invention provides (isolated) nucleic acid sequences encoding wild type and/or mutant ALC proteins, and methods of using these nucleic acid sequences to modify the fruit dehiscence properties of plants.

In a further aspect, the invention relates to seed pods with modified shatter resistance, which can be obtained from a plant according to the present invention, and the use of said seed pods, for example for planting and growing progeny from the plants.

In yet another aspect of the invention, methods are provided for identifying alc alleles or plants or plant parts comprising such alleles and for combining a suitable number of alc alleles and/or different types of alc alleles in a single plant, whereby the fruit dehiscence properties of this plant are significantly modified.

BRIEF DESCRIPTION OF THE DRAWINGS

FIG. 1: Sequence alignment of the identified ALC sequences identified in the genome of *Brassica napus* PPS_ALC_GR1 (SEQ ID NO:1), PPS_ALC_GR2 (SEQ ID NO:2), PPS_ALC_A1_GR3 (SEQ ID NO:3), PPS_ALC_C1_GR4 (SEQ ID NO:4), PPS_ALC_GR5 (SEQ ID NO:5), PPS_ALC_GR6 (SEQ ID NO:6), and the predicted coding sequences ALC PPS_ALC_CDS_GR3 (SEQ ID NO:7) and PPS_ALC_CDS_GR4 (SEQ ID NO:8).

GENERAL DEFINITIONS

Figure 2:
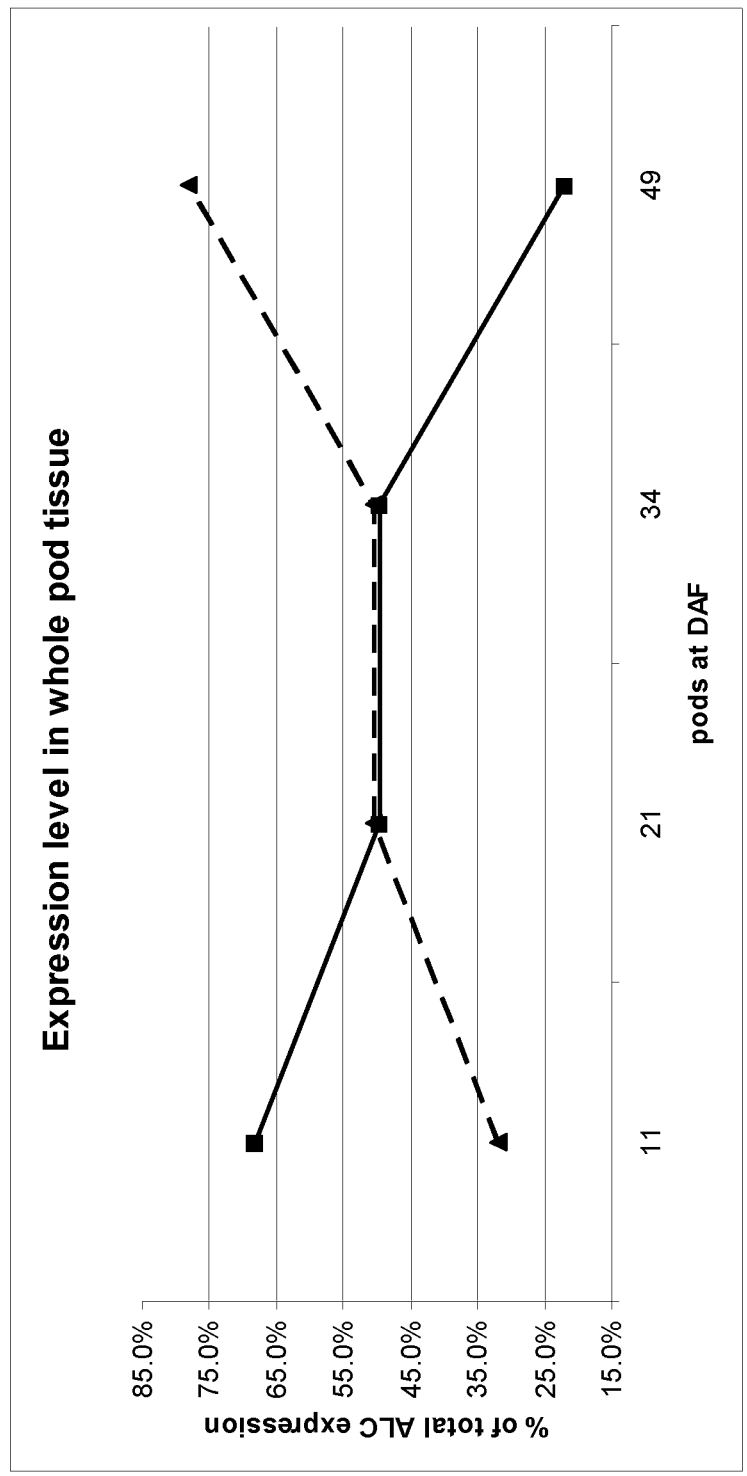
FIG. 2: Relative expression of Bn_ALC_GR3 and Bn_ALC_GR4 in whole pod tissue. Squares and black line: ALC-GR3; triangles and dashed lines: ALC-GR4.

"Increase of pod shatter resistance" and "reduction of seed shattering", as used herein, refers to a decreased seed shatter tendency and/or a delay in the timing of seed shattering, in particular until after harvest, of *Brassica* plants, the fruits of which normally do not mature synchronously, but sequentially, so that some pods burst open and shatter their seeds before or during harvest. The level of resistance to pod shattering is positively correlated with and can, for example, be measured by determining the force needed to break pods in the 'tensile separation test' (Davies and Bruce, 1997, J Mat Sci 32: 5895-5899; Morgan et al., 1998, Fields Crop Research 58, 153-165), the number of intact pods remaining after e.g. 20 sec ('IP20'; Morgan et al., 1998, Fields Crop Research 58, 153-165), 9.7 or 17 sec (Bruce et al., 2002, Biosystems Eng 81(2): 179-184) in a 'random impact test', the pod sample half-life ('LD50') in a random impact test, i.e. the treatment time needed to cause the opening of 50% of the pods in tested pod samples, and the 'field score for shattering' (Morgan et al., 1998, Fields Crop Research 58, 153-165). Random impact tests (RITs) and algorithms to define the pod sample half-lives in such RITs have been described in Bruce et al. 2001, J. Agric. Engng Res. 80, 343-350, Morgan et al., 1998, Fields Crop Research 58, 153-165, and the Examples below. Both publications are hereby incorporated by reference. Briefly, a sample of intact mature pods is placed in a closed drum together with steel balls and the drum is then vigorously agitated for increasing periods of times (e.g. 10 s, 20 s, 40 s, 80 s). After each period, the drum is opened and the number of broken and damaged pods is counted. The most accurate estimation of the level of shattering resistance for each line is calculated by fitting a linear x linear curve to all the available data and estimating the time taken for half of the pods within a sample to be broken ("pod sample half-life" or "LD50"). It is important however that pods open mainly along the dehiscence zone, and are not simply pulverized, as may occur with indehiscent pods.

An "agronomically relevant increase of pod shatter resistance", as used herein, refers to an increase of pod shatter resistance in a plant which results in pod shatter-related yield losses in the field (pre-harvest) below those normally observed for that plant in the field. For oilseed rape, pod shatter-related yield losses in the field are reported to be about 11% for a season with on average good growth conditions and about 25% for a season with on average bad growth conditions. A positive correlation has been found between these levels of seed loss and the level of seed loss at 9.7 s and 17 s treatment time, respectively, in the random impact test as described by Bruce et al., 2002 (Biosystems Eng 81(2): 179-184). Alternatively, to determine whether the level of resistance to pod shattering in a plant is agronomically relevant, the pod sample half-life ('LD50', see above) of the plant can be compared with the pod sample half-life of a plant known to have an average level of pod shatter resistance, such as, for oilseed rape, all currently commercially available oilseed rape varieties.

As used herein, "pod or seed shattering" or "fruit or pod dehiscence" refers to a process that takes place in a fruit after seed maturation, whereby the valves detach from the central septum freeing the seeds. The region that breaks (i.e. the "dehiscence zone") runs the entire length of the fruit between the valves and the replum (external septum). At maturity, the "dehiscence zone" is essentially a non-lignified layer of cells between a region of lignified cells in the valve and the replum. Shattering occurs due to the combination of cell wall loosening in the dehiscence zone and the tensions established by the differential mechanical properties of the drying cells in the silique.

A *Brassica* "fruit", as used herein, refers to an organ of a *Brassica* plant that develops from a gynoecium composed of fused carpels, which, upon fertilization, grows to become a "(seed) pod" or "silique" that contains the developing seeds. A *Brassica* "(seed) pod" or "silique" consists of a fruit wall (carpel) enclosing two locules separated by the septum. The "dehiscence zones" develop at the carpel margins adjacent to the septum and run the length of the silique. The cells of the dehiscence zone eventually begin to degrade and this weakens the contact between the carpel walls or valves and the septum. The loss of cellular cohesion is confined to the cells of the dehiscence zone and results from middle lamella breakdown (Meakin and Roberts, 1990, J Exp Bot 41, 995-1011).

"Dehiscence zones", as used herein, refers to layers of simple, parenchymatous cells, contained in the sutures situated on both sides of the bi-valved pod of plants, in particular *Brassica* plants. The dehiscence zones are situated between the pod valve edge and a central replum that contains the main vascular bundle to the stalk or pedicel. Dissociation of the cells in the dehiscence zone takes place during pod senescence and is complete by the time the pods reach full maturity (Meakin and Roberts, 1990, J Exp Bot 41, 995-1011). Valve separation can then take place. The dehiscence zone contains vascular traces, which pass from the pod wall to the pedicel (stalk) and the replum. The process of pod shatter takes place only after external force fractures the delicate vascular threads, allowing the valves to separate and the seeds to fall to the ground. This occurs during disturbance of the canopy, for example by contact with the combine during harvesting. The vascular tissue contains thickened, lignified cells, which form the collenchymatous groups of cells found adjacent to the conductive cells (Meakin and Roberts, 1990, J Exp Bot 41, 995-1011). This provides rigidity to the tissue and presumably, some resistance to fracturing.

As used herein, "an agronomically relevant threshability" refers to the resistance of a pod, particularly an oilseed rape pod, to opening along the dehiscence zone of the pod with concurrent release of the seeds, upon application of physical forces that allow complete opening of the pods while preventing damage to the seeds, as they are used e.g. in a combine harvester. A positive correlation has been found between a pod sample half-life ('LD50') in a random impact test and their threshability. Oilseed rape pod sample half-lives, as determined in a RIT performed as described in the Examples, which correspond to agronomically relevant threshability should not exceed 80 seconds. Typical sample half-life values for control lines of commercially available oilseed rape varieties are about 10 seconds. Thus, lines with significantly increased pod shatter resistance with agronomically relevant threshability have a pod sample half-life in RIT between about 10 and about 80 seconds, between about 10 and about 60 seconds, between about 10 and about 50 seconds, between about 10 and about 40 seconds, between about 20 and about 40 seconds, between about 20 and about 30 seconds, of about 21 seconds.

"Crop plant" refers to plant species cultivated as a crop, such as *Brassica napus* (AACC, 2n=38), *Brassica juncea* (AABB, 2n=36), *Brassica carinata* (BBCC, 2n=34), *Brassica rapa* (syn. *B. campestris*) (AA, 2n=20), *Brassica oleracea* (CC, 2n=18) or *Brassica nigra* (BB, 2n=16). The definition does not encompass weeds, such as *Arabidopsis thaliana*.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of an ALC gene present within the nuclear genome of a *Brassica* cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operably linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The terms "protein" or "polypeptide" are used interchangeably and refer to molecules consisting of a chain of amino acids, without reference to a specific mode of action, size, 3-dimensional structure or origin. A "fragment" or "portion" of an ALC protein may thus still be referred to as a "protein". An "isolated protein" is used to refer to a protein that is no longer in its natural environment, for example in vitro or in a recombinant bacterial or plant host cell. The term "transcription factor" is used to refer to a protein consisting of at least two discrete domains—a DNA binding domain and an activation or repression domain—that operate together to modulate the rate of transcriptional initiation from target gene promoters (Ptashne, 1988, Nature 335, 683-689). The term "basic helix-loop-helix (bHLH) domain transcription factor" is used to refer to a transcription factor comprising, apart from the bHLH DNA binding domain (Heim et al., 2003, Mol Biol Evol 20, 735-747; Toledo-Ortiz et al., 2003, Plant Cell 15, 1749-1770), domains which are known to be important for the regulation of gene expression which may be conserved at the amino acid level in related proteins from different species (Quong et al., 1993, Mol Cell Biol 13, 792-800). Transcriptional regulators comprising a bHLH domain bind DNA through residues in the basic region while the helix-loop-helix domain promotes dimerization, allowing family members to form hetero- or homodimers (Murre et al., 1989, Cell 56, 777-783).

The term "ALCATRAZ protein" "ALC protein", refers herein to a protein, which is a bHLH protein, which has at least 60% overall protein homology to any one of the *Brassica* ALC-GR3 protein as depicted in SEQ ID NO: 9 and ALC-GR4 protein as depicted in SEQ ID NO: 10, and of which the bHLH domain has at least 90% identity to the bHLH domain of that in any one of the of the *Brassica* ALC_GR3 protein as depicted in SEQ ID NO: 9, amino acids 92-142, and ALC GR4 protein as depicted in SEQ ID NO: 10, amino acids 92-142.

The term "functional ALC protein" refers herein to an ALC protein encoded by a functional ALC gene or a functional ALC allele.

The term "knock-out ALC protein" refers herein to a protein encoded by a knock-out ALC gene or knock-out ALC allele.

The term "ALCATRAZ gene", "ALC gene", "ALCATRAZ allele" or "ALC allele" refers herein to a nucleic acid sequence having at least 50% overall sequence identity to any one of the Brassica ALC genomic sequences ALC-GR3 as depicted in SEQ ID NO: 3 and ALC-GR4 depicted in SEQ ID NO: 4, and which comprises a region of at least 650 nts having at least 65% sequence identity to a region of at least 650 nts of any one of the Brassica ALC genomic sequences ALC-GR3 as depicted in SEQ ID NO: 3 and ALC-GR4 depicted in SEQ ID NO: 4.

The term "functional ALCATRAZ gene", "functional ALC gene", "functional ALCATRAZ allele" or "functional ALC allele" refers herein to a nucleic acid sequence driving the expression of an ALCATRAZ protein (or ALC protein), and which complements the mutations of the Brassica napus double mutant POSH131/POSH134 as described in this application, or which, when present in a Brassica napus genetic background comprising no other functional ALC genes, gives no podshatter resistant phenotype, and a normal formation of the nonlignified cell layer in the dehiscence zone.

The term "weak ALC gene" or "weak ALC allele" refers herein to a mutant alc gene or a mutant alc allele, which drives the expression of an ALCATRAZ protein (or ALC protein), and which complements the mutations of the Brassica napus double mutant POSH131/POSH134 as described in this application, or which, when present in a Brassica napus genetic background comprising no other functional ALC genes, gives no podshatter resistant phenotype.

The term "knock-out ALC gene", "knock-out ALC allele" "full knock-out ALC gene" or "full knock-out ALC allele" refers herein to an ALC gene or ALC allele, which does not complement the Brassica napus double mutant POSH131/POSH134 as described in this application, or which, when present in a Brassica napus genetic background comprising no other functional ALC genes or no other functional ALC alleles, gives rise to a podshatter resistant phenotype.

The term "Naturally occurring knock-out ALC gene" or "Naturally occurring knock-out ALC allele" refers herein to a "knock-out ALC gene" or a "knock-out ALC allele" which is found in plants in the natural population or in the breeding population and which is not produced by human intervention such as mutagenesis or gene targeting.

The term "non-naturally occurring knock-out alc gene" or "non-naturally occurring knock-out alc allele" refers herein to a "knock-out alc gene" or a "knock-out alc allele" which does not occur in plants in the natural population or in the breeding population, but which is produced by human intervention such as mutagenesis or gene targeting.

The term "mutant alc gene" or "mutant alc allele" refers herein to any alc gene or alc allele which is not found in plants in the natural population or breeding population, but which is produced by human intervention such as mutagenesis or gene targeting. A mutant alc allele comprises knock-out alc alleles, and functional alc alleles.

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

A "molecular assay" (or test) refers herein to an assay that indicates (directly or indirectly) the presence or absence of one or more particular ALC alleles at one or both ALC loci. In one embodiment it allows one to determine whether a particular (wild type or mutant) allele is homozygous or heterozygous at the locus in any individual plant.

"Wild type" (also written "wildtype" or "wild-type"), as used herein, refers to a typical form of a plant or a gene as it most commonly occurs in nature. A "wild type plant" refers to a plant in the natural population or in a breeding population. A "wild type allele" refers to an allele of a gene occurring in wild-type plants. A "wild-type ALC allele" comprises functional ALC alleles and knock-out ALC alleles. By contrast, a "mutant plant" refers to a plant produced by human intervention, e.g. by mutagenesis or gene targeting.

A "significantly reduced amount of functional ALC protein" refers to a reduction in the amount of functional ALC protein produced by a cell by at least 30%, 40%, 50%, 60%, 70%, 80%, 90%, 95% or 100% (i.e. no functional ALC protein is produced by the cell) as compared to the amount of functional ALC protein produced by the cell comprising a functional ALC gene. This definition encompasses the production of a "knock-out ALC protein" (e.g. truncated ALC protein), the reduction in the absolute amount of the ALC protein (e.g. no ALC protein being made due to the mutation in the ALC gene).

"Mutagenesis", as used herein, refers to the process in which plant cells (e.g., a plurality of Brassica seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), T-DNA insertion mutagenesis (Azpiroz-Leehan et al. (1997) Trends Genet. 13:152-156), transposon mutagenesis (McKenzie et al. (2002) Theor Appl Genet. 105:23-33), or tissue culture mutagenesis (induction of somaclonal variations), or a combination of two or more of these. Thus, the desired mutagenesis of one or more ALC alleles may be accomplished by one of the above methods. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, Brassica plants are regenerated from the treated cells using known techniques. For instance, the resulting Brassica seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for Brassica napus. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant alc alleles. Several techniques are known to screen for specific mutant alleles, e.g., Delete-agene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant alc alleles are described in the Examples below.

The term "gene targeting" refers herein to directed gene modification that uses mechanisms such as homologous recombination, mismatch repair or site-directed mutagenesis. The method can be used to replace, insert and delete endogenous sequences or sequences previously introduced in plant cells. Methods for gene targeting can be found in, for example, WO 2006/105946 or WO2009/002150.

The term "ortholog" of a gene or protein refers herein to the homologous gene or protein found in another species, which has the same function as the gene or protein, but is (usually) diverged in sequence from the time point on when the species harboring the genes diverged (i.e. the genes evolved from a common ancestor by speciation). Orthologs of the Brassica napus ALC genes may thus be identified in other plant species (e.g. Brassica juncea, etc.) based on both sequence comparisons (e.g. based on percentages sequence identity over the entire sequence or over specific domains) and/or functional analysis.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al., (1989) and Sambrook and Russell (2001).

DETAILED DESCRIPTION

*Brassica napus* (genome AACC, 2n=4x=38), which is an allotetraploid (amphidiploid) species containing essentially two diploid genomes (the A and the C genome) due to its origin from diploid ancestors. It was found by the inventors that *Brassica napus* comprises six ALC genes in its genome, and that the A genome and the C genome each contain one functional ALC gene encoding a functional ALC protein (ALC_GR3 for the A genome, and ALC_GR4 for the C genome, respectively), whereas the other ALC genes were found to be knock-out alc genes.

As in any diploid genome, two "alleles" can be present in vivo for each ALC gene at each ALC locus in the genome (one allele being the gene sequence found on one chromosome and the other on the homologous chromosome). The nucleotide sequence of these two alleles may be identical (homozygous plant) or different (heterozygous plant) in any given plant, although the number of different possible alleles existing for each ALC gene may be much larger than two in the species population as a whole.

It was moreover found that *Brassica napus* plants, which are homozygous for a non-naturally occurring knockout alc allele in only one of the two ALC genes ALC_GR3 or ALC_GR4, do not show a significant increase in pod shatter resistance compared to *Brassica napus* plants not comprising these non-naturally occurring full knock-out ALC alleles, while in *Brassica napus* plants, which are homozygous for a full knockout alc allele in both ALC genes ALC_GR3 and ALC_GR4, pod shatter resistance is significantly increased, and the level of pod shatter resistance is low enough maintain an agronomically relevant threshability. It is thought that the absence of any functional ALC gene in a *Brassica* plant comprising at least one ALC gene, in particular in a *Brassica napus* plant comprising six ALC genes, may be required in order to obtain a plant, which shows an increased pod shatter resistance, while maintaining an agronomically relevant threshability of the pods.

Thus in one embodiment of the invention, a *Brassica* plant comprising at least one ALC gene, characterized in that all ALC genes are knock-out ALC genes. In a further embodiment, the *Brassica* plant comprises at least one non-naturally occurring knock-out alc gene. In a specific embodiment, the *Brassica* plant contains an A genome, a C genome, or both an A genome and a C genome, characterized in that the A genome and the C genome each comprise one non-naturally occurring knock-out alc gene.

In yet another embodiment, *Brassica* plants are provided comprising at least one ALC gene, of which at least one ALC gene is a non-naturally occurring knock-out alc gene containing a premature stopcodon or a mutated splice site. In yet another embodiment, these *Brassica* plants comprise an A genome, a C genome, or both an A genome and a C genome, characterized in that the A genome and the C genome each comprise one non-naturally occurring knock-out alc gene, comprising a premature stopcodon or a mutated splice site. In yet another embodiment, said non-naturally occurring knock-out alc gene from the A genome contains a mutated splice site, and said non-naturally occurring knock-out alc gene from the C genome contains a premature stopcodon. In a further aspect of the invention, said *Brassica* plants comprising said non-naturally occurring knock-out alc genes are homozygous for said non-naturally occurring knock-out alc genes.

In a further embodiment of this invention, a *Brassica* plant with significantly reduced seed shattering is provided which is obtained by a method comprising downregulation of ALC gene expression.

Downregulation of ALC gene expression may result in a significantly reduced amount of functional ALC protein which may be at least 30%, 40%, 50%, 60%, 70%, 80%, 90%, 95% or 100% (i.e. no functional ALC protein is produced by the cell) as compared to the amount of the ALC protein produced by the cell comprising an ALC gene.

Downregulation of gene expression of all ALC genes encoding a functional ALC protein can occur through well-established techniques of gene silencing, in which a DNA construct is introduced into the plant cells that encodes a biologically active RNA which decreases the levels of ALC mRNAs available for translation. This biologically active RNA may downregulate ALC gene expression through, for example, co-suppression (sense RNA suppression), antisense RNA, double-stranded RNA (dsRNA) or microRNA (miRNA).

In plants comprising more than one functional ALC gene, silencing of all genes can be achieved, for example, by introducing a DNA that encodes one biologically active RNA which targets all envisaged functional ALC genes, characterized in that the biologically active RNA comprises a region with sufficient homology to all ALC genes to be downregulated. Alternatively, the biologically active RNA can consist of several regions, each of which contains sufficient homology to one of the ALC genes to be down-regulated. Alternatively, more than one DNA construct encoding a biologically active RNA can be introduced into the plant cell, each of which silences another ALC gene to be down-regulated.

Sufficient homology to the ALC genes to be downregulated as used herein means that the transcribed DNA region (and resulting RNA molecule) comprises at least 20 consecutive nucleotides having at least 95% sequence identity to the nucleotide sequence or the complement of the nucleotide of the ALC gene to be down-regulated.

In a further embodiment, a *Brassica* plant with significantly reduced seed shattering is provided which is obtained by a method comprising downregulation of ALC gene expression through a method comprising the following steps:
 (a) providing plant cells with one or more chimeric genes to create transgenic plant cells, said chimeric genes comprising the following operably linked DNA fragments
  i. a plant-expressible promoter;
  ii. a DNA region, which when transcribed yields an RNA molecule inhibitory to one or more ALC genes encoding a functional ALC protein;
  iii. a 3' end region involved in transcription termination and polyadenylation;
 (b) regenerating a population of transgenic plant lines from said transgenic plant cell; and (c) identifying a plant line with increased podshatter resistance within said population of transgenic plant lines.

ALC gene expression may be down-regulated by introducing a chimeric DNA construct which yields a sense RNA molecule capable of down-regulating expression of one or more functional ALC genes by co-suppression. The transcribed DNA region will yield upon transcription a so-called sense RNA molecule capable of reducing the expression of an ALC gene in the target plant or plant cell in a transcriptional or post-transcriptional manner. The transcribed DNA region (and resulting RNA molecule) comprises at least 20 consecutive nucleotides having at least 95% sequence identity to the nucleotide sequence of one or more ALC genes encoding a functional ALC protein present in the plant cell or plant.

ALC gene expression may also be down-regulated by introducing a chimeric DNA construct which yields an antisense RNA molecule capable of down-regulating expression of one or more functional ALC genes. The transcribed DNA region will yield upon transcription a so-called antisense RNA molecule capable of reducing the expression of an ALC gene in the target plant or plant cell in a transcriptional or post-transcriptional manner. The transcribed DNA region (and resulting RNA molecule) comprises at least 20 consecutive nucleotides having at least 95% sequence identity to the complement of the nucleotide sequence of one or more functional ALC genes present in the plant cell or plant.

The minimum nucleotide sequence of the antisense or sense RNA region of about 20 nt of the ALC gene may be comprised within a larger RNA molecule, varying in size from 20 nt to a length equal to the size of the target gene. The mentioned antisense or sense nucleotide regions may thus be about from about 21 nt to about 1300 nt long, such as 21 nt, 40 nt, 50 nt, 100 nt, 200 nt, 300 nt, 500 nt, 1000 nt, or even about 1300 nt or larger in length. Moreover, it is not required for the purpose of the invention that the nucleotide sequence of the used inhibitory ALC RNA molecule or the encoding region of the transgene, is completely identical or complementary to the endogenous ALC gene the expression of which is targeted to be reduced in the plant cell. The longer the sequence, the less stringent the requirement for the overall sequence identity is. Thus, the sense or antisense regions may have an overall sequence identity of about 40% or 50% or 60% or 70% or 80% or 90% or 100% to the nucleotide sequence of the endogenous ALC gene or the complement thereof. However, as mentioned, antisense or sense regions should comprise a nucleotide sequence of 20 consecutive nucleotides having about 95 to about 100% sequence identity to the nucleotide sequence of the endogenous ALC gene. The stretch of about 95 to about 100% sequence identity may be about 50, 75 or 100 nt. It will be clear that all combinations between mentioned length and sequence identity can be made, both in sense and/or antisense orientation.

The efficiency of the above mentioned chimeric genes for antisense RNA or sense RNA-mediated gene expression level down-regulation may be further enhanced by inclusion of DNA elements which result in the expression of aberrant, non-polyadenylated ALC inhibitory RNA molecules. One such DNA element suitable for that purpose is a DNA region encoding a self-splicing ribozyme, as described in WO 00/01133. The efficiency may also be enhanced by providing the generated RNA molecules with nuclear localization or retention signals as described in WO 03/076619.

ALC gene expression may also be down-regulated by introducing a chimeric DNA construct which yields a double-stranded RNA molecule capable of down-regulating ALC gene expression. Upon transcription of the DNA region the RNA is able to form dsRNA molecule through conventional base paring between a sense and antisense region, whereby the sense and antisense region are nucleotide sequences as hereinbefore described. dsRNA-encoding ALC expression-reducing chimeric genes according to the invention may further comprise an intron, such as a heterologous intron, located e.g. in the spacer sequence between the sense and antisense RNA regions in accordance with the disclosure of WO 99/53050 (incorporated herein by reference). To achieve the construction of such a transgene, use can be made of the vectors described in WO 02/059294 A1.

ALC gene expression may also be down-regulated by introducing a chimeric DNA construct which yields a pre-miRNA molecule which is processed into a miRNA capable of guiding the cleavage of ALC mRNA. miRNAs are small endogenous RNAs that regulate gene expression in plants, but also in other eukaryotes. In plants, these about 21 nucleotide long RNAs are processed from the stem-loop regions of long endogenous pre-miRNAs by the cleavage activity of DICERLIKE1 (DCL1). Plant miRNAs are highly complementary to conserved target mRNAs, and guide the cleavage of their targets. miRNAs appear to be key components in regulating the gene expression of complex networks of pathways involved inter alia in development.

As used herein, a "miRNA" is an RNA molecule of about 20 to 22 nucleotides in length which can be loaded into a RISC complex and direct the cleavage of a target RNA molecule, wherein the target RNA molecule comprises a nucleotide sequence essentially complementary to the nucleotide sequence of the miRNA molecule whereby one or more of the following mismatches may occur:

A mismatch between the nucleotide at the 5' end of said miRNA and the corresponding nucleotide sequence in the target RNA molecule;

A mismatch between any one of the nucleotides in position 1 to position 9 of said miRNA and the corresponding nucleotide sequence in the target RNA molecule;

Three mismatches between any one of the nucleotides in position 12 to position 21 of said miRNA and the corresponding nucleotide sequence in the target RNA molecule provided that there are no more than two consecutive mismatches.

No mismatch is allowed at positions 10 and 11 of the miRNA (all miRNA positions are indicated starting from the 5' end of the miRNA molecule).

As used herein, a "pre-miRNA" molecule is an RNA molecule of about 100 to about 200 nucleotides, preferably about 100 to about 130 nucleotides which can adopt a secondary structure comprising a dsRNA stem and a single stranded RNA loop and further comprising the nucleotide sequence of the miRNA and its complement sequence of the miRNA* in the double-stranded RNA stem. Preferably, the miRNA and its complement are located about 10 to about 20 nucleotides from the free ends of the miRNA dsRNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* do not need to be perfect and about 1 to 3 bulges of unpaired nucleotides can be tolerated. The secondary structure adopted by an RNA molecule can be predicted by computer algorithms conventional in the art such as mFold, UNAFold and RNAFold. The particular strand of the dsRNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

It can also be used for the invention to down-regulate ALC protein activity. ALC protein activity may be down-regulated by introducing a DNA construct into the *Brassica* plant which encodes a dominant-negative ALC protein. A dominant-negative ALC protein has been described in Rajani et al. (2001, Current Biology 11, 1914-1922).

ALC protein activity may also be downregulated by introducing a DNA construct into the *Brassica* plant which encodes inactivating antibodies to ALC proteins. "Inactivating antibodies to ALC proteins" are antibodies or parts thereof which specifically bind at least to some epitopes of ALC proteins, and which inhibit the activity of the target protein.

Further provided herein are nucleic acid sequences of wild type and mutant alc genes/alleles from *Brassica* species. Also provided are *Brassica* plants and plant parts comprising specific combinations of mutant alc genes in their genome, whereby seed shattering is reduced in these plants. In addition kits and methods for marker assisted selection (MAS) for combining or detecting ALC genes and/or alleles are provided. Each of the embodiments of the invention is described in detail herein below.

Nucleic Acid Sequences According to the Invention

Provided are both wild type ALC nucleic acid sequences encoding functional ALC proteins and naturally occurring as well as non-naturally occurring knock-out alc nucleic acid of ALC genes from Brassicaceae, particularly from *Brassica* species, especially from *Brassica napus*, but also from other *Brassica* crop species. For example, *Brassica* species comprising an A and/or a C genome may comprise different alleles of ALC genes, which can be identified and combined in a single plant according to the invention. In addition, mutagenesis methods can be used to generate mutations in wild type ALC alleles, thereby generating mutant alc alleles for use according to the invention. Because specific ALC alleles are preferably combined in a plant by crossing and selection, in one embodiment the ALC and/or alc nucleic acid sequences are provided within a plant (i.e. endogenously), e.g. a *Brassica* plant, preferably a *Brassica* plant which can be crossed with *Brassica napus* or which can be used to make a "synthetic" *Brassica napus* plant. Hybridization between different *Brassica* species is described in the art, e.g., as referred to in Snowdon (2007, Chromosome research 15: 85-95). Interspecific hybridization can, for example, be used to transfer genes from, e.g., the C genome in *B. napus* (AACC) to the C genome in *B. carinata* (BBCC), or even from, e.g., the C genome in *B. napus* (AACC) to the B genome in *B. juncea* (AABB) (by the sporadic event of illegitimate recombination between their C and B genomes). "Resynthesized" or "synthetic" *Brassica napus* lines can be produced by crossing the original ancestors, *B. oleracea* (CC) and *B. rapa* (AA). Interspecific, and also intergeneric, incompatibility barriers can be successfully overcome in crosses between *Brassica* crop species and their relatives, e.g., by embryo rescue techniques or protoplast fusion (see e.g. Snowdon, above).

However, isolated ALC and alc nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a non-functional or no protein (e.g. by expression in a recombinant host cell as described below) and for selection and transfer of specific alleles from one plant into another, in order to generate a plant having the desired combination of functional and mutant alleles.

Nucleic acid sequences of six ALC genes have been isolated from *Brassica napus*, as depicted in the sequence listing. Four of the ALC genes, ALC-GR1 (SEQ ID NO: 1), ALC-GR2 (SEQ ID NO: 2), ALC-GR5 (SEQ ID NO: 5) and ALC-GR6 (SEQ ID NO: 6) do not encode a functional ALC protein. ALC-GR3 (SEQ ID NO: 3) and ALC-GR4 (SEQ ID NO: 4) encode a functional ALC protein. The cDNAs from the coding sequences from ALC-GR3 and ALC-GR4 have also been determined and are depicted in SEQ ID NO: 7 (coding sequence from ALC-GR3) and SEQ ID NO: 8 (coding sequence from ALC-GR4). The proteins encoded by these cDNAs are depicted in SEQ ID NO: 9 (ALC-GR3) and SEQ ID NO: 10 (ALC-GR4).

"ALC gene from the A genome" "ALC-A" or "ALC-A variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 9 or nucleic acid sequences having at least 80%, at least 85%, at least 90%, at least 95%, 96%, 97%, 98%, 99% or 100% sequence identity with SEQ ID NO: 3. These nucleic acid sequences may also be referred to as being "essentially similar" or "essentially identical" to the ALC sequences provided in the sequence listing.

"ALC gene from the C genome" or "ALC-C" or "ALC-C variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 10 or nucleic acid sequences having at least 80%, at least 85%, at least 90%, at least 95%, 96%, 97%, 98%, 99% or 100% sequence identity with SEQ ID NO: 4. These nucleic acid sequences may also be referred to as being "essentially similar" or "essentially identical" to the ALC sequences provided in the sequence listing.

The invention provides both nucleic acid sequences encoding wild type, functional ALC-A and ALC-C proteins, including variants and fragments thereof (as defined further below), as well as mutant nucleic acid sequences of any of these, whereby the mutation in the nucleic acid sequence results in an amino acids being substituted in comparison to the wild type ALC protein, introduction of a premature translation stopcodon, or mutation in a splice site. In a specific embodiment, the mutation(s) in the nucleic acid sequence result in a premature translation stopcodon or mutation of a splice site whereby the biological activity of the ALC protein is significantly reduced or completely abolished. A significant reduction in or complete abolishment of the biological activity of the ALC protein refers herein to a reduction in or abolishment of the ability to complement the mutations of the *Brassica napus* double mutant POSH131/POSH134 as described in this application, such that, when activity of all functional ALC proteins encoded by all ALC genes in the *Brassica* genome is abolished, the pod shatter resistance is increased as compared to a plant expressing the corresponding wild type ALC proteins.

To determine the functionality of a specific ALC allele/protein in plants, particularly in *Brassica* plants, the level of resistance to pod shattering in the plants can be determined by performing macroscopical, microscopical and histological assays on fruits and flowers of the plants comprising the specific ALC allele/protein and of corresponding wild type plants analogous to the assays performed on *Arabidopsis* fruits and flowers as described by Liljegren et al., 2004, Cell 116: 843-853 or as described in the Examples below. Briefly, changes in pod shatter resistance can be evaluated and/or measured, e.g., by macroscopical tests, such as inspection of the seed pods with naked eye to evaluate, e.g., the presence or absence of the valve margins, the length of the beak of the pods, etc.; a Manual Impact Test (MIT) to compare the level of pod shatter resistance between different mutant alc lines and corresponding wild type lines by evaluating the ease of pod opening upon gently twisting the pods; a Random Impact Test (RIT) to compare the threshability of seed pods from plants from different mutant alc lines and corresponding wild type lines, respectively, by measuring the half-life of pod samples of these lines; and/or by microscopic tests to examine, e.g., whether and how cells at the valve margin and the dehiscence zone of seed pods are affected by mutations in ALC. Once the dimerization partner of the ALC protein (e.g., the ALC protein itself in case its functioning depends on the formation of an homodimer or another protein in case its functioning depends on the formation of an heterodimer) and/or the DNA sequence to which the ALC protein binds are identified and characterized, the functionality of a specific ALC allele/protein can alternatively be evaluated by recombinant DNA techniques as known in the art, e.g., by co-expressing both partners of the dimer in a host cell (e.g. a bacterium, such as *E. coli*) and evaluating if dimers can still be formed, and if the dimers can still bind to DNA binding site.

Both endogenous and isolated nucleic acid sequences are provided herein. Also provided are fragments of the ALC sequences and ALC variant nucleic acid sequences defined above, for use as primers or probes and as components of kits according to another aspect of the invention (see further below). A "fragment" of a ALC or alc nucleic acid sequence or variant thereof (as defined) may be of various lengths, such as at least 10, 12, 15, 18, 20, 50, 100, 200, 500, 600 contiguous nucleotides of the ALC or alc sequence (or of the variant sequence).

Nucleic Acid Sequences Encoding Functional ALC Proteins

The nucleic acid sequences depicted in SEQ ID NO: 3 and SEQ ID NO: 4 encode wild type, functional ALC proteins from *Brassica napus*. The cDNAs of the coding sequences of the two *Brassica napus* genes encoding a functional ALC protein are depicted in SEQ ID NO: 7 and SEQ ID NO: 8. Thus, these sequences are endogenous to the *Brassica napus* plants from which they were isolated. Other *Brassica* crop species, varieties, breeding lines or wild accessions may be screened for other ALC alleles, encoding the same ALC proteins or variants thereof. For example, nucleic acid hybridization techniques (e.g. Southern blot analysis, using for example stringent hybridization conditions) or PCR-based techniques may be used to identify ALC alleles endogenous to other *Brassica* plants, such as various *Brassica napus* varieties, lines or accessions, but also *Brassica juncea* (especially ALC alleles on the A-genome), *Brassica carinata* (especially ALC alleles on the C-genome) and *Brassica rapa* (A-genome) and *Brassica oleracea* (C-genome) plants, organs and tissues can be screened for other wild type ALC alleles. To screen such plants, plant organs or tissues for the presence of ALC alleles, the ALC nucleic acid sequences provided in the sequence listing, or variants or fragments of any of these, may be used. For example whole sequences or fragments may be used as probes or primers. For example specific or degenerate primers may be used to amplify nucleic acid sequences encoding ALC proteins from the genomic DNA of the plant, plant organ or tissue. These ALC nucleic acid sequences may be isolated and sequenced using standard molecular biology techniques. Bioinformatics analysis may then be used to characterize the allele(s), for example in order to determine which ALC allele the sequence corresponds to and which ALC protein or protein variant is encoded by the sequence.

Whether a nucleic acid sequence encodes a functional ALC protein can be analyzed by recombinant DNA techniques as known in the art, e.g., by a genetic complementation test using, e.g., an *Arabidopsis* plant, which is homozygous for a full knock-out alc mutant allele (such as described in Rajani et al. (2001, Current Biology 11, 1914-1922), or a *Brassica napus* plant, which is homozygous for a full knock-out alc mutant allele of both the ALC-A and ALC-C genes, such as the double mutant POSH131/POSH134 as described in this application.

In addition, it is understood that ALC nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below. Fragments include nucleic acid sequences encoding only the bHLH domain, or smaller fragments comprising part of the bHLH domain, such as the basic domain or the HLH domain, etc.

Nucleic Acid Sequences Encoding Mutant ALC Proteins

Mutant alc nucleic acid sequences can comprise one or more nucleotide deletions, insertions or substitutions relative to the wild type nucleic acid sequences. Such mutant nucleic acid sequences (referred to as alc sequences) can be generated and/or identified using various known methods, as described further below. Again, such nucleic acid molecules are provided both in endogenous form and in isolated form. In one embodiment, the mutation(s) result in a substitution in the amino acid sequence of the encoded ALC protein. In another embodiment, the mutation(s) in the nucleic acid sequence result in a significantly reduced or completely abolished biological activity of the encoded ALC protein relative to the wild type protein.

The nucleic acid molecules may, thus, comprise one or more mutations, such as:

(a) a "missense mutation", which is a change in the nucleic acid sequence that results in the substitution of an amino acid for another amino acid;

(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation;

(c) an "insertion mutation" of one or more amino acids, due to one or more codons having been added in the coding sequence of the nucleic acid;

(d) a "deletion mutation" of one or more amino acids, due to one or more codons having been deleted in the coding sequence of the nucleic acid;

(e) a "frameshift mutation", resulting in the nucleic acid sequence being translated in a different frame downstream of the mutation. A frameshift mutation can have various causes, such as the insertion, deletion or duplication of one or more nucleotides;

(f) a mutated splice site, resulting in altered splicing, which results in an altered mRNA processing and, consequently, in an altered encoded protein which contains either deletions, substitutions or insertions of various lengths, possibly combined with premature translation termination.

As defined in this application, a "knock-out ALC protein" refers herein to a protein encoded by a knock-out alc gene or knock-out alc allele, which is an ALC allele, which does not complement the *Brassica napus* double mutant POSH131/POSH134 as described in this application, or which, when present in a *Brassica napus* genetic background comprising no other functional ALC genes or no other functional ALC alleles, gives rise to a podshatter resistant phenotype.

From this definition, it is thus clear that a knock-out ALC protein can be provided by a missense, nonsense, insertion, deletion, frameshift, or splice site mutation.

Thus in one embodiment, nucleic acid sequences comprising one or more of any of the types of mutations described above are provided. In another embodiment, alc sequences comprising a nonsense mutation, or a mutated splice site are provided. Any of the above mutant nucleic acid sequences are provided per se (in isolated form), as are plants and plant parts comprising such sequences endogenously. In Table 1, specific alc alleles are described and seed deposits of *Brassica napus* seeds comprising alc alleles have been deposited as indicated.

A nonsense mutation in an ALC allele, as used herein, is a mutation in an ALC allele whereby a translation stop codon is introduced into the coding DNA and the corresponding mRNA sequence of the corresponding wild type ALC allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. In one embodiment, a mutant alc allele comprising a nonsense mutation is an ALC allele wherein an in-frame stop codon is introduced in the ALC codon sequence by a single nucleotide substitution, such as the mutation of CAG to TAG, TGG to TAG, TGG to TGA, or CAA to TAA. The truncated protein lacks the amino acids encoded by the coding DNA downstream of the mutation (i.e. the C-terminal part of the ALC protein) and maintains the amino acids encoded by the coding DNA upstream of the mutation (i.e. the N-terminal part of the ALC protein). In one embodiment, a non-functional mutant alc allele comprising a nonsense mutation is provided. In another embodiment, an non-functional ALC-GR4 allele comprising a nonsense mutation at position 646 is provided. Seeds comprising a mutant ALC-GR4 allele comprising a nonsense mutation at position 646, resulting in a truncated protein after amino acid 118 have been deposited at the NCIMB (NCIMB Ltd, Ferguson Building, Craibstone Estate, Bucksburn, Aberdeen AB21 9YA, Scotland, UK) on 27 Oct. 2010, under accession number NCIMB 41771.

Table 1 describes a range of possible nonsense mutations in the *Brassica napus* ALC sequences provided herein:

TABLE 1a

Potential missense and splice site mutations in ALC-GR3 (SEQ ID NO: 3)

| Position | WT sequence | Mutant sequence | Type |
|---|---|---|---|
| 521 | AG]GT | AA]GT | Splice |
| 496 | GCA | GTA | missense (Ala->Val) |
| 504 | CAC | TAC | missense (His->Tyr) |
| 636 | GCA | GTA | Missense (Ala->Val) |
| 654 | CCC | CTC | Missense (Pro->Leu) |
| 667 | AA]GG | AA]AG | Splice |
| 668 | AG]GT | AG]AT | Splice (1) |
| 751 | GAT | AAT | Missense (Asp->Asn) |
| 781 | GAA | AAA | Missense (Glu->Lys) |

(1) seeds comprising a mutant ALC-GR3 allele comprising this splice mutation (called hereinafter ALC-GR3-EMS07) have been deposited at the NCIMB (NCIMB Ltd, Ferguson Building, Craibstone Estate, Bucksburn, Aberdeen AB21 9YA, Scotland, UK) on 27 Oct. 2010, under accession number NCIMB 41771.

TABLE 1b

Potential missense, nonsense and splice site mutations) in ALC-GR4 (SEQ ID NO: 4

| Position | WT sequence | MUT sequence | Type |
|---|---|---|---|
| 646 | CAG | TAG | Nonsense (2) |
| 755 | AG]AC | AA]AC | Splice |
| 807 | CAA | TAA | Nonsense |
| 765 | GCC | ACC | Missense (Ala->Thr) |
| 641 | GCT | GTT | Missense (Ala->Val) |
| 780 | GAA | AAA | Missense (Glu->Lys) |
| 784 | GCT | GTT | Missense (Ala->Val) |
| 773 | ATG | ATA | Missense (Met->Ile) |
| 628 | GAG | AAG | Missense (Glu->Lys) |

TABLE 1b -continued

Potential missense, nonsense and splice site mutations) in ALC-GR4 (SEQ ID NO: 4

| Position | WT sequence | MUT sequence | Type |
|---|---|---|---|
| 821 | AG]GT | AA]GT | Splice |
| 822 | AG]GT | AG]AT | Splice |

(2) seeds comprising a mutant ALC-GR4 allele comprising this nonsense mutation (called hereinafter ALC-GR4-EMS04) have been deposited at the the NCIMB (NCIMB Ltd, Ferguson Building, Craibstone Estate, Bucksburn, Aberdeen AB21 9YA, Scotland, UK) on 27 Oct. 2010, under accession number NCIMB 41771.

Obviously, mutations are not limited to the ones shown in Table 1 and it is understood that analogous STOP mutations may be present in alc alleles other than those depicted in the sequence listing and referred to in Table 1.

A missense mutation in an ALC allele, as used herein, is any mutation (deletion, insertion or substitution) in an ALC allele whereby one or more codons are changed into the coding DNA and the corresponding mRNA sequence of the corresponding wild type ALC allele, resulting in the substitution of one or more amino acids in the wild type ALC protein for one or more other amino acids in the mutant ALC protein. A mutant alc allele comprising a missense mutation is an ALC allele wherein one amino acid is substituted.

A frameshift mutation in an ALC allele, as used herein, is a mutation (deletion, insertion, duplication, and the like) in an ALC allele that results in the nucleic acid sequence being translated in a different frame downstream of the mutation.

A splice site mutation in an alc allele, as used herein, is a mutation (deletion, insertion, substitution, duplication, and the like) in an alc allele whereby a splice donor site or a splice acceptor site is mutated, resulting in altered processing of the mRNA and, consequently, an altered encoded protein, which can have insertions, deletions, substitutions of various lengths, or which can be truncated. In one embodiment, a non-functional mutant alc allele comprising a splice site mutation is provided. In another embodiment, an ALC-GR3 allele is provided comprising a splice mutation at position 668.

Seeds comprising a mutant ALC-GR3 allele comprising a splice mutation at position 668 have been deposited at the NCIMB (NCIMB Ltd, Ferguson Building, Craibstone Estate, Bucksburn, Aberdeen AB21 9YA, Scotland, UK) on 27 Oct. 2010, under accession number NCIMB 41771.

Amino Acid Sequences According to the Invention

Provided are wild type (functional) ALC amino acid sequences from Brassicaceae, particularly from *Brassica* species, especially from *Brassica napus*, but also from other *Brassica* crop species. For example, *Brassica* species comprising an A and/or a C genome may encode different ALC-A or ALC-C amino acids. In addition, mutagenesis methods can be used to generate mutations in wild type ALC alleles, thereby generating mutant alleles which can encode further mutant ALC proteins. In one embodiment the wild type and/or mutant ALC amino acid sequences are provided within a *Brassica* plant (i.e. endogenously). However, isolated ALC amino acid sequences (e.g. isolated from the plant or made synthetically), as well as variants thereof and fragments of any of these are also provided herein.

Amino acid sequences of ALC-A and ALC-C proteins have been isolated from *Brassica napus* as depicted in SEQ ID NO: 9 and SEQ ID NO: 10, respectively.

"ALC-A amino acid sequences" or "ALC-A variant amino acid sequences" according to the invention are amino acid sequences having at least 75%, at least 80%, at least 85%, at least 90%, at least 95%, 98%, 99% or 100% sequence identity with SEQ ID NO: 9. These amino acid sequences may also be referred to as being "essentially similar" or "essentially identical" to the ALC sequences provided in the sequence listing.

"ALC-C amino acid sequences" or "ALC-C variant amino acid sequences" according to the invention are amino acid sequences having at least 75%, at least 80%, at least 85%, at least 90%, at least 95%, 96%, 97%, 98%, 99% or 100% sequence identity with SEQ ID NO: 10. These amino acid sequences may also be referred to as being "essentially similar" or "essentially identical" the ALC sequences provided in the sequence listing.

Thus, the invention provides both amino acid sequences of wild type, functional ALC-A and ALC-C proteins, including variants and fragments thereof (as defined further below), as well as mutant amino acid sequences of any of these.

Both endogenous and isolated amino acid sequences are provided herein. Also provided are fragments of the ALC amino acid sequences and ALC variant amino acid sequences defined above. A "fragment" of an ALC amino acid sequence or variant thereof (as defined) may be of various lengths, such as at least 10, 12, 15, 18, 20, 50, 100, 150, 175, 180 contiguous amino acids of the ALC sequence (or of the variant sequence).

Amino Acid Sequences of Functional ALC Proteins

The amino acid sequences depicted in the sequence listing are wild type, functional ALC proteins from *Brassica napus*. Thus, these sequences are endogenous to the *Brassica napus* plants from which they were isolated. Other *Brassica* crop species, varieties, breeding lines or wild accessions may be screened for other functional ALC proteins with the same amino acid sequences or variants thereof, as described above.

In addition, it is understood that ALC amino acid sequences and variants thereof (or fragments of any of these) may be identified in silico, by screening amino acid databases for essentially similar sequences. Fragments of amino acid molecules according to the invention are also provided. Fragments include amino acid sequences of the bHLH domain, or smaller fragments comprising part of the bHLH domain, such as the basic domain or the HLH domain, etc.

Amino Acid Sequences of Mutant ALC Proteins

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the ALC protein relative to the wild type protein.

In another embodiment, mutant ALC proteins are provided which are truncated whereby the truncation results in a mutant protein that has significantly reduced or no activity in vivo. Such truncated ALC proteins are ALC proteins which lack functional domains in the C-terminal part of the corresponding wild type ALC protein and which maintain the N-terminal part of the corresponding wild type ALC protein. The more truncated the mutant protein is in comparison to the wild type protein, the more the truncation may result in a significantly reduced or no activity of the ALC protein. In one embodiment, a non-functional truncated ALC protein is provided. In another embodiment, a truncated ALC protein comprising the N-terminal part of the corresponding wild type ALC protein up to but not including the Glutamine residue at position 119 in the ALC-GR4 protein sequence is provided.

Methods According to the Invention

Mutant alc alleles may be generated (for example induced by mutagenesis) and/or identified using a range of methods, which are conventional in the art, for example using PCR based methods to amplify part or all of the alc genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant ALC alleles, using techniques which are conventional in the art, for example amplification reactions, such as polymerase chain reaction (PCR) based techniques (amplification of the alc alleles) or hybridization based techniques, e.g. Southern blot analysis, BAC library screening, and the like, and/or direct sequencing of alc alleles. To screen for the presence of point mutations (so called Single Nucleotide Polymorphisms or SNPs) in mutant ALC alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type ALC allele results in the presence of one or more deleted, inserted, or substituted nucleotides (hereinafter called "mutation region") in the resulting mutant ALC allele. The mutant ALC allele can thus be characterized by the location and the configuration of the one or more deleted, inserted, or substituted nucleotides in the wild type ALC allele. The site in the wild type ALC allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) ALC allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) ALC allele which is located either immediately upstream of and contiguous with (5' flanking region or sequence") or immediately downstream of and contiguous with (3' flanking region or sequence") the mutation region in the mutant ALC allele (or in the corresponding wild type ALC allele). A "joining region" as used herein refers to a DNA region in the mutant (or the corresponding wild type) ALC allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

The tools developed to identify a specific mutant ALC allele or the plant or plant material comprising a specific mutant ALC allele, or products which comprise plant material comprising a specific mutant ALC allele are based on the specific genomic characteristics of the specific mutant ALC allele as compared to the genomic characteristics of the corresponding wild type ALC allele, such as, a specific restriction map of the genomic region comprising the mutation region, molecular markers or the sequence of the flanking and/or mutation regions.

Once a specific mutant ALC allele has been sequenced, primers and probes can be developed which specifically recognize a sequence within the 5' flanking, 3' flanking and/or mutation regions of the mutant ALC allele in the nucleic acid (DNA or RNA) of a sample by way of a molecular biological technique. For instance a PCR method can be developed to identify the mutant ALC allele in biological samples (such as samples of plants, plant material or products comprising plant material). Such a PCR is based on at least two specific "primers": one recognizing a sequence within the 5' or 3' flanking region of the mutant ALC allele and the other recognizing a sequence within the 3' or 5' flanking region of the mutant ALC allele, respectively; or one recognizing a sequence within the 5' or 3' flanking region of the mutant ALC allele and the other recognizing a sequence within the mutation region of the mutant ALC allele; or one recognizing a sequence within the 5' or 3' flanking region of the mutant ALC allele and the other recognizing a sequence spanning the joining region between the 3' or 5' flanking region and the mutation region of the specific mutant ALC allele (as described further below), respectively.

The primers preferably have a sequence of between 15 and 35 nucleotides which under optimized PCR conditions "specifically recognize" a sequence within the 5' or 3' flanking region, a sequence within the mutation region, or a sequence spanning the joining region between the 3' or 5' flanking and mutation regions of the specific mutant ALC allele, so that a specific fragment ("mutant ALC specific fragment" or discriminating amplicon) is amplified from a nucleic acid sample comprising the specific mutant ALC allele. This means that only the targeted mutant ALC allele, and no other sequence in the plant genome, is amplified under optimized PCR conditions.

PCR Primers Suitable for the Invention May be the Following:

oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant ALC allele or the complement thereof (i.e., for example, the sequence 5' or 3' flanking the one or more nucleotides deleted, inserted or substituted in the mutant ALC alleles of the invention, such as the sequence 5' or 3' flanking the non-sense, missense or frameshift mutations described above or the sequence 5' or 3' flanking the STOP codon mutations indicated in the above Tables or the substitution mutations indicated above or the complement thereof) (primers recognizing 5' flanking sequences); or oligonucleotides ranging in length from 17 nt to about 200 nt, comprising a nucleotide sequence of at least 17 consecutive nucleotides, preferably 20 nucleotides selected from the sequence of the mutation region of a specific mutant ALC allele or the complement thereof (i.e., for example, the sequence of nucleotides inserted or substituted in the ALC genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant ALC alleles of the invention and the sequence of the one or more nucleotides inserted or substituted or the sequence 3' or 5', respectively, flanking the one or more nucleotides deleted, such as the joining region between a sequence 5' or 3' flanking non-sense, missense or frameshift mutations in the ALC genes of the invention described above and the sequence of the non-sense, missense or frameshift mutations, or the joining region between a sequence 5' or 3' flanking a potential STOP codon mutation as indicated in the above Tables or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A↔T; G↔C) and reading the sequence in the 5' to 3' direction, i.e. in opposite direction of the represented nucleotide sequence.

Examples of primers suitable to identify specific mutant ALC alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant ALC allele, provided the mismatches still allow specific identification of the specific mutant ALC allele with these primers under optimized PCR conditions. The range of allowable mismatches however, can easily be determined experimentally and are known to a person skilled in the art.

Detection and/or identification of a "mutant ALC specific fragment" can occur in various ways, e.g., via size estimation after gel or capillary electrophoresis or via fluorescence-based detection methods. The mutant ALC specific fragments may also be directly sequenced. Other sequence specific methods for detection of amplified DNA fragments are also known in the art.

Standard PCR protocols are described in the art, such as in 'PCR Applications Manual" (Roche Molecular Biochemicals, 2nd Edition, 1999) and other references. The optimal conditions for the PCR, including the sequence of the specific primers, is specified in a "PCR identification protocol" for each specific mutant ALC allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of PCR identification protocols to identify specific mutant ALC alleles are described in the Examples.

Alternatively, specific primers can be used to amplify a mutant ALC specific fragment that can be used as a "specific probe" for identifying a specific mutant ALC allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant ALC allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant ALC allele (hereinafter referred to as "mutant ALC specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant ALC allele.

Specific probes suitable for the invention may be the following:
oligonucleotides ranging in length from 13 nt to about 1000 nt, comprising a nucleotide sequence of at least 13 consecutive nucleotides selected from the 5' or 3' flanking sequence of a specific mutant ALC allele or the complement thereof (i.e., for example, the sequence 5' or 3' flanking the one or more nucleotides deleted, inserted or substituted in the mutant ALC alleles of the invention, such as the sequence 5' or 3' flanking the non-sense, mis-sense or frameshift mutations described above or the sequence 5' or 3' flanking the potential STOP codon mutations indicated in the above Tables or the substitution mutations indicated above), or a sequence having at least 80% sequence identity therewith (probes recognizing 5' flanking sequences); or oligonucleotides ranging in length from 13 nt to about 1000 nt, comprising a nucleotide sequence of at least 13 consecutive nucleotides selected from the mutation sequence of a specific mutant ALC allele or the complement thereof (i.e., for example, the sequence of nucleotides inserted or substituted in the ALC genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be not longer than 50, more preferably not longer than 25 or even not longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant ALC alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense or frameshift mutations in the ALC genes of the invention described above and the sequence of the non-sense, mis-sense or frameshift mutations, or the joining region between a sequence 5' or 3' flanking a potential STOP codon mutation as indicated in the above Tables or the substitution mutations indicated above and the sequence of the potential STOP codon or substitution mutation, respectively), provided the mentioned nucleotide sequence is not derived exclusively from either the mutation region or flanking regions.

Examples of specific probes suitable to identify specific mutant ALC alleles are described in the Examples.

Detection and/or identification of a "mutant ALC specific region" hybridizing to a specific probe can occur in various ways, e.g., via size estimation after gel electrophoresis or via fluorescence-based detection methods. Other sequence specific methods for detection of a "mutant ALC specific region" hybridizing to a specific probe are also known in the art.

Alternatively, plants or plant parts comprising one or more mutant alc alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant alc alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in ALC alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant alc alleles. As for the mutagenesis techniques above, preferably *Brassica* species are screened which comprise an A and/or a C genome, so that the identified alc allele can subsequently be introduced into other *Brassica* species, such as *Brassica napus*, by crossing (inter- or intraspecific crosses) and selection. In ECOTILLING natural polymorphisms in breeding lines or related species are screened for by the TILLING methodology described above, in which individual or pools of plants are used for PCR amplification of the alc target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant alc alleles (and *Brassica* plants comprising one or more of these) can be identified. The desired mutant alleles can then be combined with the desired wild type alleles by crossing and selection methods as described further below. Finally a single plant comprising the desired number of mutant alc and the desired number of wild type ALC alleles is generated.

Oligonucleotides suitable as PCR primers or specific probes for detection of a specific mutant ALC allele can also be used to develop methods to determine the zygosity status of the specific mutant ALC allele.

To determine the zygosity status of a specific mutant ALC allele, a PCR-based assay can be developed to determine the presence of a mutant and/or corresponding wild type ALC specific allele.

To determine the zygosity status of a specific mutant ALC allele, two primers specifically recognizing the wild-type ALC allele can be designed in such a way that they are directed towards each other and have the mutation region located in between the primers. These primers may be primers specifically recognizing the 5' and 3' flanking sequences, respectively. This set of primers allows simultaneous diagnostic PCR amplification of the mutant, as well as of the corresponding wild type ALC allele.

Alternatively, to determine the zygosity status of a specific mutant ALC allele, two primers specifically recognizing the wild-type ALC allele can be designed in such a way that they are directed towards each other and that one of them specifically recognizes the mutation region. These primers may be primers specifically recognizing the sequence of the 5' or 3' flanking region and the mutation region of the wild type ALC allele, respectively. This set of primers, together with a third primer which specifically recognizes the sequence of the mutation region in the mutant ALC allele, allow simultaneous diagnostic PCR amplification of the mutant ALC gene, as well as of the wild type ALC gene.

Alternatively, to determine the zygosity status of a specific mutant ALC allele, two primers specifically recognizing the wild-type ALC allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type ALC allele, respectively. This set of primers, together with a third primer which specifically recognizes the joining region between the mutation region and the 3' or 5' flanking region of the mutant ALC allele, respectively, allow simultaneous diagnostic PCR amplification of the mutant ALC gene, as well as of the wild type ALC gene.

Alternatively, the zygosity status of a specific mutant ALC allele can be determined by using alternative primer sets that specifically recognize mutant and wild type ALC alleles.

If the plant is homozygous for the mutant ALC gene or the corresponding wild type ALC gene, the diagnostic PCR assays described above will give rise to a single PCR product typical, preferably typical in length, for either the mutant or wild type ALC allele. If the plant is heterozygous for the mutant ALC allele, two specific PCR products will appear, reflecting both the amplification of the mutant and the wild type ALC allele.

Identification of the wild type and mutant ALC specific PCR products can occur e.g. by size estimation after gel or capillary electrophoresis (e.g. for mutant ALC alleles comprising a number of inserted or deleted nucleotides which results in a size difference between the fragments amplified from the wild type and the mutant ALC allele, such that said fragments can be visibly separated on a gel); by evaluating the presence or absence of the two different fragments after gel or capillary electrophoresis, whereby the diagnostic PCR amplification of the mutant ALC allele can, optionally, be performed separately from the diagnostic PCR amplification of the wild type ALC allele; by direct sequencing of the amplified fragments; or by fluorescence-based detection methods.

Examples of primers suitable to determine the zygosity of specific mutant ALC alleles are described in the Examples.

Alternatively, to determine the zygosity status of a specific mutant ALC allele, a hybridization-based assay can be developed to determine the presence of a mutant and/or corresponding wild type ALC specific allele:

To determine the zygosity status of a specific mutant ALC allele, two specific probes recognizing the wild-type ALC allele can be designed in such a way that each probe specifically recognizes a sequence within the ALC wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type ALC allele.

Alternatively, to determine the zygosity status of a specific mutant ALC allele, two specific probes recognizing the wild-type ALC allele can be designed in such a way that one of them specifically recognizes a sequence within the ALC wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type ALC allele, respectively. The use of one or, preferably, both of these probes, optionally, together with a third probe which specifically recognizes the sequence of the mutation region in the mutant ALC allele, allow diagnostic hybridization of the mutant and of the wild type ALC gene.

Alternatively, to determine the zygosity status of a specific mutant ALC allele, a specific probe recognizing the wild-type ALC allele can be designed in such a way that the probe specifically recognizes the joining region between the 5' or 3' flanking region, preferably the 5' flanking region, and the mutation region of the wild type ALC allele. This probe, optionally, together with a second probe that specifically recognizes the joining region between the 5' or 3' flanking region, preferably the 5' flanking region, and the mutation region of the mutant ALC allele, allows diagnostic hybridization of the mutant and of the wild type ALC gene.

Alternatively, the zygosity status of a specific mutant ALC allele can be determined by using alternative sets of probes that specifically recognize mutant and wild type ALC alleles.

If the plant is homozygous for the mutant ALC gene or the corresponding wild type ALC gene, the diagnostic hybridization assays described above will give rise to a single specific hybridization product, such as one or more hybridizing DNA (restriction) fragments, typical, preferably typical in length, for either the mutant or wild type ALC allele. If the plant is heterozygous for the mutant ALC allele, two specific hybridization products will appear, reflecting both the hybridization of the mutant and the wild type ALC allele.

Identification of the wild type and mutant ALC specific hybridization products can occur e.g. by size estimation after gel or capillary electrophoresis (e.g. for mutant ALC alleles comprising a number of inserted or deleted nucleotides which results in a size difference between the hybridizing DNA (restriction) fragments from the wild type and the mutant ALC allele, such that said fragments can be visibly separated on a gel); by evaluating the presence or absence of the two different specific hybridization products after gel or capillary electrophoresis, whereby the diagnostic hybridization of the mutant ALC allele can, optionally, be performed separately from the diagnostic hybridization of the wild type ALC allele; by direct sequencing of the hybridizing DNA (restriction) fragments; or by fluorescence-based detection methods.

Examples of probes suitable to determine the zygosity of specific mutant ALC alleles are described in the Examples.

Furthermore, detection methods specific for a specific mutant ALC allele that differ from PCR- or hybridization-based amplification methods can also be developed using the specific mutant ALC allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant ALC allele in biological samples or the determination of the zygosity status of plant material comprising a specific mutant ALC allele. More particularly, a preferred embodiment of the kit of the invention comprises at least two specific primers, as described above, for identification of a specific mutant ALC allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant ALC allele therein, as described above, for identification of a specific mutant ALC allele, or at least two or three specific probes for the determination of the zygosity status. Optionally, the kit can further comprise any other reagent (such as but not limited to hybridizing buffer, label) for identification of a specific mutant ALC allele in biological samples, using the specific probe.

The kit of the invention can be used, and its components can be specifically adjusted, for purposes of quality control (e.g., purity of seed lots), detection of the presence or absence of a specific mutant ALC allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant ALC allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant ALC allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant ALC allele, implying the presence of nucleic acids in the samples. Thus the methods referred to herein for identifying a specific mutant ALC allele in biological samples, relate to the identification in biological samples of nucleic acids that comprise the specific mutant ALC allele.

The present invention also relates to the combination of specific ALC alleles in one plant, to the transfer of one or more specific mutant ALC allele(s) from one plant to another plant, to the plants comprising one or more specific mutant ALC allele(s), the progeny obtained from these plants and to plant cells, plant parts, and plant seeds derived from these plants.

Thus, in one embodiment of the invention a method for combining two or more selected mutant ALC alleles in one plant is provided comprising the steps of:

(a) generating and/or identifying two or more plants each comprising one or more selected mutant ALC alleles, as described above,
(b) crossing a first plant comprising one or more selected mutant ALC alleles with a second plant comprising one or more other selected mutant ALC alleles, collecting F1 seeds from the cross, and, optionally, identifying an F1 plant comprising one or more selected mutant ALC alleles from the first plant with one or more selected mutant ALC alleles from the second plant, as described above,
(c) optionally, repeating step (b) until an F1 plant comprising all selected mutant ALC alleles is obtained,
(d) optionally,
identifying an F1 plant, which is homozygous or heterozygous for a selected mutant ALC allele by determining the zygosity status of the mutant ALC alleles, as described above, or
generating plants which are homozygous for one or more of the selected mutant ALC alleles by performing one of the following steps:

extracting doubled haploid plants from treated microspore or pollen cells of F1 plants comprising the one or more selected mutant ALC alleles, as described above, selfing the F1 plants comprising the one or more selected mutant ALC allele(s) for one or more generations (y), collecting F1 Sy seeds from the selfings, and identifying F1 Sy plants, which are homozygous for the one or more mutant ALC allele, as described above.

In another embodiment of the invention a method for transferring one or more mutant ALC alleles from one plant to another plant is provided comprising the steps of:

(a) generating and/or identifying a first plant comprising one or more selected mutant ALC alleles, as described above, or generating the first plant by combining the one or more selected mutant ALC alleles in one plant, as described above (wherein the first plant is homozygous or heterozygous for the one or more mutant ALC alleles), (b) crossing the first plant comprising the one or more mutant ALC alleles with a second plant not comprising the one or more mutant ALC alleles, collecting F1 seeds from the cross (wherein the seeds are heterozygous for a mutant ALC allele if the first plant was homozygous for that mutant ALC allele, and wherein half of the seeds are heterozygous and half of the seeds are azygous for, i.e. do not comprise, a mutant ALC allele if the first plant was heterozygous for that mutant ALC allele), and, optionally, identifying F1 plants comprising one or more selected mutant ALC alleles, as described above, (c) backcrossing F1 plants comprising one or more selected mutant ALC alleles with the second plant not comprising the one or more selected mutant ALC alleles for one or more generations (x), collecting BCx seeds from the crosses, and identifying in every generation BCx plants comprising the one or more selected mutant ALC alleles, as described above, (d) optionally, generating BCx plants which are homozygous for the one or more selected mutant ALC alleles by performing one of the following steps:

extracting doubled haploid plants from treated microspore or pollen cells of BCx plants comprising the one or more desired mutant ALC allele(s), as described above, selfing the BCx plants comprising the one or more desired mutant ALC allele(s) for one or more generations (y), collecting BCx Sy seeds from the selfings, and identifying BCx Sy plants, which are homozygous for the one or more desired mutant ALC allele, as described above.

In one aspect of the invention, the first and the second plant are Brassicaceae plants, particularly *Brassica* plants, especially *Brassica napus* plants or plants from another *Brassica* crop species. In another aspect of the invention, the first plant is a Brassicaceae plant, particularly a *Brassica* plant, especially a *Brassica napus* plant or a plant from another *Brassica* crop species, and the second plant is a plant from a Brassicaceae breeding line, particularly from a *Brassica* breeding line, especially from a *Brassica napus* breeding line or from a breeding line from another *Brassica* crop species. "Breeding line", as used herein, is a preferably homozygous plant line distinguishable from other plant lines by a preferred genotype and/or phenotype that is used to produce hybrid offspring.

In yet another embodiment of the invention, a method for making a plant, in particular a *Brassica* crop plant, such as a *Brassica napus* plant, of which the pod shatter resistance is increased but which preferably maintains an agronomically relevant threshability of the pods is provided comprising combining and/or transferring mutant ALC alleles according to the invention in or to one *Brassica* plant, as described above.

In one aspect of the invention, the plant is a *Brassica* plant comprising at least two non-naturally occurring mutant ALC genes wherein pod shatter resistance is increased while maintaining an agronomically relevant threshability of the pods by combining and/or transferring said two mutant ALC genes to a homozygous state according to the invention in or to the *Brassica* plant, as described above.

In still another embodiment of the invention, a method for making a hybrid *Brassica* crop seed or plant comprising at least two non-naturally occurring mutant ALC genes, in particular a hybrid *Brassica napus* seed or plant, of which the pod shatter resistance is increased but which maintains an agronomically relevant threshability of the pods is provided, comprising the steps of:

(a) generating and/or identifying a first plant comprising a first and a second selected mutant ALC gene in homozygous state and a second plant comprising a the same selected mutant ALC genes in homozygous state, as described above, (b) crossing the first and the second plant and collecting F1 hybrid seeds from the cross.

Sequences

ALC Genes

SEQ ID NO: 1: Genomic DNA sequence of ALC-GR1 from *Brassica napus*.

SEQ ID NO: 2: Genomic DNA sequence of ALC-GR2 from *Brassica napus*.

SEQ ID NO: 3: Genomic DNA sequence of ALC-GR3 from *Brassica napus*

SEQ ID NO: 4: Genomic DNA sequence of ALC-GR4 from *Brassica napus*.

SEQ ID NO: 5: Genomic DNA sequence of ALC-GR5 from *Brassica napus*.

SEQ ID NO: 6: Genomic DNA sequence of ALC-GR6 from *Brassica napus*.

SEQ ID NO: 7: Coding sequence of ALC-GR3 from *Brassica napus*.

SEQ ID NO: 8: Coding sequence of ALC-GR4 from *Brassica napus*.

SEQ ID NO: 9: Protein encoded by ALC-GR3 from *Brassica napus*.

SEQ ID NO: 10: Protein encoded by ALC-GR4 from *Brassica napus*.

Primers and Probes

SEQ ID NO: 11: Forward oligonucleotide for detection of ALC-GR3 and ALC-GR3-EMS07

SEQ ID NO: 12: Reverse oligonucleotide for detection of ALC-GR3 and ALC-GR3-EMS07

SEQ ID NO: 13: Oligonucleotide for detection of ALC-GR3-EMS07

SEQ ID NO: 14: Oligonucleotide for detection of ALC-GR3-EMS07

SEQ ID NO: 15: Oligonucleotide for detection of ALC-GR3

SEQ ID NO: 16: Forward oligonucleotide for detection of ALC-GR4 and ALC-GR4-EMS04

SEQ ID NO: 17: Reverse oligonucleotide for detection of ALC-GR4 and ALC-GR4-EMS04

SEQ ID NO: 18: Oligonucleotide for detection of ALC-GR4-EMS04

SEQ ID NO: 19: Oligonucleotide for detection of ALC-GR4

SEQ ID NO: 20: *B. napus* Simon ALC probe

Unless stated otherwise in the Examples, all recombinant DNA techniques are carried out according to standard molecular biological techniques as described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson at al. *PCR-Basics: From Background to Bench*, First Edition, Springer Verlag, Germany. Standard procedures for AFLP analysis are described in Vos et al. (1995, NAR 23:4407-4414) and in published EP patent application EP 534858.

EXAMPLES

Example 1—Isolation of the DNA Sequences of the ALC Genes

To determine the sequences of the ALC genes of an elite spring oilseed rape breeding line, a Bacterial Artificial Chromosome (BAC) library of the line was screened as follows:

1.1. Isolation of BAC Clones Comprising an ALC Sequence

To identify *Escherichia coli* colonies containing a BAC clone comprising an ALC sequence of the elite spring oilseed rape breeding line, a BAC library of the line (average clone size of more than 120 kb) arrayed as individual duplicated clones on high density nylon filters were screened by standard Southern hybridization procedures:

A probe with the sequence from *Brassica napus* Simon line (SEQ ID NO: 20) was labeled according to standard procedures used for hybridizing to the DNA on the nylon membrane.

Pre-hybridization was performed for 2 hour at 65° C. in 30 ml of the following hybridization buffer: 6×SSC (20×SSC contains 3.0 M NaCl, 0.3 M Na citrate, pH 7.0), 5×Denhardt's (100×Denhardt's contains 2% Ficoll, 2% Polyvinyl pyrollidone, 2% Bovine Serum Albumin), 0.5% SDS and 20 µg/ml denatured carrier DNA (single-stranded fish sperm DNA, with an average length of 120-3000 nucleotides).

Hybridization was performed under the following conditions:

The labeled probe (20 ng) was denaturated by heating for 5 minutes at 95° C. and chilling on ice for 5 minutes and added to 15 ml of hybridization buffer (same buffer as for the pre-hybridization), The hybridization was performed overnight at 65° C.

The blots were washed three times for 30 minutes at 65° C. in the hybridization tubes (once with 30 ml 6×SSC with 0.1% SDS and twice with 30 ml 2×SSC with 0.1% SDS) and one time for 10 minutes at 65° C. with 500 ml 2×SSC with 0.1% SDS in a box.

Kodak X-OMAT AR films were exposed to the radioactive blots for 4 hours at −70° C.

Based on the positive signals, 14 *E. coli* colonies containing a BAC clone comprising an ALC sequence were picked up by screening the BAC library from the elite spring oilseed rape breeding line (total no of positives: 44) (hereinafter called "positive colonies").

1.2. Isolation of BAC Clones Comprising a Full-Length ALC Sequence

To identify positive colonies comprising a BAC clone with a full-length genomic DNA sequence of one of the ALC genes, a Southern blot analysis was performed on BAC clone DNA isolated from the positive colonies and on genomic DNA isolated from *Brassica napus*:

BAC clone DNA was isolated through alkaline lysis as described in the art from the positive colonies grown up in 25 ml Luria Broth medium containing 25 µg/ml chloramphenicol.

Genomic DNA was isolated from leaf tissue of *B. napus* according to the cetyltrimethylammoniumbromide (CTAB) method (Doyle and Doyle, 1987, Phytochemistry Bulletin 19:11-15).

The DNA concentration of each preparation was estimated by comparing the band intensity of 1 µl of each sample to the band intensity of 1, 2, 4, 8 and 20 µl of a solution containing 25 ng/µl Lambda DNA (Life Technologies®) on a 1% TBE (Invitrogen®) agarose gel (Roche®) containing ethidiumbromide (ICN Biochemicals®).

100-200 ng of BAC clone DNA and 1.7 ng genomic DNA were digested with restriction enzyme AseI in a final reaction volume of 20 µl, applying conditions proposed by the manufacturer (New England Biolabs). The time of digestion and/or amount of restriction enzyme were adjusted to ensure complete digestion of the genomic DNA samples without non-specific degradation.

After digestion, 2 µl of loading dye containing RNase (12.5 ml 1% xylene cyanol FF; 12.5 ml 1% bromophenol blue water soluble indicator; 25 ml glycerol; 100 µl 0.5M EDTA pH8; 1 µl RNase (10 mg/ml)) was added to the digested DNA samples and the samples were incubated for 30 min at 37° C.

The samples were loaded on a 1% TAE agarose gel.

Phage Lambda DNA (Fermentas®) digested with PstI or 1 kbp DNA Ladder (Life Technologies) was included as size standard.

After electrophoresis, the DNA samples (digested BAC clone and genomic DNA) were transferred to a nylon membrane (Hybond-N+ Amersham Pharmacia Biotech®) by dry alkali capillary blotting.

The nylon membranes with digested BAC clone and genomic DNA were screened by standard Southern hybridization procedures as described above for the BAC library screenings, except that for the genomic DNA the Kodak XOMAT AR films were exposed to the radioactive blots for 2 days at −70° C.

Based on a comparison between the hybridization patterns obtained after digestion of BAC clone DNA of the identified positive colonies and of genomic DNA isolated from *Brassica napus* with restriction enzyme AseI and hybridization with the probe, the BAC clones were grouped in 6 groups and for each of the 6 groups a BAC clone was selected containing a full-length ALC sequence (named PPS02_ALC_GR1, PPS02_ALC_GR2, PPS02_ALC_GR3, PPS02_ALC_GR4, PPS02_ALC_GR5 and PPS02_ALC_GR6).

The ALC sequences comprised in the BAC clones of the selected positive colonies were determined by 454 BAC sequencing (Keygene).

Example 2—Characterization of ALC Gene Sequences from *Brassica napus*

The genomic DNA fragments were sequenced, and the genes and coding regions of the ALC sequences were determined with FgeneSH (Softberry, Inc. Mount Kisco, N.Y., USA) and est2genome (Rice et al., 2000, Trends in Genetics 16 (6): 276-277; Mott, 1997, Comput. Applic. 13:477-478). A sequence alignment of the identified ALC homologs are shown in FIG. 1.

PPS02_ALC_GR1 (SEQ ID NO: 1).

The BnALC sequence, as provided by FGeneSH, has five exons. This homolog probably represents a pseudogene or a highly divergent homolog.

PPS02_ALC_GR2 (SEQ ID NO: 2).

The ALC_GR2 sequence, as provided by FGeneSH, has three (3) exons and is truncated at both the N- and Carboxy-terminal regions when compared to the *Arabidopsis* homolog. This homolog probably represents a pseudogene or a highly divergent homolog.

PPS02_ALC_GR3 (SEQ ID NO: 3).

Blast-analysis and gene model prediction by est2genome, yields a gene-model that contains 5 exons. Both the FGeneSH and est2genome models produce CDSs without inappropriate stops. Further, CDSs derived from both FGeneSH and est2genome share approximately 80.0% identity with the presumptive *Arabidopsis* homolog.

PPS02_ALC_GR4 (SEQ ID NO: 4).

ALC_GR4 appears to contain a nearly complete homolog of ALC; while regions of identity are around 90% identical and FGeneSH prediction suggests the gene is intact, the organization of the gene is slightly different within 110 nts of the N-terminus and at the Carboxy-terminus. The Contig also has highly similar (80-97% identity), but short (<250 bp) regions of similarity to contigs 1, 2, 4, 9, 20, 21. With the exception of the 63 bp region shared with contig00002, none of these regions intersect the candidate ALC region.

The frame-1 translation of the FGeneSH-derived CDS has no pre-mature 'STOPS' and the CDS shares 82.14% identity with the *Arabidopsis* homolog. Further, ClustalW alignment reveals conservation of structure with AtALC

PPS02_ALC_GR5 (SEQ ID NO: 5).

A region with limited similarity to AtALC was found, suggesting that this gene is not a close homolog of AtALC.

PPS02_ALC_GR6 (SEQ ID NO: 6).

A region with limited similarity to AtALC was found. The combination of a low-level of observed similarity and the gene-models predicted by both FGeneSH and est2genome suggest that this sequence region is not a close homolog of AtALC.

With the blast database from BGI Solexa of *B. rapa* (AA), *B. oleracea* (CC) and *B. napus* (AACC) indicated that the PPS02_ALC_GR3 sequence originated from the A genome, and the sequence PPS02_ALC_GR4 from the C genome. The other ALC sequences could not clearly be allocated to the A or the C genome.

Example 3—Expression of *Brassica* ALC Genes

To analyze the expression of the different ALC genes in different tissues, RT-PCR assays specific for each ALC gene were performed on total RNA isolated from *Brassica napus* dehiscence zone tissue. The results indicated that only PPS02_ALC_GR3 and PPS02_ALC_GR4 genes were expressed in dehiscence zone tissue.

The expression of PPS-2_ALC_GR3 and PPS02_ALC_GR4 in whole pod tissue was analyzed in more detail at different stages during pod development using RT-PCR on total RNA isolated from *Brassica napus* whole pod tissue without seeds. FIG. 2 shows that relative expression of PPS-2_ALC_GR3 decreases over time, whereas relative expression of PPS-2_ALC_GR4 increases over time.

Example 4—Generation and Isolation of Mutant ALC Alleles (alc)

Mutations in the ALC genes identified in Example 1 were generated and identified as follows:

30,000 seeds from an elite spring oilseed rape breeding line (M0 seeds) were preimbibed for two hours on wet filter paper in deionized or distilled water. Half of the seeds were exposed to 0.8% EMS and half to 1% EMS (Sigma: M0880) and incubated for 4 hours.

The mutagenized seeds (M1 seeds) were rinsed 3 times and dried in a fume hood overnight. 30,000 M1 plants were grown in soil and selfed to generate M2 seeds. M2 seeds were harvested for each individual M1 plant.

Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).

The DNA samples were screened for the presence of point mutations in the ALC genes causing the introduction of STOP codons and an other amino acid in the protein-encoding regions of the ALC genes or the substitution of amino acids in the ALC proteins, particularly in the bHLH domain of the ALC proteins, by direct sequencing by standard sequencing techniques (Agowa) and analyzing the sequences for the presence of the point mutations using the NovoSNP software (VIB Antwerp).

The mutant ALC alleles (alc) as depicted in Table 2 were thus identified.

TABLE 2

STOP codon and weak mutation (encodes for other aminoacid) and splice mutations in ALC

| Position | Sample | Plant Name | WT sequence | MUT sequence | Allele | Type |
|---|---|---|---|---|---|---|
| EMS mutants for ALC-GR3 | | | | | | |
| 521 | EMS_DS_0061a02_tar9g3F | | AG]GT | AA]GT | ALC-GR3-EMS01 | FULL (SPLICE) |
| 496 | EMS_DS_0063d08_tar9g3F | POSH127 | GCA | GTA | ALC-GR3-EMS02 | WEAK (Ala→Val) |
| 504 | EMS_DS_0061e05_tar9g3F | POSH128 | CAC | TAC | ALC-GR3-EMS03 | WEAK (His→Tyr) |
| 636 | EMS_DS_0080d06_tar9g3F | POSH129 | GCA | GTA | ALC-GR3- | WEAK |

TABLE 2-continued

STOP codon and weak mutation (encodes for other aminoacid) and splice mutations in ALC

| Position | Sample | Plant Name | WT sequence | MUT sequence | Allele | Type |
|---|---|---|---|---|---|---|
| 654 | EMS_DS_0057c09_tar9g3F | POSH130 | CCC | CTC | ALC-GR3-EMS04 | WEAK (Ala→Val) |
| | | | | | ALC-GR3-EMS05 | (Pro→Leu) |
| 667 | EMS_DS_0080f03_tar9g3F | | AA]GG | AA]AG | ALC-GR3-EMS06 | FULL (SPLICE) |
| 668 | EMS_DS_0043d08_tar9g3F | POSH131 | AG]GT | AG]AT | ALC-GR3-EMS07 | FULL (SPLICE) |
| 751 | EMS_DS_0078b09_tar9g3F | POSH132 | GAT | AAT | ALC-GR3-EMS08 | WEAK (Asp→Asn) |
| 781 | EMS_DS_0055h04_tar9g3F | | GAA | AAA | ALC-GR3-EMS09 | WEAK (Glu→Lys) |
| EMS mutants for ALC-GR4 | | | | | | |
| 646 | EMS_DS_0085e01 | POSH134 | CAG | TAG | ALC-GR4-EMS04 | FULL (STOP) |
| 755 | EMS_DS_0085a06 | POSH135 | AG]AC | AA]AC | ALC-GR4-EMS05 | WEAK (SPLICE)* |
| 807 | EMS_DS_0082a03 | | CAA | TAA | ALC-GR4-EMS06 | FULL (STOP) |
| 765 | EMS_DS_0062d08 | | GCC | ACC | ALC-GR4-EMS07 | WEAK (Ala→Thr) |
| 641 | EMS_DS_0072f08 | POSH136 | GCT | GTT | ALC-GR4-EMS08 | WEAK (Ala→Val) |
| 780 | EMS_DS_0073a02 | POSH137 | GAA | AAA | ALC-GR4-EMS09 | WEAK (Glu→Lys) |
| 784 | EMS_DS_0080f05 | | GCT | GTT | ALC-GR4-EMS10 | WEAK (Ala→Val) |
| 773 | EMS_DS_0084f07 | POSH138 | ATG | ATA | ALC-GR4-EMS11 | WEAK (Met→Ile) |
| 628 | EMS_DS_0093e05 | POSH139 | GAG | AAG | ALC-GR4-EMS12 | WEAK (Glu→Lys) |
| 821 | EMS_DS_0040d02_tar9g4R | POSH133 | AG]GT | AA]GT | ALC-GR4-EMS01 | FULL (SPLICE) |
| 822 | EMS_DS_0047c09_tar9g4R | | AG]GT | AG]AT | ALC-GR4-EMS02 | FULL (SPLICE) |

*ALC-GR4-EMS05 is considered a WEAK allele, as for this splice site mutant it is predicted that a next donor splice site, which is 9 nts further downstream, is used in the mutant, resulting in an mRNA with a 9 nt deletion, encoding a protein with a 3 AA deletion at position 128-130 of the protein.

Example 5—Identification of a *Brassica* Plant Comprising a Mutant *Brassica* ALC Allele

*Brassica* plants comprising the mutations in the ALC genes identified in Example 4 were identified as follows:
For each mutant ALC gene identified in the DNA sample of an M2 plant, at least 50 M2 plants derived from the same M1 plant as the M2 plant comprising the ALC mutation were grown and DNA samples were prepared from leaf samples of each individual M2 plant.
The DNA samples were screened for the presence of the identified point ALC mutation as described above in Example 4.
Heterozygous and homozygous (as determined based on the electropherograms) M2 plants comprising the same mutation were selfed and M3 seeds were harvested.

Example 6—Analysis of the Fruit Dehiscence Properties of *Brassica* Plants Comprising a Mutant *Brassica* ALC Gene To determine the correlation between the presence of mutant ALC genes in *Brassica* plants and the fruit dehiscence properties of the *Brassica* plants, the fruit dehiscence properties of *Brassica* plants comprising a mutant ALC gene were analyzed as follows:
To examine whether and how the fruit valve margins and the dehiscence properties of seed pods were affected by mutations in ALC, alc fruit was compared to wild-type fruit using the following macroscopic tests:
a) Inspection of the seed pods and plants in general with naked eye to determine differences in the phenotype of the pods and plants caused by the presence of certain mutant ALC alleles.
b) Random Impact Test (RIT) to determine the increase in pod shatter resistance caused by the presence of certain mutant ALC alleles: The level of pod shatter resistance of *Brassica* lines comprising the mutant ALC alleles and *Brassica* lines comprising the corresponding wild type ALC alleles was compared in a quantitative way by determining the half life of samples of pods from both lines according to Bruce et al. (2002, Biosystems Eng 81(2): 179-184). More specifically, two replicate samples of 20 intact mature pods from each line were subjected to a RIT. 20 pods were placed together with six steel balls of 12.5 mm diameter in a cylindrical container of diameter 20 cm with its axis vertical. The container was then subjected to simple harmonic motion of frequency 4.98 Hz and of stroke 51 mm in the horizontal plane. The pods, checked for soundness before the test, were shaken for cumulative times of 10, 20, 40, and, if more than 50% of pods remained intact, 80 s. The drum was opened after each period and the number of closed pods counted. The pods were examined and classed as "closed" if the dehiscence zone of both valves was still closed. Thus the pods were classed as "opened" if one or both of the valves was detached, so that the seed had been released. If the majority of the pods was broken or damaged without opening of the dehiscence zone, the sample was marked "uncountable". To give each point equal weighing, the data were made evenly spaced in the independent variable, time, by adding 1 and taking $\log_{10}$. The percentage of pods opened p was transformed by the logit transformation, i.e. logit $p=\log_e(p/100-p)$. A linear model was then fitted to the transformed time and percentage data and used to estimate the half-life.

6.1. Correlation Between the Presence of One or Two Mutant *Brassica* ALC Genes in *Brassica* Plants and the Fruit Dehiscence Properties of Those *Brassica* Plants To determine the correlation between the presence one or two mutant ALC genes in a *Brassica* plant and the fruit dehiscence properties of the *Brassica* plant, the *Brassica* plants identified in Example 5, and/or progeny thereof, comprising the mutant ALC alleles, were crossed with each other and the fruit dehiscence properties of the progeny *Brassica* plants was analyzed as described above.

Plant Material:

Homozygous single mutant plants in ALC-GR3 (alleles ALC-GR3-EMS02, ALC-GR3-EMS03, ALC-GR3-EMS04, ALC-GR3-EMS07 and ALC-GR3-EMS08) and in ALC-GR4 (allele ALC-GR4-EMS01), and homozygous double mutant plants in ALC-GR3 and ALC-GR4 (alleles ALC-GR3-EMS02, ALC-GR3-EMS03, ALC-GR3-EMS04, ALC-GR3-EMS05, ALC-GR3-EMS07, ALC-GR3-EMS08, ALC-GR4-EMS04, ALC-GR4-EMS05, ALC-GR4-EMS08, ALC-GR4-EMS09, ALC-GR4-EMS11 and ALC-GR4-EMS12).

Figure 3:
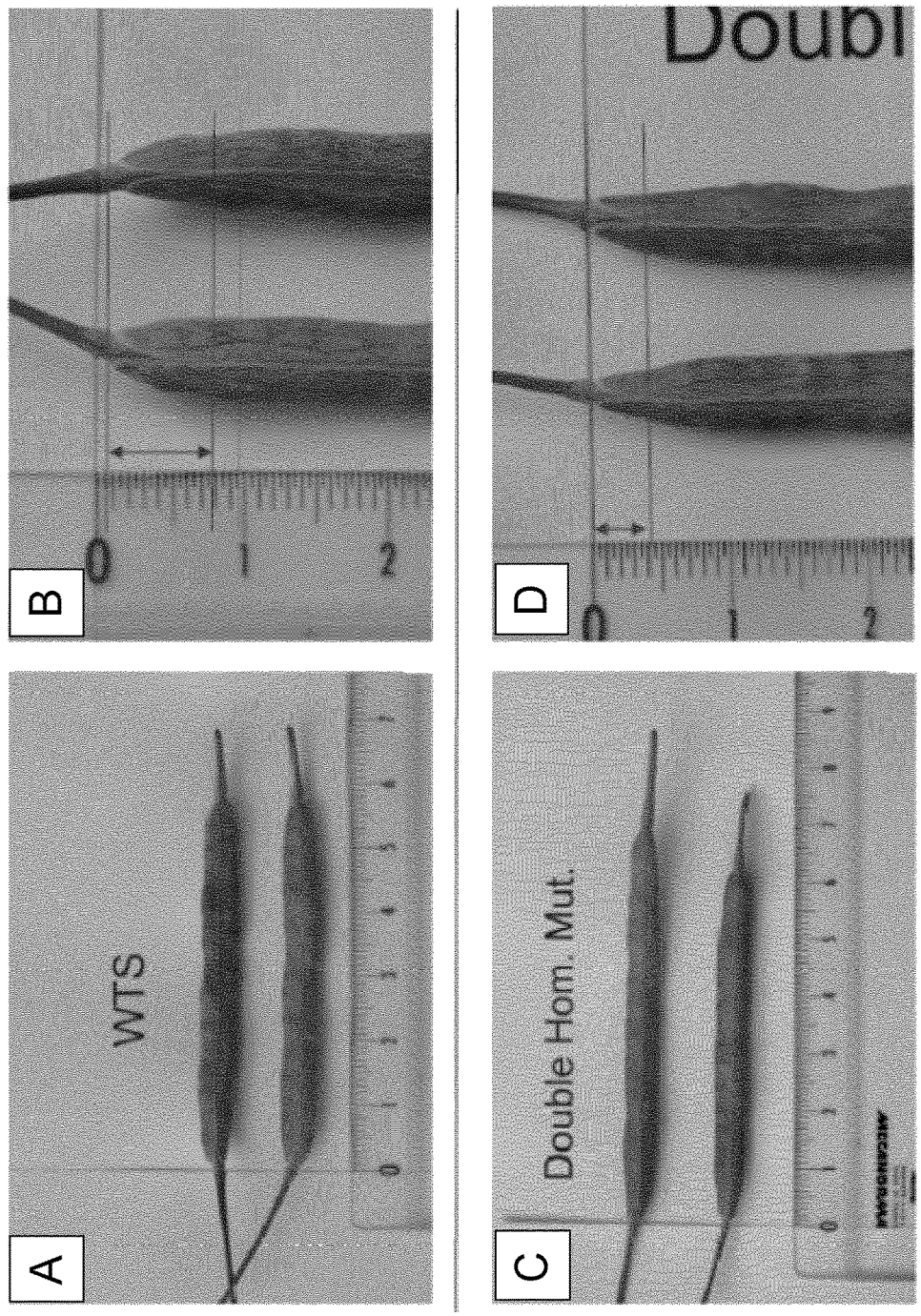
FIG. 3: Seed pods from wild-type (A and B) and mutant ALC sibling plants homozygous for the POSH131 and the POSH139 alleles, BC2S1 generation (C and D).

Macroscopical Evaluation:

a) Inspection of the seed pods and plants with naked eye.
   Seed pods from wild-type (A and B) and mutant ALC sibling plants homozygous for the POSH131 and the POSH139 alleles showed an altered pod morphology as compared to pods from wild-type ALC sibling plants (see FIG. 3). More specifically, the distance between point of attachment of pod with pedicel and point of convergence of layers between valves is higher in the mutants than in the wild-type pods.

b) Random Impact Test:
   As shown in Table 3, the half life of pod samples ('LD50') was not significantly higher for pods from homozygous single mutants as compared to wild-type.
   Table 3 further shows that for the double mutants the LD50 value was not significantly different between wild-type and mutant when the mutants in both genes were 'weak' mutants. Also when the mutant in one gene was 'weak' and the mutant in the other gene was a full knock-out, no significant difference if LD50 with wild-type was observed. In only one case, where mutants in both genes were full knock-outs (POSH131/POSH134), the LD50 was significantly higher than for wild type. This shows that full knock-out in both ALC-GR3 and ALC-GR4 genes are required in order to obtain podshatter resistance.

TABLE 3

| RIT values of ALC single and double mutants | | | | | |
|---|---|---|---|---|---|
| Plant | LD50 s. | lld50 | uld50 | Corrected Lower 95% | Corrected Upper 95% |
| ALC single mutants | | | | | |
| POSH127 wildtype | 4.765 | 3.478 | 6.244 | 1.287 | 1.479 |
| POSH127 mutant | 4.368 | 3.084 | 5.878 | 1.284 | 1.51 |
| POSH128 wildtype | 9.636 | 8.26 | 11.125 | 1.376 | 1.489 |
| POSH128 mutant | 5.127 | 3.84 | 6.581 | 1.287 | 1.454 |
| POSH129 wildtype | 5.127 | 3.84 | 6.581 | 1.287 | 1.454 |
| POSH129 mutant | 6.643 | 5.356 | 8.037 | 1.287 | 1.394 |
| POSH131 wildtype | 8.177 | 6.865 | 9.587 | 1.312 | 1.41 |
| POSH131 mutant | 5.127 | 3.84 | 6.581 | 1.287 | 1.454 |
| POSH132 wildtype | 4.368 | 3.084 | 5.878 | 1.284 | 1.51 |
| POSH132 mutant | 8.177 | 6.865 | 9.587 | 1.312 | 1.41 |
| POSH133 wildtype | 5.779 | 4.493 | 7.198 | 1.286 | 1.419 |
| POSH133 mutant | 4.765 | 3.478 | 6.244 | 1.287 | 1.479 |
| ALC double mutants | | | | | |
| POSH127/POSH134 wildtype | 6.99 | 1.546 | 8.95 | 5.444 | 1.96 |
| POSH127/POSH134 mutant | 10.79 | 8.033 | 12.9 | 2.757 | 2.11 |
| POSH128/POSH134 wildtype | 5.6 | 2.572 | 7.77 | 3.028 | 2.17 |
| POSH128/POSH134 mutant | 7.23 | 4.14 | 9.58 | 3.09 | 2.35 |
| POSH129/POSH134 wildtype | 11.41 | 8.446 | 13.88 | 2.964 | 2.47 |
| POSH129/POSH134 mutant | 11.26 | 7.86 | 14.46 | 3.4 | 3.2 |
| POSH130/POSH134 wildtype | 10.18 | 6.921 | 12.53 | 3.259 | 2.35 |
| POSH130/POSH134 mutant | | | | | |
| POSH131/POSH134 wildtype | 10.63 | 7.259 | 13.58 | 3.371 | 2.95 |
| POSH131/POSH134 mutant | 21.42 | 17.671 | 26.17 | 3.749 | 4.75 |
| POSH131/POSH135 wildtype | 10.63 | 7.259 | 13.58 | 3.371 | 2.95 |
| POSH131/POSH135 mutant | 12.44 | 9.221 | 15.68 | 3.219 | 3.24 |
| POSH131/POSH136 wildtype | 9.68 | 6.34 | 12.42 | 3.34 | 2.74 |
| POSH131/POSH136 mutant | 11.42 | 8.109 | 14.36 | 3.311 | 2.94 |
| POSH131/POSH137 wildtype | 11.42 | 8.109 | 14.36 | 3.311 | 2.94 |
| POSH131/POSH137 mutant | 8.62 | 5.23 | 10.95 | 3.39 | 2.33 |
| POSH131/POSH138 wildtype | 8.98 | 5.556 | 11.12 | 3.424 | 2.14 |
| POSH131/POSH138 mutant | 8.98 | 5.555 | 11.12 | 3.425 | 2.14 |
| POSH131/POSH139 wildtype | 9.7 | 6.555 | 11.74 | 3.145 | 2.04 |
| POSH131/POSH139 mutant | 15.08 | 11.673 | 20.59 | 3.407 | 5.51 |
| POSH132/POSH134 wildtype | 14.2 | 10.917 | 17.73 | 3.283 | 3.53 |
| POSH132/POSH134 mutant | 11.59 | 8.481 | 14.28 | 3.109 | 2.69 |

Example 7—Detection and/or Transfer of Mutant ALC Genes into (Elite) *Brassica* Lines To Select For Plants Comprising a Point Mutation in an ALC allele, direct sequencing by standard sequencing techniques known in the art, such as those described in Example 4, can be used. Alternatively, PCR assays can be developed to discriminate plants comprising a specific point mutation in an ALC allele from plants not comprising that specific point mutation. The following discriminating Taqman PCR assays were thus developed to detect the presence or absence and the zygosity status of the mutant alleles identified in Example 4 (see Table 2):

Template DNA:
  Genomic DNA isolated from leaf material of homozygous or heterozygous mutant *Brassica* plants (comprising a mutant ALC allele, called hereinafter "ALC-Xx-EMSXX").
Wild type DNA control: Genomic DNA isolated from leaf material of wild type *Brassica* plants (comprising the wild type equivalent of the mutant ALC allele, called hereinafter "WT").

Positive DNA control: Genomic DNA isolated from leaf material of homozygous mutant *Brassica* plants known to comprise ALC-Xx-EMSXX.

Primers and probes for the mutant and corresponding wild-type target ALC gene are indicated in Table 4.

Generally, each primer set consists of two primers amplifying both the mutant and the wild type target gene, one probe specific for the nucleotide difference between mutant and wild-type, in which the FAM probe contains the nucleotide for the mutant, and the VIC probe contains the nucleotide from wild-type.

TABLE 4

Primers and probes for detection of wild-type and mutant ALC alleles:

| Type | Sequence | Allele | Name | SEQ ID NO: |
|---|---|---|---|---|
| Plant: POSH 127 | | | | |
| Primer 1 | TGTTTTTGCTTGGTAATGGTTAACAC | | | 54 |
| Primer 2 | AAGACGAAACCTTTTCAGACAAGTTG | | | 23 |
| FAM probe | AAACATTGATGTACAGTTC | FAM allele | ALC-GR3-EMS02 | 60 |
| VIC probe | AAGAGAAACATTGATGCACA | VIC allele | WT | 24 |
| Plant: POSH 128 | | | | |
| Primer 1 | AAATCAAGAATCTTAAAAGGATAAAGACG | | | 21 |
| Primer 2 | TGCTTGGTAATGGTTAACACAACAC | | | 51 |
| FAM probe | CAAGTTGTAGAACTGTG | FAM allele | ALC-GR3-EMS03 | 38 |
| VIC probe | ACAAGTTGTGGAACTG | VIC allele | WT | 28 |
| Plant: POSH 128_TQ1 | | | | |
| Primer 1 | TGTTTTTGCTTGGTAATGGTTAACAC | | | 54 |
| Primer 2 | CAAATCAAGAATCTTAAAAGGATAAAGACG | | | 37 |
| FAM probe | TGATGCACAGTTCAACAA | FAM allele | | 49 |
| VIC probe | TGCACAGTTCGACAAC | VIC allele | | 50 |
| Plant: POSH 129 | | | | |
| Primer 1 | AGGAGGAGGAGCAAGATCAATG | | | 11 |
| Primer 2 | CTGAAGGATAAAATGTCGAACTTTATATTTAC | | | 43 |
| FAM probe | AGAAAATGAAAGTATTGCAG | FAM allele | ALC-GR3-EMS04 | 30 |
| VIC probe | AGAAAATGAAAGCATTGC | VIC allele | WT | 29 |
| Plant: POSH 130 | | | | |
| Primer 1 | AGGAGGAGGAGCAAGATCAATG | | | 11 |
| Primer 2 | AACAAAATAAATGCTTTTCACGACAG | | | 22 |
| FAM probe | AGAAACTGATACTCAATTC | FAM allele | ALC-GR3-EMS05 | 32 |
| VIC probe | TGATACCCAATTCC | VIC allele | WT | 48 |
| Plant: POSH 131 | | | | |
| Primer 1 | AGGAGGAGGAGCAAGATCAATG | | | 11 |
| Primer 2 | AACAAAATAAATGCTTTTCACGACAC | | | 12 |
| FAM probe | TCGAACTTTATATTTATCTTGTTG | FAM allele | ALC-GR3-EMS07 | 13 |
| VIC probe | TGTCGAACTTTATATTTACCTTG | VIC allele | WT | 15 |
| Plant: POSH131_TQ1 | | | | |
| Primer 1 | AGGAGGAGGAGCAAGATCAATG | | | 11 |
| Primer 2 | AACAAAATAAATGCTTTTCACGACAC | | | 12 |
| FAM probe | CGAACTTTATATTTATCTTGTTG | FAM allele | ALC-GR3-EMS07 | 14 |
| VIC probe | TGTCGAACTTTATATTTACCTTG | VIC allele | WT | 15 |
| Plant: POSH 132 | | | | |
| Primer 1 | CTTCAGAACTGAGTGTCGTGAAAAG | | | 44 |
| Primer 2 | CAGTCATTAAAAGTTAATCAGATGTTTGGT | | | 41 |
| FAM probe | TTTGGTAGACAAATAAG | FAM allele | ALC-GR3-EMS08 | 58 |
| VIC probe | TTGGTAGACAGATAAGG | VIC allele | WT | 57 |
| Plant: POSH132_TQ1 | | | | |
| Primer 1 | CTTCAGAACTGAGTGTCGTGAAAAG | | | 44 |
| Primer 2 | CAGTCATTAAAAGTTAATCAGATGTTTGGT | | | 41 |
| FAM probe | TGGTAGACAAATAAG | FAM allele | ALC-GR3-EMS08 | 52 |
| VIC probe | TGTTTGGTAGACAGATAA | VIC allele | WT | 53 |
| Plant: POSH 133 | | | | |
| Primer 1 | TTCAGAACTCAGTTGTGAGATACATTTG | | | 55 |
| Primer 2 | TCATCAAGTTAATCAGATGTTTGGG | | | 47 |
| FAM probe | CTTCAGTTTCAAGTTC | FAM allele | ALC-GR4-EMS01 | 45 |
| VIC probe | TTCAGTTTCAGGTTCTT | VIC allele | WT | 56 |

TABLE 4-continued

Primers and probes for detection of wild-type and mutant ALC alleles:

| Type | Sequence | Allele | Name | SEQ ID NO: |
|---|---|---|---|---|
| Plant: POSH 134 | | | | |
| Primer 1 | AGAGGAGGAGGAGCAAGATCAAC | | | 16 |
| Primer 2 | AAAGATAAAAAGTCGAACTTGGTATTTACC | | | 17 |
| FAM probe | AGCTTTGTAGAAACTG | FAM allele | ALC-GR4-EMS04 | 18 |
| VIC probe | AAAGCTTTGCAGAAAC | VIC allele | WT | 19 |
| Plant: POSH 135 | | | | |
| Primer 1 | ATTCATCAAGTTAATCAGATGTTTGGG | | | 36 |
| Primer 2 | TTCAGAACTCAGTTGTGAGATACATTTG | | | 55 |
| FAM probe | AGGCCTTTTCTGTTTACAA | FAM allele | ALC-GR4-EMS05 | 35 |
| VIC probe | CCTTTTCTGTCTACAAAA | VIC allele | WT | 42 |
| Plant: POSH 136 | | | | |
| Primer 1 | CACACCTTGTCTGAAAAGGTTTTG | | | 40 |
| Primer 2 | AAGATAAAAAGTCGAACTTGGTATTTACC | | | 25 |
| FAM probe | AGAAAATGAAAGTTTTGCAG | FAM allele | ALC-GR4-EMS08 | 31 |
| VIC probe | AAAATGAAAGCTTTGC | VIC allele | WT | 59 |
| Plant: POSH 137 | | | | |
| Primer 1 | TTCAGAACTCAGTTGTGAGATACATTTG | | | 55 |
| Primer 2 | ATTCATCAAGTTAATCAGATGTTTGGG | | | 36 |
| FAM probe | CAATGCTTGATAAAGCTA | FAM allele | ALC-GR4-EMS09 | 39 |
| VIC probe | AATGCTTGATGAAGCTA | VIC allele | WT | 27 |
| Plant: POSH 138 | | | | |
| Primer 1 | TCATCAAGTTAATCAGATGTTTGGG | | | 47 |
| Primer 2 | TTCAGAACTCAGTTGTGAGATACATTTG | | | 55 |
| FAM probe | AGCTTCATCAAGTATTG | FAM allele | ALC-GR4-EMS11 | 34 |
| VIC probe | TAGCTTCATCAAGCATTGA | VIC allele | WT | 46 |
| Plant: POSH 139 | | | | |
| Primer 1 | AGATAAAAAGTCGAACTTGGTATTTACCAC | | | 33 |
| Primer 2 | CACACCTTGTCTGAAAAGGTTTTG | | | 40 |
| FAM probe | AAGCTTTCATTTTCTTGTTG | FAM allele | ALC-GR4-EMS12 | 26 |
| VIC probe | AAGCTTTCATTTTCTCGTTG | VIC allele | WT | 61 |

In summary, the invention relates to the following embodiments:

1. A *Brassica* plant, or a cell, part, seed or progeny thereof, comprising at least one ALC gene, characterized in that all ALC genes are full knock-out alc genes.
2. A plant according to paragraph 1, of which at least one ALC gene is a non-naturally occurring full knock-out alc gene.
3. A plant according to paragraph 2, comprising an A genome, a C genome, or both an A genome and a C genome, wherein said A genome contains one non-naturally occurring full knock-out alc gene and wherein said C genome contains one non-naturally occurring full knock-out alc gene.
4. A plant according to paragraph 3, comprising both an A genome and a C genome.
5. A plant according to paragraph 4, comprising four naturally occurring full knock-out alc genes.
6. A plant according to any one of the preceding paragraphs, wherein one or more of the non-naturally occurring full knock-out alc genes is a mutated version of the native ALC gene selected from the group consisting of:
   (a) a nucleic acid molecule which comprises at least 90% sequence identity to SEQ ID NO: 3;
   (b) a nucleic acid molecule which comprises at least 90% sequence identity to SEQ ID NO: 4;
   (c) a nucleic acid molecule encoding an amino acid sequence comprising at least 90% sequence identity to SEQ ID NO: 9;
   (d) a nucleic acid molecule encoding an amino acid sequence comprising at least 90% sequence identity to SEQ ID NO: 10,
   wherein said mutant alc gene comprises a mutated DNA region consisting of one or more inserted, deleted or substituted nucleotides compared to a corresponding wild-type DNA region in the functional ALC gene and wherein said mutant alc allele does not encode a functional ALC protein.
7. A plant according to any one of the preceding paragraphs, wherein the non-naturally occurring full knock-out alc genes contain a mutation selected from the group:
   (a) Premature stopcodon
   (b) Mutated splice site
8. A plant according to paragraph 6, wherein the non-naturally occurring full knock-out alc gene is selected from the group:
   (a) ALC gene from the A genome containing a mutated splice site
   (b) ALC gene from the C genome containing a premature stopcodon
9. A plant according to paragraph 8, wherein the non-naturally occurring full knock-out alc gene is selected from the group:
   a) ALC gene from the A genome containing a mutated splice site characterized by a G to A substitution at position 668 of SEQ ID NO: 3;
   b) ALC gene from the C genome containing a premature stopcodon characterized by a C to T substitution at position 646 of SEQ ID NO: 4.

10. A plant according to any one of the preceding paragraphs, which is homozygous for the full knock-out alc genes.
11. A plant according to any one of the preceding paragraphs, which produces no functional ALC protein.
12. A *Brassica* plant with significantly reduced seed shattering which is obtained by a method comprising downregulation of ALC gene expression.
13. The plant according to paragraph 12, wherein said method comprises the following steps:
    (a) providing plant cells with one or more chimeric genes to create transgenic plant cells, said chimeric genes comprising the following operably linked DNA fragments
        i. a plant-expressible promoter;
        ii. a DNA region, which when transcribed yields an RNA molecule inhibitory to one or more ALC genes encoding a functional ALC protein;
        iii. a 3' end region involved in transcription termination and polyadenylation;
    (b) regenerating a population of transgenic plant lines from said transgenic plant cell; and
    (c) identifying a plant line with increased podshatter resistance within said population of transgenic plant lines.
14. The plant according to paragraph 13, wherein said ALC inhibitory RNA molecule comprises a nucleotide sequence of at least 20 consecutive nucleotides selected from the nucleotide SEQ ID NO: 3 and of SEQ ID NO: 4 or the complement thereof
15. The plant according to paragraph 14, wherein said ALC inhibitory RNA molecule comprises a nucleotide sequence of at least 20 consecutive nucleotides selected from SEQ ID NO: 7 and SEQ ID NO: 8 or the complement thereof
16. The plant according to any one of paragraphs 14 to 15, wherein said chimeric gene further comprises a DNA region encoding a self-splicing ribozyme between said DNA region coding for said ALC inhibitory RNA molecule and said 3' end region.
17. The plant according to paragraph 16, wherein said ALC inhibitory RNA comprises a sense region comprising a nucleotide sequence of at least 20 consecutive nucleotides present in both SEQ ID NO: 7 and of SEQ ID NO: 8 and an antisense region comprising a nucleotide sequence of at least 20 consecutive nucleotides of the complement of the nucleotide sequence present in both SEQ ID NO: 7 and of SEQ ID NO: 8, wherein said sense and antisense region are capable of forming a double stranded RNA region comprising said at least 20 consecutive nucleotides.
18. The plant according to paragraph 13, wherein said transcribed DNA yields a pre-miRNA molecule which is processed into a miRNA capable of guiding the cleavage of mRNA transcribed from said ALC genes.
19. A plant according to any one of paragraphs 12 to 18, which produces an amount of functional ALC protein which is at least 90% lower compared to the amount of functional ALC protein produced by a corresponding plant not comprising the RNA molecule inhibitory to ALC genes.
20. A plant according to any one of the preceding paragraphs, which is a plant from a *Brassica* crop species, preferably *Brassica napus, Brassica juncea, Brassica carinata, Brassica rapa, Brassica oleracea* or *Brassica nigra*.
21. A plant according to any one of the preceding paragraphs, which is a plant from a *Brassica* oilseed species, preferably *Brassica napus, Brassica juncea* or *Brassica rapa*.
22. A plant according to any one of the preceding paragraphs, wherein the seed shattering of the plant is significantly reduced or delayed compared to the seed shattering of a corresponding plant not comprising full knock-out alc genes.
23. A plant according to paragraph 22, which maintains an agronomically relevant threshability of the pods.
24. A plant according to any one of the preceding paragraphs, wherein the seed yield of the plant is increased, preferably significantly increased compared to the seed yield of a corresponding plant not comprising non-naturally occurring full knock-out alc genes.
25. A seed pod obtainable from a plant according to any one of paragraphs 1 to 24.
26. A full knock-out allele of an ALC gene, wherein the full knock-out alc allele is a mutated version of the native ALC gene selected from the group consisting of:
    (a) a nucleic acid molecule which comprises at least 90% sequence identity to SEQ ID NO: 3 or SEQ ID NO: 4;
    (b) a nucleic acid molecule encoding an amino acid sequence comprising at least 90% sequence identity to SEQ ID NO: 9 or SEQ ID NO: 10,
    wherein said mutant alc allele comprises a mutated DNA region consisting of one or more inserted, deleted or substituted nucleotides compared to a corresponding wild-type DNA region in the functional ALC gene and wherein said mutant alc allele does not encode a functional ALC protein.
27. A full knock-out allele of an ALC gene, wherein the ALC gene from A genome contains a mutated splice site characterized by a G to A substitution at position 668 of SEQ ID NO: 3, and wherein the ALC gene from C genome contains a premature stopcodon characterized by a C to T substitution at position 646 of SEQ ID NO: 4.
28. A method for identifying a full knock-out alc allele according to paragraph 26 or 27 in a biological sample comprising determining the presence of a full knock-out alc specific region in a nucleic acid present in the biological sample.
29. The method according to paragraph 28, which further comprises subjecting the biological sample to an amplification reaction or a hybridization assay using a kit comprising a set of primers or probes.
30. A kit for identifying a full knock-out alc allele according to paragraph 26 or 27 in a biological sample, comprising a set of primers or probes consisting of:
    a set of primers, wherein one of said primers specifically recognizes a DNA region 5' flanking the mutated DNA region of the full knock-out alc allele and the other of said primers or probes specifically recognizes a DNA region 3' flanking the mutated DNA region of the full knock-out alc allele;
    a probe which specifically recognizes the joining region between a DNA region 5' or 3' flanking the mutated DNA region and the mutated DNA region of the full knock-out alc allele and which is labeled with FAM™ dye;
    a probe which specifically recognizes the wild-type sequence corresponding to the mutation region of the full knock-out allele and which is labeled with VIC™ dye.

31. The kit according to paragraph 30, wherein
   said 5' or 3' flanking region comprises the nucleotide sequence of SEQ ID NO: 3 from nucleotide 1 to 667 or 669 to 1201 or of the complement thereof, respectively; said mutation region has the nucleotide sequence of nucleotide 668 of SEQ ID NO: 3 or of the complement thereof; and said joining region comprises the nucleotide sequence of SEQ ID NO: 3 from nucleotide 1 to 668 or 668 to 1201 or of the complement thereof, respectively, or
   said 5' or 3' flanking region comprises the nucleotide sequence of SEQ ID NO: 4 from nucleotide 1 to 645 or 647 to 1207 or of the complement thereof, respectively; said mutation region has the nucleotide sequence of nucleotide 646 of SEQ ID NO: 4 or of the complement thereof; and said joining region comprises the nucleotide sequence of SEQ ID NO: 4 from nucleotide 1 to 646 or 646 to 1207 or from the complement thereof, respectively, or 32. The kit according to paragraph 30 or 31, wherein said set of primers or probes is selected from the group consisting of:
   a set of primers comprising one primer comprising the sequence of SEQ ID NO: 11 and/or one primer comprising the sequence of SEQ ID NO: 12,
   a set of primers comprising one primer comprising the sequence of SEQ ID NO: 17 and/or one primer comprising the sequence of SEQ ID NO: 18,
   a set of probes comprising one probe comprising the sequence of SEQ ID NO: 13 which is labeled with a FAM™ dye, and/or one probe comprising the sequence of SEQ ID NO: 15 which is labeled with a VIC™ dye,
   a set of probes comprising one probe comprising the sequence of SEQ ID NO: 14 which is labeled with a FAM™ dye, and/or one probe comprising the sequence of SEQ ID NO: 15 which is labeled with a VIC™ dye,
   a set of probes comprising one probe comprising the sequence of SEQ ID NO: 18 which is labeled with a FAM™ dye, and/or one probe comprising the sequence of SEQ ID NO: 19 which is labeled with a VIC™ dye.

---

The invention claimed is:

1. A *Brassica napus* plant, or a cell, part, seed or progeny thereof, comprising two non-naturally occurring full knock-out alc genes, wherein one non-naturally occurring full knock-out alc gene is a mutated version of the native ALC gene comprising at least 98% sequence identity to SEQ ID NO: 3 or encoding an amino acid sequence comprising at least 98% sequence identity to SEQ ID NO: 9; and wherein one non-naturally occurring full knock-out alc gene is a mutated version of the native ALC gene comprising at least 98% sequence identity to SEQ ID NO: 4 or encoding an amino acid sequence comprising at least 98% sequence identity to SEQ ID NO: 10;
  wherein said full knock-out mutant alc gene comprises a mutated DNA region consisting of one or more inserted, deleted or substituted nucleotides compared to a corresponding wild-type DNA region in the functional ALC gene and wherein said mutant alc allele does not encode a functional ALC protein,
  wherein the podshatter resistance is increased as compared to the podshatter resistance of a corresponding plant not comprising full knock-out alc genes.

2. A plant according to claim 1, wherein one non-naturally occurring full knock-out alc gene is an ALC gene from the A genome containing a mutated splice site characterized by a G to A substitution at position 668 of SEQ ID NO: 3; and wherein one non-naturally occurring full knock-out alc gene is an ALC gene from the C genome containing a premature stopcodon characterized by a C to T substitution at position 646 of SEQ ID NO: 4.

3. A plant according to claim 1, which is homozygous for the full knock-out alc genes.

4. A plant according to claim 1, which produces no functional ALC protein.

5. A plant according to claim 1, which maintains an agronomically relevant threshability of the pods.

6. A plant according to claim 1, wherein the seed yield of the plant is increased, preferably significantly increased compared to the seed yield of a corresponding plant not comprising non-naturally occurring full knock-out alc genes.

7. A seed pod obtainable from a plant according to claim 1.

8. A full knock-out allele of an ALC gene, wherein the ALC gene from A genome contains a mutated splice site characterized by a G to A substitution at position 668 of SEQ ID NO: 3, and wherein the ALC gene from C genome contains a premature stopcodon characterized by a C to T substitution at position 646 of SEQ ID NO: 4.

9. A method for identifying the *Brassica napus* plant, or a cell, part, seed or progeny thereof, of claim 1, said method comprising identifying said two full knock-out alc genes as described in claim 1 in a biological sample comprising determining the presence of a full knock-out alc specific region of each full knock-out gene in a nucleic acid present in the biological sample.

* * * * *